United States Patent
Kamtekar et al.

(10) Patent No.: US 10,954,496 B2
(45) Date of Patent: Mar. 23, 2021

(54) METHODS, SYSTEMS, AND REAGENTS FOR DIRECT RNA SEQUENCING

(71) Applicant: Pacific Biosciences of California, Inc., Menlo Park, CA (US)

(72) Inventors: Satwik Kamtekar, Mountain View, CA (US); Jeremiah Hanes, Woodside, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 14 days.

(21) Appl. No.: 16/354,878

(22) Filed: Mar. 15, 2019

(65) Prior Publication Data

US 2019/0352621 A1    Nov. 21, 2019

Related U.S. Application Data

(63) Continuation of application No. 15/334,935, filed on Oct. 26, 2016, now Pat. No. 10,280,411.

(60) Provisional application No. 62/246,897, filed on Oct. 27, 2015, provisional application No. 62/288,818, filed on Jan. 29, 2016.

(51) Int. Cl.
| | |
|---|---|
| *C12N 9/12* | (2006.01) |
| *C12Q 1/6869* | (2018.01) |
| *C12M 1/42* | (2006.01) |
| *C12P 19/34* | (2006.01) |

(52) U.S. Cl.
CPC ........... *C12N 9/1276* (2013.01); *C12M 1/42* (2013.01); *C12N 9/1241* (2013.01); *C12P 19/34* (2013.01); *C12Q 1/6869* (2013.01)

(58) Field of Classification Search
CPC ........................... C12N 9/1276; C12Q 1/6869
See application file for complete search history.

(56) References Cited

U.S. PATENT DOCUMENTS

| | | |
|---|---|---|
| 5,001,050 A | 3/1991 | Blanco et al. |
| 5,198,543 A | 3/1993 | Blanco et al. |
| 5,328,824 A | 7/1994 | Ward et al. |
| 5,476,928 A | 12/1995 | Ward et al. |
| 5,576,204 A | 11/1996 | Blanco et al. |
| 5,795,782 A | 8/1998 | Church et al. |
| 6,362,002 B1 | 3/2002 | Denison et al. |

(Continued)

FOREIGN PATENT DOCUMENTS

| | | |
|---|---|---|
| EP | 2145956 B1 | 1/2010 |
| EP | 1951898 B1 | 2/2012 |

(Continued)

OTHER PUBLICATIONS

Appleby et al., "Structural Basis for RNA Replication by the Hepatitis C Virus Polymerase," Science (2015) 347 (6223):771-775.

(Continued)

*Primary Examiner* — Richard G Hutson
(74) *Attorney, Agent, or Firm* — Monicia Elrod-Erickson

(57) ABSTRACT

Provided are compositions comprising recombinant polymerases that include amino acid substitutions, insertions, deletions, and/or exogenous features that confer modified properties upon the polymerase for sequencing RNA or RNA/DNA templates. Polymerases that topologically encircle the template nucleic acid are provided. Also provided are methods of using such polymerases to make a DNA or to sequence a template comprising RNA.

12 Claims, 6 Drawing Sheets
(5 of 6 Drawing Sheet(s) Filed in Color)
Specification includes a Sequence Listing.

(56) References Cited

U.S. PATENT DOCUMENTS

| | | |
|---|---|---|
| 6,673,615 B2 | 1/2004 | Denison et al. |
| 6,917,726 B2 | 7/2005 | Levene et al. |
| 7,033,764 B2 | 4/2006 | Korlach et al. |
| 7,041,812 B2 | 5/2006 | Kumar et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,745,116 B2 | 6/2010 | Williams |
| 7,858,311 B2 | 12/2010 | Williams |
| 7,907,800 B2 | 3/2011 | Foquet et al. |
| 7,939,256 B2 | 5/2011 | Williams |
| 7,968,702 B2 | 6/2011 | Wegener et al. |
| 8,153,375 B2 | 4/2012 | Travers et al. |
| 8,252,911 B2 | 8/2012 | Bjornson et al. |
| 8,501,405 B2 | 8/2013 | Korlach et al. |
| 8,501,406 B1 | 8/2013 | Gray et al. |
| 8,530,164 B2 | 9/2013 | Patel et al. |
| 8,603,741 B2 | 12/2013 | Emig et al. |
| 8,652,779 B2 | 2/2014 | Turner et al. |
| 8,802,600 B2 | 8/2014 | Rank et al. |
| 8,999,674 B2 | 4/2015 | Beechem et al. |
| 9,017,937 B1 | 4/2015 | Turner et al. |
| 9,062,091 B2 | 6/2015 | Bjornson et al. |
| 9,116,118 B2 | 8/2015 | Turner et al. |
| 9,150,918 B2 | 10/2015 | Turner et al. |
| 9,175,338 B2 | 11/2015 | Flusberg et al. |
| 9,175,341 B2 | 11/2015 | Flusberg et al. |
| 9,441,269 B2 | 9/2016 | Bauer et al. |
| 2003/0044781 A1 | 3/2003 | Korlach et al. |
| 2003/0124576 A1 | 7/2003 | Kumar et al. |
| 2003/0228616 A1 | 12/2003 | Arezi et al. |
| 2004/0259082 A1 | 12/2004 | Williams |
| 2007/0072196 A1 | 3/2007 | Xu et al. |
| 2007/0196846 A1 | 8/2007 | Hanzel et al. |
| 2008/0108082 A1 | 5/2008 | Rank et al. |
| 2009/0208957 A1 | 8/2009 | Korlach et al. |
| 2009/0286245 A1 | 11/2009 | Bjornson et al. |
| 2010/0075332 A1 | 3/2010 | Patel et al. |
| 2010/0093555 A1 | 4/2010 | Bjornson et al. |
| 2010/0112645 A1 | 5/2010 | Clark et al. |
| 2010/0152424 A1 | 6/2010 | Korlach et al. |
| 2010/0167299 A1 | 7/2010 | Korlach |
| 2010/0260465 A1 | 10/2010 | Hanzel et al. |
| 2010/0261247 A1 | 10/2010 | Hanzel et al. |
| 2011/0014612 A1 | 1/2011 | Hendricks et al. |
| 2011/0165652 A1 | 7/2011 | Hardin et al. |
| 2011/0183320 A1 | 7/2011 | Flusberg et al. |
| 2011/0189659 A1 | 8/2011 | Clark et al. |
| 2012/0034602 A1 | 2/2012 | Emig et al. |
| 2012/0077189 A1 | 3/2012 | Shen et al. |
| 2013/0217007 A1 | 8/2013 | Kamtekar et al. |
| 2013/0316912 A1 | 11/2013 | Bjornson et al. |
| 2014/0094374 A1 | 4/2014 | Kamtekar et al. |
| 2014/0094375 A1 | 4/2014 | Kamtekar et al. |
| 2015/0050659 A1 | 2/2015 | Sebo et al. |
| 2015/0065353 A1 | 3/2015 | Turner et al. |
| 2015/0086994 A1 | 3/2015 | William et al. |
| 2015/0152492 A1 | 6/2015 | Brown et al. |

FOREIGN PATENT DOCUMENTS

| | | |
|---|---|---|
| WO | 2007041342 A2 | 4/2007 |
| WO | 2009114182 A1 | 9/2009 |
| WO | 2011067559 A1 | 6/2011 |
| WO | 2014013260 A1 | 1/2014 |
| WO | 2014013262 A1 | 1/2014 |
| WO | 2019241305 A1 | 12/2019 |

OTHER PUBLICATIONS

Avidan and Amnon, "The Processivity of DNA Synthesis Exhibited by Drug-Resistant Variants of Human Immunodeficiency Virus Type-1 Reverse Transcriptase," Nucl. Acids Res. (1998) 26(7):1713-1717.

Berman et al., "Structures of phi29 DNA polymerase complexed with substrate: The mechanism of translocation in B-family polymerases" EMBO J. (2007) 26:3494-3505.

Bonnin et al., "A Single Tyrosine Prevents Insertion of Ribonucleotides in the Eukaryotic-Type Phi29 DNA Polymerase" J Mol Biol. (1999) 290(1):241-51.

Bressanelli et al., "Structural Analysis of the Hepatitis C Virus RNA Polymerase in Complex with Ribonucleotides," Journal of Virology (2002) 76(7):3482-92.

Bressanelli, "Kickstarting a Viral RNA Polymerase," Structural Biology (2015) 347(6223):715-6.

Ceccherini-Silbersten et al., "High Sequence Conservation of Human Immunodeficiency Virus Type 1 Reverse Tanscriptase Under Drug Pressure Despite the Continuous Appearance of Mutations," JournVirology (2005) 10718-10729.

Cozens et al., "A Short Adaptive Path form DNA to RNA Polymerases," PNAS (2012) 109(21):8067-8072.

De Vega et al., "Improvement of φ29 DNA Polymerase Amplification Performance by Fusion of DNA Binding Motifs," PNAS (2010) 107(38):16506-16511.

Ding et al., "Structure and Functional Implications of the Polymerase Active Site Region in a Complex of HIV-1 RT with a Double-Stranded DNA Template-Primer and an Antibody Fab Fragment at 2.8 A Aesolution," J Mol Biol. (1998) 284:1095-1111.

Eid et al., "Real-Time DNA Sequencing From Single Polymerase Molecules," Science (2009) 323:133-138.

Ellefson et al., "Synthetic Evolutionary Origin of a Proofreading Reverse Transcriptase," Science (2016) 352: 1590-1593.

Hsiou et al., "Structure of Unliganded HIV-1 Reverse Transcriptase at 2.7 A Resolution: Implications of Conformational Changes for Polymerization and Inhibition Mechanisms," Structure (1996) 4:853-860.

Huang et al., "Structure of a Covalently Trapped Catalytic Complex of HIV-1 Reverse Transcriptase: Implications for Drug Resistance," Science (1998) 282:1669-75.

Jacobo-Molina et al., "Crystal Structure of Human Immunodeficiency Virus Type 1 Reverse Transcriptase Complexed with Double-Stranded DNA at 3.0 A Resolution Shows Bent DNA," Proc Natl Acad Sci USA (1993) 90:6320-6324.

Jin et al., "Assembly, Purification, and Pre-Seady-State Kinetic Analysis of Active RNA-Dependent RNA Polymerase Elongation Complex," Journal of Biological Chemistry (2012) 287(13):10674-83.

Jin et al., "NTP-Mediated Nucleotide Excision Activity of Hepatitis C Virus RNA-Dependent RNA Polymerase," PNAS (2013) E348-E357.

Johnson, "Rapid Kinetic Analysis of Mechanochemical Adenosinetriphosphatases," Methods Enzymol. (1986) 134:677-705.

Kamtekar et al., "Insights into Strand Displacement and Processivity from the Crystal Structure of the Protein-Primed DNA Polymerase of Bacteriophage Φ29," Mol. Cell (2004) 16(4): 609-618.

Kamtekar et al., "The Phi29 DNA Polymerase:Protein-Primer Structure Suggests a Model for the Initiation to Elongation Transition," EMBO J. (2006) 25(6):1335-43.

Kensch et al., "Temperature-Dependent Equilibrium Between the Open and Closed Conformation of the p66 Subunit of HIV-1 Reverse Transcriptase Revealed by Site-Directed Spin Labelling," J. Mol. Biol. (2000) 301:1029-1039.

Kohlstaedt et al. (1992) "Crystal structure at 3.5 A resolution of HIV-1 reverse transcriptase complexed with an inhibitor" Science 256:1783-1790.

Korlach et al., "Long, Processive Enzymatic DNA Synthesis Using 100% Dye-Labeled Terminal Phosphate-Linked Nucleotides," Nucleosides, Nucleotides and Nucleic Acids (2008) 27:1072-1083.

Korlach et al., "Selective Aluminum Passivation for Targeted Immobilization of Single DNA Polymerase Molecules in Zero-Mode Waveguide Nanostructures," PNAS U.S.A. (2008) 105(4):1176-1181.

(56) References Cited

OTHER PUBLICATIONS

Kvaratskhelia et al., "Identification of Specific HIV-1 Reverse Transcriptase Contacts to the Viral RNA:tRNA Complex by Mass Spectrometry and a Primary Amine Selective Reagent," PNAS (2002) 99(25):15988-15993.
Levene et al., "Zero-mode Waveguides for Single-molecule Analysis at High Concentration" Science (2003) 299:682-686.
Manrao et al., "Reading DNA at Single-Nucleotide Resolution with a Mutant MspA Nanopore and Phi29 DNA Polymerase," Nature Biotechnology (2012) 30:349-353.
Meijer et al., "Φ29 Family of Phages," Microbiology and Molecular Biology Reviews (2001) 65(2):261-287.
Mirsaidov et al., "Nanoelectromechanics of Methylated DNA in a Synthetic Nanopore," Biophys. J. (2009) 96:L32-L34.
Mosley et al., "Structure of Hepatitis C Virus Polymerase in Complex with Primer-Template RNA," Journal of Virology (2012) 86(12):6503-6511.
Patel et al., "Pre-Steady-State Kinetic Analysis of Processive DNA Replication Including Complete Characterization of an Exonuclease-Deficient Mutant," Biochemistry (1991) 30(2):511-25.
Pinheiro et al., "Synthetic Genetic Polymers Capable of Heredity and Evolution," Science (2012) 336:341-344.
Ren et al., "High Resolution Structures of HIV-1 RT from Four RT-Inhibitor Complexes," (1995) Nat Struct Biol. 2:293-302.
Rodgers et al., "The Structure of Unliganded Reverse Transcriptase from the Human Immunodeficiency Virus Type 1," Proc Natl Acad Sci USA (1995) 92:1222-1226.
Sarafianos et al., "Crystal Structure of HIV-1 Reverse Transcriptase in Complex with a Polypurine Tract RNA:DNA," Embo J. (2001) 20:1449-1461.
Sarafianos et al., "Structures of HIV-1 Reverse Transcriptase with Pre- and Post-Translocation AZTMP-Terminated DNA," Embo J. (2002) 21:6614-6624.
Travers et al., "A Flexible and Efficient Template Format for Circular Consensus Sequencing and SNP Detection," Nucl. Acids Res. (2010) 38(15):e159.
Tsai and Johnson, "A New Paradigm for DNA Polymerase Specificity," Biochemistry (2006) 45(32):9675-87.
Vilfan et al., "Analysis of RNA Base Modification and Structural Rearrangement by Single-Molecule Real-Time Detection of Reverse Tanscription," Journal of Nanobiotechnology (2013) 11:8 doi:10.1186/1477-3155-11-8.
Wanunu et al., "Discrimination of Methylcytosine from Hydroxymethylcytosine in DNA Molecules," J. Am. Chem. Soc. (2010) 133:486-492.
Xia et al., "Directed Evolution of Novel Polymerase Activities: Mutation of a DNA Polymerase into a Efficient RNA Polymerase," PNAS (2002) 99(10):6597-6602.
Lagunavicius et al., Duality of Polynucleotide Substrates for Phi29 DNA Polymerase: 3' -> 5' Rnase Activity of the Enzyme, RNA Journal (2008) 14:503-13.
Ngo et al., "The Protein Folding Problem and Tertiary Structure Prediction," 1994, Merz et al. (ed.) Birkhauser, Boston, MA, pp. 433 and 492-495.

SEQUENCE LISTING

```
<160> NUMBER OF SEQ ID NOS: 6

<210> SEQ ID NO 1
<211> LENGTH: 575
<212> TYPE: PRT
<213> ORGANISM: Bacteriophage phi-29

<400> SEQUENCE: 1
```

| Met | Lys | His | Met | Pro | Arg | Lys | Met | Tyr | Ser | Cys | Asp | Phe | Glu | Thr | Thr |
|---|---|---|---|---|---|---|---|---|---|---|---|---|---|---|---|
| 1 | | | | 5 | | | | | 10 | | | | | 15 | |

| Thr | Lys | Val | Glu | Asp | Cys | Arg | Val | Trp | Ala | Tyr | Gly | Tyr | Met | Asn | Ile |
|---|---|---|---|---|---|---|---|---|---|---|---|---|---|---|---|
| | | | 20 | | | | | 25 | | | | | 30 | | |

| Glu | Asp | His | Ser | Glu | Tyr | Lys | Ile | Gly | Asn | Ser | Leu | Asp | Glu | Phe | Met |
| | | 35 | | | | | 40 | | | | | 45 | | | |

| Ala | Trp | Val | Leu | Lys | Val | Gln | Ala | Asp | Leu | Tyr | Phe | His | Asn | Leu | Lys |
| | 50 | | | | | 55 | | | | | 60 | | | | |

| Phe | Asp | Gly | Ala | Phe | Ile | Ile | Asn | Trp | Leu | Glu | Arg | Asn | Gly | Phe | Lys |
| 65 | | | | | 70 | | | | | 75 | | | | | 80 |

| Trp | Ser | Ala | Asp | Gly | Leu | Pro | Asn | Thr | Tyr | Asn | Thr | Ile | Ile | Ser | Arg |
| | | | | 85 | | | | | 90 | | | | | 95 | |

| Met | Gly | Gln | Trp | Tyr | Met | Ile | Asp | Ile | Cys | Leu | Gly | Tyr | Lys | Gly | Lys |
| | | | | 100 | | | | | 105 | | | | | 110 | |

| Arg | Lys | Ile | His | Thr | Val | Ile | Tyr | Asp | Ser | Leu | Lys | Lys | Leu | Pro | Phe |
| | | | 115 | | | | | 120 | | | | | 125 | | |

| Pro | Val | Lys | Lys | Ile | Ala | Lys | Asp | Phe | Lys | Leu | Thr | Val | Leu | Lys | Gly |
| 130 | | | | | 135 | | | | | 140 | | | | | |

| Asp | Ile | Asp | Tyr | His | Lys | Glu | Arg | Pro | Val | Gly | Tyr | Lys | Ile | Thr | Pro |
| 145 | | | | 150 | | | | | 155 | | | | | 160 | |

| Glu | Glu | Tyr | Ala | Tyr | Ile | Lys | Asn | Asp | Ile | Gln | Ile | Ile | Ala | Glu | Ala |
| | | | | 165 | | | | | 170 | | | | | 175 | |

| Leu | Leu | Ile | Gln | Phe | Lys | Gln | Gly | Leu | Asp | Arg | Met | Thr | Ala | Gly | Ser |
| | | | 180 | | | | | 185 | | | | | 190 | | |

| Asp | Ser | Leu | Lys | Gly | Phe | Lys | Asp | Ile | Ile | Thr | Thr | Lys | Lys | Phe | Lys |
| | | | 195 | | | | | 200 | | | | | 205 | | |

| Lys | Val | Phe | Pro | Thr | Leu | Ser | Leu | Gly | Leu | Asp | Lys | Glu | Val | Arg | Tyr |
| | 210 | | | | | 215 | | | | | 220 | | | | |

| Ala | Tyr | Arg | Gly | Gly | Phe | Thr | Trp | Leu | Asn | Asp | Arg | Phe | Lys | Glu | Lys |
| 225 | | | | | 230 | | | | | 235 | | | | | 240 |

| Glu | Ile | Gly | Glu | Gly | Met | Val | Phe | Asp | Val | Asn | Ser | Leu | Tyr | Pro | Ala |
| | | | | 245 | | | | | 250 | | | | | 255 | |

| Gln | Met | Tyr | Ser | Arg | Leu | Leu | Pro | Tyr | Gly | Glu | Pro | Ile | Val | Phe | Glu |
| | | | 260 | | | | | 265 | | | | | 270 | | |

| Gly | Lys | Tyr | Val | Trp | Asp | Glu | Asp | Tyr | Pro | Leu | His | Ile | Gln | His | Ile |
| | | | 275 | | | | | 280 | | | | | 285 | | |

| Arg | Cys | Glu | Phe | Glu | Leu | Lys | Glu | Gly | Tyr | Ile | Pro | Thr | Ile | Gln | Ile |
| | 290 | | | | | 295 | | | | | 300 | | | | |

| Lys | Arg | Ser | Arg | Phe | Tyr | Lys | Gly | Asn | Glu | Tyr | Leu | Lys | Ser | Ser | Gly |
| 305 | | | | | 310 | | | | | 315 | | | | | 320 |

| Gly | Glu | Ile | Ala | Asp | Leu | Trp | Leu | Ser | Asn | Val | Asp | Leu | Glu | Leu | Met |
| | | | | 325 | | | | | 330 | | | | | 335 | |

| Lys | Glu | His | Tyr | Asp | Leu | Tyr | Asn | Val | Glu | Tyr | Ile | Ser | Gly | Leu | Lys |
| | | | 340 | | | | | 345 | | | | | 350 | | |

Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
            515                 520                 525

Lys Cys Ala Gly Met Thr Asp Lys Ile Lys Lys Glu Val Thr Phe Glu
            530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 2
<211> LENGTH: 572
<212> TYPE: PRT
<213> ORGANISM: Bacteriophage M2Y

<400> SEQUENCE: 2

Met Ser Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asn Leu Lys Phe Asp Gly
    50                  55                  60

Ala Phe Ile Val Asn Trp Leu Glu Gln His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Thr Glu Arg Pro Val Gly His Glu Ile Thr Pro Glu Glu Tyr
145                 150                 155                 160

```
Glu Tyr Ile Lys Asn Asp Ile Glu Ile Ile Ala Arg Ala Leu Asp Ile
                165                 170                 175
Gln Phe Lys Gln Gly Leu Asp Arg Met Thr Ala Gly Ser Asp Ser Leu
            180                 185                 190
Lys Gly Phe Lys Asp Ile Leu Ser Thr Lys Lys Phe Asn Lys Val Phe
        195                 200                 205
Pro Lys Leu Ser Leu Pro Met Asp Lys Glu Ile Arg Lys Ala Tyr Arg
    210                 215                 220
Gly Gly Phe Thr Trp Leu Asn Asp Lys Tyr Lys Glu Lys Glu Ile Gly
225                 230                 235                 240
Glu Gly Met Val Phe Asp Val Asn Ser Leu Tyr Pro Ser Gln Met Tyr
                245                 250                 255
Ser Arg Pro Leu Pro Tyr Gly Ala Pro Ile Val Phe Gln Gly Lys Tyr
            260                 265                 270
Glu Lys Asp Glu Gln Tyr Pro Leu Tyr Ile Gln Arg Ile Arg Phe Glu
        275                 280                 285
Phe Glu Leu Lys Glu Gly Tyr Ile Pro Thr Ile Gln Ile Lys Lys Asn
    290                 295                 300
Pro Phe Phe Lys Gly Asn Glu Tyr Leu Lys Asn Ser Gly Val Glu Pro
305                 310                 315                 320
Val Glu Leu Tyr Leu Thr Asn Val Asp Leu Glu Leu Ile Gln Glu His
                325                 330                 335
Tyr Glu Leu Tyr Asn Val Glu Tyr Ile Asp Gly Phe Lys Phe Arg Glu
            340                 345                 350
Lys Thr Gly Leu Phe Lys Asp Phe Ile Asp Lys Trp Thr Tyr Val Lys
        355                 360                 365
Thr His Glu Glu Gly Ala Lys Lys Gln Leu Ala Lys Leu Met Leu Asn
    370                 375                 380
Ser Leu Tyr Gly Lys Phe Ala Ser Asn Pro Asp Val Thr Gly Lys Val
385                 390                 395                 400
Pro Tyr Leu Lys Asp Asp Gly Ser Leu Gly Phe Arg Val Gly Asp Glu
                405                 410                 415
Glu Tyr Lys Asp Pro Val Tyr Thr Pro Met Gly Val Phe Ile Thr Ala
            420                 425                 430
Trp Ala Arg Phe Thr Thr Ile Thr Ala Ala Gln Ala Cys Tyr Asp Arg
        435                 440                 445
Ile Ile Tyr Cys Asp Thr Asp Ser Ile His Leu Thr Gly Thr Glu Val
    450                 455                 460
Pro Glu Ile Ile Lys Asp Ile Val Asp Pro Lys Lys Leu Gly Tyr Trp
465                 470                 475                 480
Ala His Glu Ser Thr Phe Lys Arg Ala Lys Tyr Leu Arg Gln Lys Thr
                485                 490                 495
Tyr Ile Gln Asp Ile Tyr Val Lys Glu Val Asp Gly Lys Leu Lys Glu
            500                 505                 510
Cys Ser Pro Asp Glu Ala Thr Thr Lys Phe Ser Val Lys Cys Ala
        515                 520                 525
Gly Met Thr Asp Thr Ile Lys Lys Val Thr Phe Asn Phe Ala
    530                 535                 540
Val Gly Phe Ser Ser Met Gly Lys Pro Lys Pro Val Gln Val Asn Gly
545                 550                 555                 560
Gly Val Val Leu Val Asp Ser Val Phe Thr Ile Lys
                565                 570
```

```
<210> SEQ ID NO 3
<211> LENGTH: 562
<212> TYPE: PRT
<213> ORGANISM: Human immunodeficiency virus

<400> SEQUENCE: 3

Met Pro Ile Ser Pro Ile Glu Thr Val Pro Val Lys Leu Lys Pro Gly
1               5                   10                  15

Met Asp Gly Pro Lys Val Lys Gln Trp Pro Leu Thr Glu Glu Lys Ile
            20                  25                  30

Lys Ala Leu Val Glu Ile Cys Thr Glu Met Glu Lys Glu Gly Lys Ile
        35                  40                  45

Ser Lys Ile Gly Pro Glu Asn Pro Tyr Asn Thr Pro Val Phe Ala Ile
    50                  55                  60

Lys Lys Lys Asp Ser Thr Lys Trp Arg Lys Leu Val Asp Phe Arg Glu
65                  70                  75                  80

Leu Asn Lys Arg Thr Gln Asp Phe Trp Glu Val Gln Leu Gly Ile Pro
                85                  90                  95

His Pro Ala Gly Leu Lys Lys Lys Ser Val Thr Val Leu Asp Val
            100                 105                 110

Gly Asp Ala Tyr Phe Ser Val Pro Leu Asp Glu Asp Phe Arg Lys Tyr
        115                 120                 125

Thr Ala Phe Thr Ile Pro Ser Ile Asn Asn Glu Thr Pro Gly Ile Arg
    130                 135                 140

Tyr Gln Tyr Asn Val Leu Pro Gln Gly Trp Lys Gly Ser Pro Ala Ile
145                 150                 155                 160

Phe Gln Ser Ser Met Thr Lys Ile Leu Glu Pro Phe Arg Lys Gln Asn
                165                 170                 175

Pro Asp Ile Val Ile Tyr Gln Tyr Met Asp Asp Leu Tyr Val Gly Ser
            180                 185                 190

Asp Leu Glu Ile Gly Gln His Arg Thr Lys Ile Glu Glu Leu Arg Gln
        195                 200                 205

His Leu Leu Arg Trp Gly Leu Thr Thr Pro Asp Lys Lys His Gln Lys
    210                 215                 220

Glu Pro Pro Phe Leu Trp Met Gly Tyr Glu Leu His Pro Asp Lys Trp
225                 230                 235                 240

Thr Val Gln Pro Ile Val Leu Pro Glu Lys Asp Ser Trp Thr Val Asn
                245                 250                 255

Asp Ile Gln Lys Leu Val Gly Lys Leu Asn Trp Ala Ser Gln Ile Tyr
            260                 265                 270

Pro Gly Ile Lys Val Arg Gln Leu Cys Lys Leu Leu Arg Gly Thr Lys
        275                 280                 285

Ala Leu Thr Glu Val Ile Pro Leu Thr Glu Glu Ala Glu Leu Glu Leu
    290                 295                 300

Ala Glu Asn Arg Glu Ile Leu Lys Glu Pro Val His Gly Val Tyr Tyr
305                 310                 315                 320

Asp Pro Ser Lys Asp Leu Ile Ala Glu Ile Gln Lys Gln Gly Gln Gly
                325                 330                 335

Gln Trp Thr Tyr Gln Ile Tyr Gln Glu Pro Phe Lys Asn Leu Lys Thr
            340                 345                 350

Gly Lys Tyr Ala Arg Met Arg Gly Ala His Thr Asn Asp Val Lys Gln
        355                 360                 365

Leu Thr Glu Ala Val Gln Lys Ile Thr Thr Glu Ser Ile Val Ile Trp
    370                 375                 380
```

Gly Lys Thr Pro Lys Phe Lys Leu Pro Ile Gln Lys Glu Thr Trp Glu
385                 390                 395                 400

Thr Trp Trp Thr Glu Tyr Trp Gln Ala Thr Trp Ile Pro Glu Trp Glu
            405                 410                 415

Phe Val Asn Thr Pro Pro Leu Val Lys Leu Trp Tyr Gln Leu Glu Lys
        420                 425                 430

Glu Pro Ile Val Gly Ala Glu Thr Phe Tyr Val Asp Gly Ala Ala Asn
            435                 440                 445

Arg Glu Thr Lys Leu Gly Lys Ala Gly Tyr Val Thr Asn Arg Gly Arg
        450                 455                 460

Gln Lys Val Val Thr Leu Thr Asp Thr Thr Asn Gln Lys Thr Glu Leu
465                 470                 475                 480

Gln Ala Ile Tyr Leu Ala Leu Gln Asp Ser Gly Leu Glu Val Asn Ile
            485                 490                 495

Val Thr Asp Ser Gln Tyr Ala Leu Gly Ile Ile Gln Ala Gln Pro Asp
        500                 505                 510

Gln Ser Glu Ser Glu Leu Val Asn Gln Ile Ile Glu Gln Leu Ile Lys
            515                 520                 525

Lys Glu Lys Val Tyr Leu Ala Trp Val Pro Ala His Lys Gly Ile Gly
        530                 535                 540

Gly Asn Glu Gln Val Asp Lys Leu Val Ser Ala Gly Ile Arg Lys Val
545                 550                 555                 560

Leu Phe

<210> SEQ ID NO 4
<211> LENGTH: 427
<212> TYPE: PRT
<213> ORGANISM: Human immunodeficiency virus

<400> SEQUENCE: 4

Met Pro Ile Ser Pro Ile Glu Thr Val Pro Val Lys Leu Lys Pro Gly
1               5                   10                  15

Met Asp Gly Pro Lys Val Lys Gln Trp Pro Leu Thr Glu Glu Lys Ile
            20                  25                  30

Lys Ala Leu Val Glu Ile Cys Thr Glu Met Glu Lys Glu Gly Lys Ile
        35                  40                  45

Ser Lys Ile Gly Pro Glu Asn Pro Tyr Asn Thr Pro Val Phe Ala Ile
    50                  55                  60

Lys Lys Lys Asp Ser Thr Lys Trp Arg Lys Leu Val Asp Phe Arg Glu
65                  70                  75                  80

Leu Asn Lys Arg Thr Gln Asp Phe Trp Glu Val Gln Leu Gly Ile Pro
                85                  90                  95

His Pro Ala Gly Leu Lys Lys Lys Ser Val Thr Val Leu Asp Val
            100                 105                 110

Gly Asp Ala Tyr Phe Ser Val Pro Leu Asp Glu Asp Phe Arg Lys Tyr
        115                 120                 125

Thr Ala Phe Thr Ile Pro Ser Ile Asn Asn Glu Thr Pro Gly Ile Arg
    130                 135                 140

Tyr Gln Tyr Asn Val Leu Pro Gln Gly Trp Lys Gly Ser Pro Ala Ile
145                 150                 155                 160

Phe Gln Ser Ser Met Thr Lys Ile Leu Glu Pro Phe Arg Lys Gln Asn
                165                 170                 175

Pro Asp Ile Val Ile Tyr Gln Tyr Met Asp Asp Leu Tyr Val Gly Ser
            180                 185                 190

```
Asp Leu Glu Ile Gly Gln His Arg Thr Lys Ile Glu Glu Leu Arg Gln
            195                 200                 205

His Leu Leu Arg Trp Gly Leu Thr Thr Pro Asp Lys Lys His Gln Lys
    210                 215                 220

Glu Pro Pro Phe Leu Trp Met Gly Tyr Glu Leu His Pro Asp Lys Trp
225                 230                 235                 240

Thr Val Gln Pro Ile Val Leu Pro Glu Lys Asp Ser Trp Thr Val Asn
                245                 250                 255

Asp Ile Gln Lys Leu Val Gly Lys Leu Asn Trp Ala Ser Gln Ile Tyr
            260                 265                 270

Pro Gly Ile Lys Val Arg Gln Leu Cys Lys Leu Leu Arg Gly Thr Lys
        275                 280                 285

Ala Leu Thr Glu Val Ile Pro Leu Thr Glu Glu Ala Glu Leu Glu Leu
    290                 295                 300

Ala Glu Asn Arg Glu Ile Leu Lys Glu Pro Val His Gly Val Tyr Tyr
305                 310                 315                 320

Asp Pro Ser Lys Asp Leu Ile Ala Glu Ile Gln Lys Gln Gly Gln Gly
                325                 330                 335

Gln Trp Thr Tyr Gln Ile Tyr Gln Glu Pro Phe Lys Asn Leu Lys Thr
            340                 345                 350

Gly Lys Tyr Ala Arg Met Arg Gly Ala His Thr Asn Asp Val Lys Gln
        355                 360                 365

Leu Thr Glu Ala Val Gln Lys Ile Thr Thr Glu Ser Ile Val Ile Trp
    370                 375                 380

Gly Lys Thr Pro Lys Phe Lys Leu Pro Ile Gln Lys Glu Thr Trp Glu
385                 390                 395                 400

Thr Trp Trp Thr Glu Tyr Trp Gln Ala Thr Trp Ile Pro Glu Trp Glu
                405                 410                 415

Phe Val Asn Thr Pro Pro Leu Val Lys Leu Trp
            420                 425

<210> SEQ ID NO 5
<211> LENGTH: 14
<212> TYPE: PRT
<213> ORGANISM: Artificial Sequence
<220> FEATURE:
<223> OTHER INFORMATION: peptide linker

<400> SEQUENCE: 5

Gly Gly Gly Ser Leu Val Pro Arg Gly Ser Gly Gly Gly Ser
1               5                   10

<210> SEQ ID NO 6
<211> LENGTH: 12
<212> TYPE: PRT
<213> ORGANISM: Artificial Sequence
<220> FEATURE:
<223> OTHER INFORMATION: peptide linker

<400> SEQUENCE: 6

Gly Gly Gly Ser Gly Gly Gly Ser Gly Gly Gly Ser
1               5                   10
```

METHODS, SYSTEMS, AND REAGENTS FOR DIRECT RNA SEQUENCING

CROSS-REFERENCE TO RELATED APPLICATIONS

This application is a continuation application of U.S. patent application Ser. No. 15/334,935, filed Oct. 26, 2016, which is a non-provisional utility patent application claiming priority to and benefit of the following prior provisional patent applications: U.S. Ser. No. 62/246,897, filed Oct. 27, 2015, entitled "METHODS, SYSTEMS, AND REAGENTS FOR DIRECT RNA SEQUENCING" by Satwik Kamtekar and Jeremiah Hanes, and U.S. Ser. No. 62/288,818, filed Jan. 29, 2016, entitled "METHODS, SYSTEMS, AND REAGENTS FOR DIRECT RNA SEQUENCING" by Satwik Kamtekar et al., each of which is incorporated herein by reference in its entirety for all purposes.

INCORPORATION-BY-REFERENCE OF MATERIAL SUBMITTED BY U.S.P.T.O. EFS-WEB

The instant application contains a Sequence Listing which is being submitted in computer readable form via the United States Patent and Trademark Office eFS-WEB system and which is hereby incorporated by reference in its entirety for all purposes. The txt file submitted herewith contains a 19 KB file (01019803_2019-08-01_SequenceListing.txt).

BACKGROUND OF THE INVENTION

The sets of all mRNA transcripts present in living cells, termed "transcriptomes," are fundamental units for regulating life processes. The direct and comprehensive determination of their sequence content is essential for improving our understanding of proteome constitution and flexibility, thereby providing the knowledge and targets to intervene in such diverse processes as cancer, tissue specificity, (auto)immune responses, genetic diseases, and environmental adaptation, to name but a few.

However, transcriptome analysis has proved a more difficult experimental task than determination of whole genomes, because, unlike DNA, mRNA transcripts in cells are present in highly uneven abundance and are variable in a context and environmentally sensitive manner RNA sequence information has been obtained conventionally by labor-intensive sequencing of expressed sequence tags (ESTs) and complementary DNA (cDNA) libraries, so few transcriptomes have been extensively characterized.

Sequencing of other RNAs likewise conventionally relies on their conversion to cDNAs followed by sequencing of the cDNAs. Inclusion of the conversion step is undesirable, since errors can be introduced during the process of reverse transcription and since information on base modifications and secondary structure important in RNA function is not preserved during conversion. Methods, systems, and reagents for convenient and accurate direct determination of RNA sequences, as well as RNA secondary structure and base modifications, are therefore desirable. The invention described herein fulfills these and other needs, as will be apparent upon review of the following.

SUMMARY OF THE INVENTION

Applications such as, e.g., single-molecule sequencing (SMS), sample preparation, and real-time monitoring of amplification, e.g., RT-PCR, can benefit from modified polymerases. Among other aspects, the invention provides recombinant polymerases that comprise mutations which confer properties which can be particularly desirable for these and other applications. These properties can, e.g., improve polymerase performance in direct RNA sequencing. Also provided by the invention are methods of generating such modified polymerases and methods in which such polymerases can be used, e.g., to sequence an RNA template and/or make a nucleic acid.

One general class of embodiments provides reaction mixtures, e.g., reaction mixtures for sequencing a nucleic acid template or making a nucleic acid product. The mixtures comprise a polymerase enzyme complex comprising a polymerase enzyme and a template nucleic acid that comprises RNA, wherein the polymerase topologically encircles the template nucleic acid. The template can be essentially any desired RNA, including, but not limited to, an mRNA, rRNA, tRNA, miRNA, piRNA, saRNA, siRNA, ribozyme, CRISPR RNA, catalytic RNA, antisense RNA, long ncRNA, or a fragment or derivative thereof. Optionally, the template is an RNA/DNA hybrid, e.g., a nucleic acid strand including at least one stretch of ribonucleotides and at least one stretch of deoxyribonucleotides. The region of ribonucleotides in the template typically includes 10 or more contiguous ribonucleotides, preferably 20 or more, 50 or more, 100 or more, 500 or more, 1000 or more, or even 2000 or more contiguous ribonucleotides. The template nucleic acid can be, e.g., linear or circular (e.g., a simple circle or a SMRTbell™). The template nucleic acid can be, e.g., single stranded or double stranded. The mixture optionally also includes a primer, e.g., a primer hybridized to the template nucleic acid.

The polymerase enzyme complex can be immobilized on a surface, e.g., through immobilization of the polymerase, primer, or template on the surface. Preferably, the enzyme complex is immobilized on the surface in an optical confinement. For example, the complex can be immobilized on or proximal to the bottom of a zero mode waveguide or other nanoscale well. In other embodiments, the complex is immobilized proximal to a nanopore. Immobilized complexes are particularly useful for single molecule sequencing. Thus, the reaction mixture optionally includes sequencing reagents in contact with the surface, which sequencing reagents comprise reagents for carrying out nucleic acid synthesis. Generally, these reagents include one or more nucleotides and/or nucleotide analogs, e.g., one or more labeled nucleotide analogs (e.g., four differently labeled nucleotide analogs). The reaction mixture can include a phosphate-labeled nucleotide analog, wherein the polymerase incorporates the nucleotide analog into a copy nucleic acid in response to the template nucleic acid. Optionally, the polymerase comprises one or more exogenous features at the C-terminal and/or N-terminal region of the polymerase (or a subunit thereof) and/or is exonuclease deficient.

In one class of embodiments, the polymerase is a recombinant Φ29-type polymerase. Optionally, the polymerase comprises an amino acid sequence that is at least 70% identical to SEQ ID NO:1 or at least 70% identical to SEQ ID NO:2 (e.g., at least 80% identical, at least 90% identical, or at least 95% identical, to SEQ ID NO:1 or 2). The polymerase can include at least one amino acid substitution (typically a pair of amino acid substitutions) facilitating formation of a covalent or noncovalent linkage resulting in the topological encirclement of the template. For example, the recombinant polymerase can include a pair of cysteine substitutions. In exemplary embodiments, the recombinant polymerase comprises a cysteine residue at position V19 and a cysteine residue at position N409, a cysteine residue at position D84 and a cysteine residue at position E418, a cysteine residue at position N409 and a cysteine residue at position V568, or a cysteine residue at position A83 and a cysteine residue at position E420, wherein identification of positions is relative to SEQ ID NO:1, and the side chains of the indicated two cysteine residues are covalently connected by a linker. Exemplary linkers are known in the art and include, e.g., bifunctional linkers including maleimide or iodoacetamide groups with PEG or amino acid spacers. The polymerase optionally includes amino acid substitutions that improve sequencing performance.

In another class of embodiments, the polymerase is a recombinant reverse transcriptase, e.g., a recombinant HIV reverse transcriptase. Optionally, the polymerase comprises an amino acid sequence that is at least 70% identical to SEQ ID NO:3 (e.g., at least 80% identical, at least 90% identical, or at least 95% identical to SEQ ID NO:3). Since HIV reverse transcriptase is a heterodimer, the reverse transcriptase typically also includes a second subunit having an amino acid sequence that is at least 70% identical to SEQ ID NO:4 (e.g., at least 80% identical, at least 90% identical, or at least 95% identical to SEQ ID NO:4). The polymerase can include at least one amino acid substitution (typically a pair of amino acid substitutions) facilitating formation of a covalent or noncovalent linkage resulting in the topological encirclement of the template. For example, the recombinant polymerase can include a pair of cysteine substitutions. In exemplary embodiments, the recombinant polymerase comprises a first cysteine residue at a position selected from W25, K14, and K23 and a second cysteine residue at a position selected from K288 and A289, wherein identification of positions is relative to SEQ ID NO:3, and the side chains of the first and second cysteine residues are covalently connected by a linker. Exemplary linkers are known in the art and include, e.g., bifunctional linkers including maleimide or iodoacetamide groups with PEG or amino acid spacers.

A related general class of embodiments provides methods for sequencing a nucleic acid template. In the methods, a polymerase enzyme complex comprising a polymerase enzyme, a template nucleic acid that comprises RNA, and optionally a primer hybridized to the template nucleic acid, wherein the polymerase topologically encircles the template nucleic acid, is provided. The polymerase enzyme complex is immobilized on a surface, e.g., through immobilization of the polymerase, primer, or template on the surface. Preferably, the enzyme complex is immobilized on the surface in an optical confinement. For example, the complex can be immobilized on or proximal to the bottom of a zero mode waveguide or other nanoscale well. In other embodiments, the complex is immobilized proximal to a nanopore. Sequencing reagents are added in contact with the surface, including reagents for carrying out nucleic acid synthesis (e.g., one or more nucleotides and/or nucleotide analogs, e.g., one or more labeled nucleotide analogs, e.g., four differently labeled nucleotide analogs). Sequential addition of nucleotide residues to a nucleic acid strand complementary to a strand of the template nucleic acid is determined by observing the interaction of the labeled nucleotide analogs with the polymerase enzyme complex. The methods are particularly applicable to single molecule, real time sequencing applications. Essentially all of the features noted for the compositions above apply to these methods as well, as relevant, for example, with respect to choice of polymerase, template, and the like.

Another related general class of embodiments provides systems for sequencing nucleic acids. The systems include a chip comprising a plurality of polymerase enzyme complexes bound thereto, each polymerase enzyme complex individually optically resolvable, each polymerase enzyme complex comprising a polymerase enzyme, a template nucleic acid comprising RNA, and optionally a primer hybridized to the template nucleic acid, wherein the polymerase topologically encircles the template. The systems also include sequencing reagents in contact with the surface, including reagents for carrying out nucleic acid synthesis (e.g., one or more nucleotides and/or nucleotide analogs, e.g., one or more labeled nucleotide analogs, e.g., four differently labeled nucleotide analogs). The systems also include an illumination system for illuminating the polymerase enzyme complexes, an optical detection system for detecting fluorescence from the labeled nucleotide analogs while they are interacting with the polymerase enzyme complexes, and a computer for analyzing the signals detected by the detection system to determine the sequential addition of nucleotide residues to a nucleic acid strand complementary to a strand of the template nucleic acid. Secondary structure and/or presence and/or location of modified bases in the template can also be detected. Essentially all of the features noted for the compositions above apply to the systems as well, as relevant, for example, with respect to choice of polymerase, template, and the like.

Another general class of embodiments provides compositions including a recombinant Φ29-type polymerase. Optionally, the polymerase comprises an amino acid sequence that is at least 70% identical to SEQ ID NO:1 or at least 70% identical to SEQ ID NO:2 (e.g., at least 80% identical, at least 90% identical, or at least 95% identical, to SEQ ID NO:1 or 2). The recombinant polymerase comprises one or more mutation selected from the group consisting of an amino acid substitution at position V19, an amino acid substitution at position N409, an amino acid substitution at position D84, an amino acid substitution at position E418, an amino acid substitution at position V568, an amino acid substitution at position A83, an amino acid substitution at position E420, an amino acid substitution at position T441, an amino acid substitution at position C106, an amino acid substitution at position C448, an amino acid substitution at position M97, an amino acid substitution at position P129, an amino acid substitution at position R306, an amino acid substitution at position R308, an amino acid substitution at position L416, an amino acid substitution at position T499, an amino acid substitution at position T534, an amino acid substitution at position D570, an amino acid substitution at position T571, an amino acid substitution at position T573, an amino acid substitution at position L389, an amino acid substitution at position Y390, an amino acid substitution at position G391, an amino acid substitution at position K392, an amino acid substitution at position F393, an amino acid substitution at position A394, an amino acid substitution at position S395, an amino acid substitution at position F363, an amino acid substitution at position F198Y, an amino acid substitution at position T17, an amino acid substitution at position D12, an amino acid substitution at position N62, an amino acid substitution at position Y148, an amino acid substitution at position D66, an amino acid substitution at position L253, an amino acid substitution at position A437, an amino acid substitution at position S192, an amino acid substitution at position Y101, an amino acid substitution at position Q497, an amino acid substitution at position K305, an amino acid substitution at position K575, an amino acid substitution at position R496, and an amino acid substitution at position K557, wherein identification of positions is relative to SEQ ID NO:1. For example, the polymerase can comprise one or more mutation selected from the group consisting of a V19C substitution, an N409C substitution, a D84C substitution, an E418C substitution, a V568C substitution, an A83C substitution, an A83E substitution, an A83D substitution, an E420C substitution, an E420R substitution, an E420K substitution, a T441L substitution, a C106S substitution, a C448V substitution, an M97L substitution, an M97A substitution, an M97K substitution, an M97E substitution, an M97R substitution, a P129R substitution, an R306Q substitution, an R306A substitution, an R306F substitution, a R306H substitution, an R306K substitution, an R306L substitution, an R306T substitution, an R308L substitution, an R308A substitution, an R308H substitution, an R308K substitution, an R308P substitution, an R308Q substitution, an L416A substitution, an L416E substitution, an L416H substitution, an L416I substitution, an L416S substitution, an L416T substitution, an L416Q substitution, an L416V substitution, a T499S substitution, a T534P substitution, a D570S substitution, a D570E substitution, a D570M substitution, a T571V substitution, a T571P substitution, a T573A substitution, a T573S substitution, a T573K substitution, an L389A substitution, an L389V substitution, an L389C substitution, an L389I substitution, a Y390F substitution, a Y390P substitution, a Y390H substitution, a Y390V substitution, a Y390L substitution, a K392A substitution, a K392R substitution, a K392H substitution, an F393L substitution, an F393A substitution, an F393V substitution, an A394 substitution, an S395A substitution, an S395T substitution, an S395G substitution, an F363L substitution, an F363V substitution, an F363W substitution, an F363A substitution, an F198Y substitution, a D12A substitution, a T17W substitution, an N62D substitution, a D66A substitution, a Y101F substitution, a Y148I substitution, an S192A substitution, an L253A substitution, a K305R substitution, an A437G substitution, an R496K substitution, a Q497R substitution, a Q497K substitution, a K557R substitution, a D570N substitution, a D570T substitution, and a K575R substitution, wherein identification of positions is relative to SEQ ID NO:1. Optionally, the recombinant polymerase comprises one or more exogenous features at the C-terminal and/or N-terminal region of the polymerase and/or is exonuclease deficient.

Generally, the composition also includes a template nucleic acid that comprises RNA. For example, the template can be essentially any desired RNA, including, but not limited to, an mRNA, rRNA, tRNA, miRNA, piRNA, saRNA, siRNA, ribozyme, CRISPR RNA, catalytic RNA, antisense RNA, long ncRNA, or a fragment or derivative thereof. Optionally, the template is an RNA/DNA hybrid, e.g., a nucleic acid strand including at least one stretch of ribonucleotides and at least one stretch of deoxyribonucleotides. The region of ribonucleotides in the template typically includes 10 or more contiguous ribonucleotides, preferably 20 or more, 50 or more, 100 or more, 500 or more, 1000 or more, or even 2000 or more contiguous ribonucleotides. The template nucleic acid can be, e.g., linear or circular (e.g., a simple circle or a SMRTbell™). The template nucleic acid can be, e.g., single stranded or double stranded. The mixture optionally also includes a primer, e.g., a primer hybridized to the template nucleic acid.

Polymerases of the invention find use in making nucleic acids and in sequencing, particularly single molecule real time sequencing. Thus, in one class of embodiments, the composition is present in a sequencing system, e.g., a single molecule sequencing system. In one class of embodiments, the sequencing system comprises a nanopore; the polymerase, the template, or a primer is typically immobilized proximal to the nanopore. In one class of embodiments, the sequencing system comprises a zero-mode waveguide. The recombinant polymerase can be immobilized on a surface of the zero-mode waveguide in an active form, or the template or a primer can be immobilized on the surface. Similarly, the recombinant polymerase, the template, or a primer can be immobilized on a surface in another type of optical confinement and/or nanoscale well in a sequencing system. The composition optionally includes a phosphate-labeled nucleotide analog, wherein the recombinant polymerase incorporates the nucleotide analog into a copy nucleic acid in response to the template nucleic acid. Essentially all of the features noted for the compositions above apply to these compositions as well, as relevant, for example, with respect to choice of template, topological encirclement of the template, and the like.

A related general class of embodiments provides methods of sequencing a template. In the methods, a reaction mixture is provided that includes i) a template nucleic acid comprising RNA, ii) a replication initiating moiety that complexes with or is integral to the template (e.g., a primer), iii) one or more nucleotides and/or nucleotide analogs (e.g., labeled nucleotide analogs), and iv) a recombinant Φ29-type polymerase of the invention. The polymerase is capable of replicating at least a portion of the template, e.g., using the moiety, in a template-dependent polymerization reaction. The reaction mixture is subjected to a polymerization reaction in which the recombinant polymerase replicates at least a portion of the template in a template-dependent manner, whereby nucleotide residues (from the one or more nucleotides and/or nucleotide analogs) are incorporated into the resulting DNA. A time sequence of incorporation of the nucleotide residues into the resulting DNA is identified. The sequence of the template can thus be determined, as can the presence of base modifications and secondary structure.

The nucleotide analogs used in the methods can comprise a first analog and a second analog (and optionally third, fourth, etc. analogs), each of which comprise different fluorescent labels. The different fluorescent labels can optionally be distinguished from one another during the step in which a time sequence of incorporation is identified. Optionally, subjecting the reaction mixture to a polymerization reaction and identifying a time sequence of incorporation are performed in a nanoscale well, e.g., a zero mode waveguide. Essentially all of the features noted for the compositions herein apply to these methods as well, as relevant, for example, with respect to choice of polymerase, template, topological encirclement, and the like.

In another related general class of embodiments, the invention provides methods of making a DNA. In the methods, a reaction mixture is provided that includes i) a template nucleic acid comprising RNA, ii) a recombinant Φ29-type polymerase of the invention, iii) a primer, and iv) one or more nucleotides and/or nucleotide analogs. The polymerase is capable of replicating at least a portion of the template in a template-dependent polymerase reaction. The mixture is reacted such that the polymerase replicates at least a portion of the template in a template-dependent manner, whereby nucleotide residues (from the one or more nucleotides and/or nucleotide analogs) are incorporated into the resulting DNA. The reaction mixture is optionally reacted in a nanoscale well, e.g., a zero mode waveguide. The methods optionally include detecting incorporation of at least one of the nucleotides and/or nucleotide analogs. Essentially all of the features noted for the compositions herein apply to these methods as well, as relevant, for example, with respect to choice of polymerase, template, topological encirclement, and the like.

Another general class of embodiments provides compositions including a recombinant HIV reverse transcriptase. Optionally, the polymerase comprises an amino acid sequence that is at least 70% identical to SEQ ID NO:3 (e.g., at least 80% identical, at least 90% identical, or at least 95% identical, to SEQ ID NO:3). The recombinant reverse transcriptase comprises one or more mutation selected from the group consisting of an amino acid substitution at position W25, an amino acid substitution at position K14, an amino acid substitution at position K23, an amino acid substitution at position K288, an amino acid substitution at position A289, an amino acid substitution at position A115, an amino acid substitution at position K66, an amino acid substitution at position K67, an amino acid substitution at position D68, an amino acid substitution at position K220, an amino acid substitution at position K221, an amino acid substitution at position V246, an amino acid substitution at position E90, and an amino acid substitution at position H222, wherein identification of positions is relative to SEQ ID NO:3. For example, the reverse transcriptase can comprise one or more mutation selected from the group consisting of a W25C substitution, a K14C substitution, a K23C substitution, a K288C substitution, an A289C substitution, an A115G substitution, an A115S substitution, a K66R substitution, a K66H substitution, a K67R substitution, a D68N substitution, a K220Q substitution, a K220W substitution, a K221E substitution, a V246K substitution, an E90K substitution, and an H222Y substitution, wherein identification of positions is relative to SEQ ID NO:3. The reverse transcriptase typically also includes a second subunit having an amino acid sequence that is at least 70% identical to SEQ ID NO:4 (e.g., at least 80% identical, at least 90% identical, or at least 95% identical, to SEQ ID NO:4). Optionally, the recombinant reverse transcriptase comprises one or more exogenous features at the C-terminal and/or N-terminal region of either subunit of the reverse transcriptase and/or is exonuclease deficient.

Generally, the composition also includes an RNA template nucleic acid. The template can be essentially any desired RNA, including, but not limited to, an mRNA, rRNA, tRNA, miRNA, piRNA, saRNA, siRNA, ribozyme, CRISPR RNA, catalytic RNA, antisense RNA, long ncRNA, or a fragment or derivative thereof.

Reverse transcriptases of the invention find use in making nucleic acids and in sequencing, particularly single molecule real time sequencing. Thus, in one class of embodiments, the composition is present in a sequencing system, e.g., a single molecule sequencing system. In one class of embodiments, the sequencing system comprises a nanopore; the reverse transcriptase, the template, or a primer is typically immobilized proximal to the nanopore. In one class of embodiments, the sequencing system comprises a zero-mode waveguide. The recombinant reverse transcriptase can be immobilized on a surface of the zero-mode waveguide in an active form, or the template or a primer can be immobilized on the surface. Similarly, the recombinant reverse transcriptase, the template, or a primer can be immobilized on a surface in another type of optical confinement and/or nanoscale well in a sequencing system. Essentially all of the features noted for the compositions above apply to these compositions as well, as relevant, for example, with respect to choice of template, inclusion of analogs, topological encirclement of the template, and the like.

A related general class of embodiments provides methods of sequencing a template. In the methods, a reaction mixture is provided that includes i) an RNA template nucleic acid, ii) a primer, iii) one or more nucleotides and/or nucleotide analogs (e.g., labeled nucleotide analogs), and iv) a recombinant HIV reverse transcriptase of the invention. The reverse transcriptase is capable of replicating at least a portion of the template, e.g., using the primer, in a template-dependent polymerization reaction. The reaction mixture is subjected to a polymerization reaction in which the recombinant reverse transcriptase replicates at least a portion of the template in a template-dependent manner, whereby nucleotide residues (from the one or more nucleotides and/or nucleotide analogs) are incorporated into the resulting DNA. A time sequence of incorporation of the nucleotide residues into the resulting DNA is identified. The sequence of the template can thus be determined, as can the presence of base modifications and secondary structure.

The nucleotide analogs used in the methods can comprise a first analog and a second analog (and optionally third, fourth, etc. analogs), each of which comprise different fluorescent labels. The different fluorescent labels can optionally be distinguished from one another during the step in which a time sequence of incorporation is identified. Optionally, subjecting the reaction mixture to a polymerization reaction and identifying a time sequence of incorporation are performed in a nanoscale well, e.g., a zero mode waveguide. Essentially all of the features noted for the compositions herein apply to these methods as well, as relevant, for example, with respect to choice of reverse transcriptase, template, topological encirclement, and the like.

In another related general class of embodiments, the invention provides methods of making a DNA. In the methods, a reaction mixture is provided that includes i) an RNA template nucleic acid, ii) a recombinant HIV reverse transcriptase of the invention, iii) a primer, and iv) one or more nucleotides and/or nucleotide analogs. The reverse transcriptase is capable of replicating at least a portion of the template in a template-dependent polymerase reaction. The mixture is reacted such that the reverse transcriptase replicates at least a portion of the template in a template-dependent manner, whereby nucleotide residues (from the one or more nucleotides and/or nucleotide analogs) are incorporated into the resulting DNA. The reaction mixture is optionally reacted in a nanoscale well, e.g., a zero mode waveguide. The methods optionally include detecting incorporation of at least one of the nucleotides and/or nucleotide analogs. Essentially all of the features noted for the compositions herein apply to these methods as well, as relevant, for example, with respect to choice of reverse transcriptase, template, topological encirclement, and the like.

BRIEF DESCRIPTION OF THE DRAWINGS

The patent or application file contains at least one drawing executed in color. Copies of this patent or patent application publication with color drawings will be provided by the Office upon request and payment of the necessary fee.

Figures 1A, 1B:
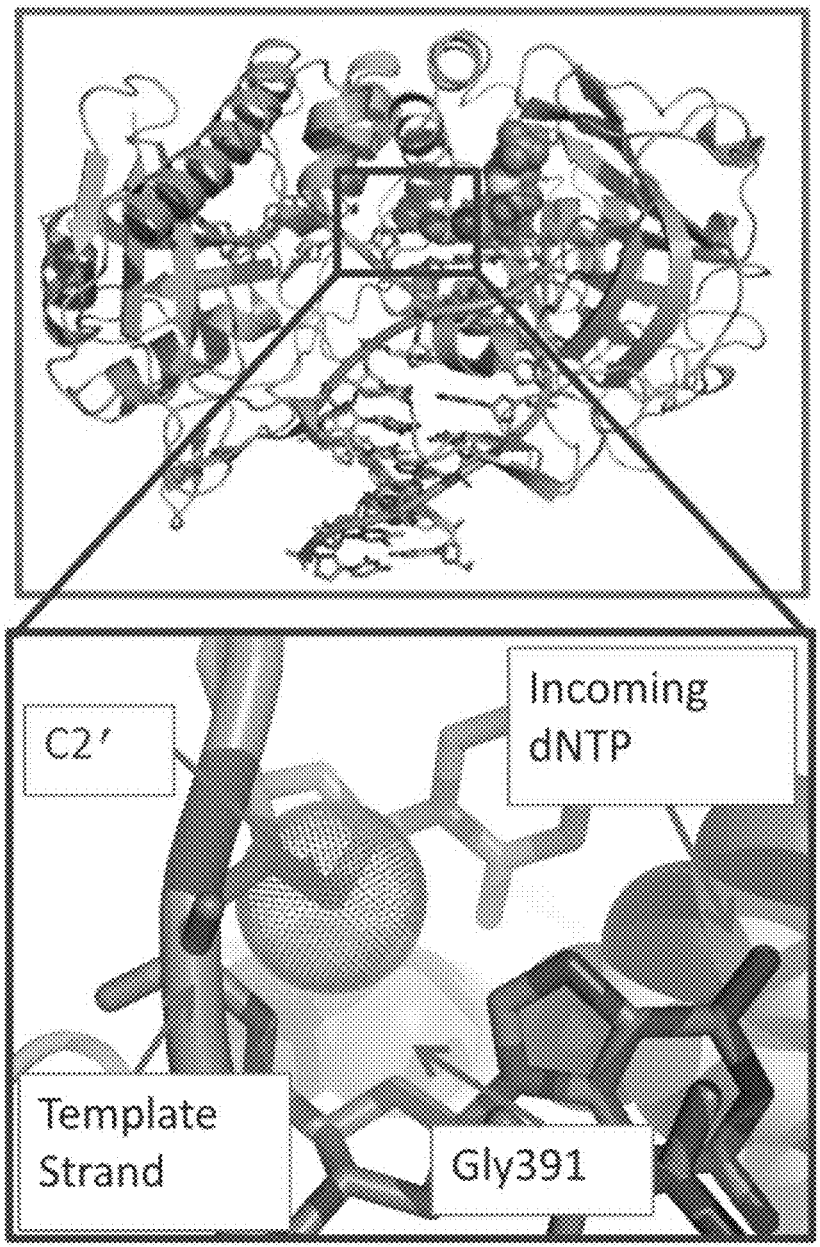
FIG. 1A shows a model of a complex between a Φ29 polymerase and duplex DNA.
FIG. 1B shows a view of the complex in the vicinity of G391.

Schematic figures are not necessarily to scale.

Definitions

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a protein" includes a plurality of proteins, reference to "a cell" includes mixtures of cells, and the like.

The term "about" as used herein indicates the value of a given quantity varies by +/−10% of the value, or optionally +/−5% of the value, or in some embodiments, by +/−1% of the value so described.

The term "nucleic acid" or "polynucleotide" encompasses any physical string of monomer units that can be corresponded to a string of nucleotides, including a polymer of nucleotides (e.g., a typical DNA or RNA polymer), PNAs, modified oligonucleotides (e.g., oligonucleotides comprising nucleotides that are not typical to biological RNA or DNA, such as 2'-O-methylated oligonucleotides), and the like. A nucleic acid can be e.g., single-stranded or double-stranded. Unless otherwise indicated, a particular nucleic acid sequence of this invention encompasses complementary sequences, in addition to the sequence explicitly indicated.

A "polypeptide" is a polymer comprising two or more amino acid residues (e.g., a peptide or a protein). The polymer can additionally comprise non-amino acid elements such as labels, quenchers, blocking groups, or the like and can optionally comprise modifications such as glycosylation, biotinylation, or the like. The amino acid residues of the polypeptide can be natural or non-natural and can be unsubstituted, unmodified, substituted or modified.

An "amino acid sequence" is a polymer of amino acid residues (a protein, polypeptide, etc.) or a character string representing an amino acid polymer, depending on context.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

Numbering of a given amino acid or nucleotide polymer "corresponds to numbering of" or is "relative to" a selected amino acid polymer or nucleic acid when the position of any given polymer component (amino acid residue, incorporated nucleotide, etc.) is designated by reference to the same residue position in the selected amino acid or nucleotide polymer, rather than by the actual position of the component in the given polymer. Similarly, identification of a given position within a given amino acid or nucleotide polymer is "relative to" a selected amino acid or nucleotide polymer when the position of any given polymer component (amino acid residue, incorporated nucleotide, etc.) is designated by reference to the residue name and position in the selected amino acid or nucleotide polymer, rather than by the actual name and position of the component in the given polymer. Correspondence of positions is typically determined by aligning the relevant amino acid or polynucleotide sequences. For example, residue K221 of wild-type M2Y polymerase (SEQ ID NO:2) is identified as position Y224 relative to wild-type Φ29 polymerase (SEQ ID NO:1). Similarly, residue L138 of wild-type M2Y polymerase (SEQ ID NO:2) is identified as position V141 relative to wild-type Φ29 polymerase (SEQ ID NO:1), and an L138K substitution in the M2Y polymerase is thus identified as a V141K substitution relative to SEQ ID NO:1.

The term "recombinant" indicates that the material (e.g., a nucleic acid or a protein) has been artificially or synthetically (non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is, e.g., a polypeptide or protein which is produced by expression of a recombinant nucleic acid.

A "Φ29-type DNA polymerase" (or "phi29-type DNA polymerase") is a DNA polymerase from the Φ29 phage or from one of the related phages that, like Φ29, contain a terminal protein used in the initiation of DNA replication. Φ29-type DNA polymerases are homologous to the Φ29 DNA polymerase (e.g., as listed in SEQ ID NO:1); examples include the B103, GA-1, PZA, Φ15, BS32, M2Y (also known as M2; e.g., as listed in SEQ ID NO:2), Nf, G1, Cp-1, PRD1, PZE, SF5, Cp-5, Cp-7, PR4, PR5, PR722, L17, and AV-1 DNA polymerases, as well as chimeras thereof. A modified recombinant Φ29-type DNA polymerase includes one or more mutations relative to naturally-occurring wild-type Φ29-type DNA polymerases, for example, one or more mutations that increase stability, increase readlength, alter interaction with and/or incorporation of nucleotide analogs, enhance accuracy, increase phototolerance, and/or alter another polymerase property, and may include additional alterations or modifications over the wild-type Φ29-type DNA polymerase, such as one or more deletions, insertions, and/or fusions of additional peptide or protein sequences (e.g., for immobilizing the polymerase on a surface or otherwise tagging the polymerase enzyme).

A "polymerase" is an enzyme that synthesizes a polymer of nucleotides. A polymerase can be, e.g., an RNA-directed polymerase that produces a polynucleotide complementary to an RNA template strand using base-pairing interactions, a DNA-directed polymerase that produces a polynucleotide complementary to a DNA template strand using base-pairing interactions, an RNA polymerase that produces an RNA product strand, and/or a DNA polymerase that produces an DNA product strand (e.g., a DNA-directed DNA polymerase, an RNA-directed DNA polymerase, etc.).

A "reverse transcriptase" is an enzyme that can be used to generate complementary DNA (cDNA) from an RNA template, a process termed "reverse transcription."

A variety of additional terms are defined or otherwise characterized herein.

DETAILED DESCRIPTION

Sequencing RNA templates directly, without first requiring their conversion to cDNAs, makes determining the sequences of large numbers of RNAs faster and more convenient. It can also improve accuracy of the sequences determined, since reverse transcriptase often misincorporates nucleotides while producing cDNAs, and if these misincorporation events are not identified they can be misinterpreted as point mutations or variations in the original sequences. Transcript (or other RNA) abundance can be directly assessed by direct sequencing, without the bias potentially introduced by reverse transcription prior to sequencing. Direct RNA sequencing has been described, e.g., in U.S. Pat. No. 8,501,405 and Vilfan et al. (2013) "Analysis of RNA base modification and structural rearrangement by single-molecule real-time detection of reverse transcription" Journal of Nanobiotechnology 11:8 doi: 10.1186/1477-3155-11-8, each of which is incorporated by reference herein in its entirety for all purposes.

In addition, direct sequencing of RNA can provide information about base modification and RNA secondary structure, which are common in many RNAs, important for function, and lost upon conversion to cDNAs. Detection of RNA base modifications and secondary structure in conjunction with direct sequencing has been described, e.g., in Vilfan et al. supra (previously incorporated by reference in its entirety) and in US patent application publication 2011-0183320, incorporated by reference herein in its entirety for all purposes.

Direct RNA sequencing, including base modification and secondary structure detection, is facilitated by the provision of improved recombinant polymerases as described herein. Among other aspects, the present invention provides new RNA-dependent recombinant polymerases. A recombinant polymerase of the invention, e.g., a recombinant Φ29-type DNA polymerase or a recombinant reverse transcriptase, typically has RNA-dependent DNA polymerase activity and includes one or more mutations (e.g., amino acid substitutions, deletions, or insertions) as compared to a reference polymerase, e.g., a wild-type Φ29-type polymerase or a wild-type reverse transcriptase. Depending on the particular mutation or combination of mutations, the polymerase exhibits one or more properties that find use in, e.g., single molecule sequencing applications or nucleic acid amplification. Such polymerases incorporate nucleotides and/or nucleotide analogs, for example, dye labeled phosphate labeled analogs, into a growing template copy. These polymerases are modified such that they have one or more desirable properties, for example, improved sequencing performance with nucleotide analogs (e.g., labeled phospholinked analogs), increased template-polymerase stability or processivity, increased readlength, increased thermostability, increased resistance to photodamage, decreased branching fraction formation when incorporating the relevant analogs (or, in certain embodiments, increased branching fraction), reduced exonuclease activity, increased yield, altered cofactor selectivity, improved accuracy, increased or decreased speed, and/or altered kinetic properties (e.g., a reduction in the rate of one or more steps of the polymerase kinetic cycle, resulting from, e.g., enhanced interaction of the polymerase with nucleotide analog, enhanced metal coordination, etc.) as compared to a corresponding wild-type or other parental polymerase (e.g., a polymerase from which the modified recombinant polymerase of the invention was derived, e.g., by mutation), as well as other features that will become apparent upon a complete review of the present disclosure. The polymerases of the invention can also include any of the additional features for improved specificity, processivity, retention time, surface stability, analog incorporation, and/or the like noted herein. The polymerases can include one or more exogenous or heterologous features, e.g., at the N- and/or C-terminal regions of the polymerase. Such features find use not only for purification of the recombinant polymerase and/or immobilization of the polymerase to a substrate, but can also alter one or more properties of the polymerase.

These new polymerases are particularly well suited to nucleic acid amplification and/or sequencing applications, particularly sequencing protocols that include detection in real time of the incorporation of labeled analogs into DNA amplicons. As a few examples, increased readlength can produce longer sequence reads including full length RNA sequences, increased phototolerance can prolong useful life of the polymerase under assay conditions, and altered rates, reduced or eliminated exonuclease activity, decreased branching fraction, improved complex stability, altered metal cofactor selectivity, or the like can facilitate discrimination of nucleotide incorporation events from non-incorporation events such as transient binding of a mismatched nucleotide in the active site of the complex, improve processivity, and/or facilitate detection of incorporation events.

Design and Characterization of Recombinant Polymerases

In addition to methods of using the polymerases and other compositions herein, the present invention also includes methods of making the polymerases. Polymerases made by the methods are also a feature of the invention, and it will be evident that, although various design strategies are detailed herein, no limitation of the resulting polymerases to any particular mechanism is thereby intended. As described, methods of making a recombinant polymerase can include structurally modeling a parental polymerase, e.g., using any available crystal structure and molecular modeling software or system. Based on the modeling, one or more amino acid residue positions in the polymerase are identified as targets for mutation. For example, one or more feature affecting binding of a DNA or RNA template, binding of a nucleotide analog, stability (e.g., thermostability of the free polymerase, binary complex stability, and/or ternary complex stability), phototolerance, closed complex stability, nucleotide access to or removal from the active site (and, thereby, branching), product binding, etc. is identified. These residues can be, e.g., in the active site or a binding pocket or in a domain such as the exonuclease, TPR2 or thumb domain (or interface between domains) or proximal to such domains. The polymerase is mutated to include different residues at such positions (e.g., another one of the nineteen other commonly occurring natural amino acids or a non-natural amino acid, e.g., a nonpolar and/or aliphatic residue, a polar uncharged residue, an aromatic residue, a positively charged residue, or a negatively charged residue), and then screened for an activity of interest (e.g., ability to employ an RNA template, analog incorporation, processivity, stability (e.g., thermostability of the free polymerase, binary complex stability, and/or ternary complex stability), readlength, sensitivity to base modification, phototolerance, $k_{off}$, $K_d$, branching fraction, decreased rate constant, balanced rate constants, accuracy, speed, yield, cofactor selectivity, cosolvent resistance, etc.). It will be evident that catalytic and/or highly conserved residues are typically (but not necessarily) less preferred targets for mutation.

Further, a mutated polymerase can be further modified to enhance the properties of the polymerase. For example, a polymerase comprising a combination of desirable mutations can be mutated at one or more additional sites to enhance a property already possessed by the polymerase or to confer a new property not provided by the existing mutations. Details correlating polymerase structure with desirable functionalities that can be added to polymerases of the invention are provided herein. Also provided below are various approaches for modifying/mutating polymerases of the invention, determining kinetic parameters or other properties of the modified polymerases, screening modified polymerases, and adding exogenous features to the N- and/or C-terminal regions of the polymerases.

Structure-Based Design of Recombinant Polymerases

Structural data for a polymerase can be used to conveniently identify amino acid residues as candidates for mutagenesis to create recombinant polymerases, for example, having modified active site regions and/or modified domain interfaces to increase polymerase stability, improve complex stability, increase readlength, increase phototolerance, reduce reaction rates, reduce branching, reduce exonuclease activity, alter cofactor selectivity, improve yield, or confer other desirable properties. For example, analysis of the three-dimensional structure of a polymerase such as Φ29 or HIV reverse transcriptase can identify residues that are in the active polymerization site of the enzyme, residues that form the template binding site, residues that form part of the nucleotide analog binding pocket, and/or amino acids at an interface between domains.

The three-dimensional structures of a large number of polymerases have been determined by x-ray crystallography and nuclear magnetic resonance (NMR) spectroscopy, including the structures of polymerases with bound templates, nucleotides, and/or nucleotide analogs. Many such structures are freely available for download from the Protein Data Bank, at (www(dot)rcsb(dot)org/pdb. Structures, along with domain and homology information, are also freely available for search and download from the National Center for Biotechnology Information's Molecular Modeling DataBase, at www(dot)ncbi(dot)nlm(dot)nih(dot)gov/Structure/MMDB/mmdb(dot)shtml. The structures of Φ29 polymerase, Φ29 polymerase complexed with terminal protein, and Φ29 polymerase complexed with primer-template DNA in the presence and absence of a nucleoside triphosphate are available; see Kamtekar et al. (2004) "Insights into strand displacement and processivity from the crystal structure of the protein-primed DNA polymerase of bacteriophage Φ29" Mol. Cell 16(4): 609-618), Kamtekar et al. (2006) "The phi29 DNA polymerase:protein-primer structure suggests a model for the initiation to elongation transition" EMBO J. 25(6):1335-43, and Berman et al. (2007) "Structures of phi29 DNA polymerase complexed with substrate: The mechanism of translocation in B-family polymerases" EMBO J. 26:3494-3505, respectively. Numerous structures of HIV reverse transcriptase, including complexes with templates and/or inhibitors, are available. See, e.g., Huang et al. (1998) "Structure of a covalently trapped catalytic complex of HIV-1 reverse transcriptase: implications for drug resistance" Science 282:1669-75, Kohlstaedt et al. (1992) "Crystal structure at 3.5 A resolution of HIV-1 reverse transcriptase complexed with an inhibitor" Science 256: 1783-1790, Jacobo-Molina et al. (1993) "Crystal structure of human immunodeficiency virus type 1 reverse transcriptase complexed with double-stranded DNA at 3.0 A resolution shows bent DNA" Proc Natl Acad Sci USA: 90:6320-6324, Sarafianos et al. (2001) "Crystal structure of HIV-1 reverse transcriptase in complex with a polypurine tract RNA:DNA" Embo J. 20:1449-1461, Sarafianos et al. (2002) "Structures of HIV-1 reverse transcriptase with pre- and post-translocation AZTMP-terminated DNA" Embo J. 21:6614-6624, Ding et al. (1998) "Structure and functional implications of the polymerase active site region in a complex of HIV-1 RT with a double-stranded DNA template-primer and an antibody Fab fragment at 2.8 A resolution" J Mol Biol. 284: 1095-1111, Ren et al. (1995) "High resolution structures of HIV-1 RT from four RT-inhibitor complexes" Nat Struct Biol. 2:293-302, Rodgers et al. (1995) "The structure of unliganded reverse transcriptase from the human immunodeficiency virus type 1" Proc Natl Acad Sci USA 92:1222-1226, and Hsiou et al. (1996) "Structure of unliganded HIV-1 reverse transcriptase at 2.7 A resolution: implications of conformational changes for polymerization and inhibition mechanisms" Structure 4:853-860. The structures of additional polymerases or complexes can be modeled, for example, based on homology of the polymerases with polymerases whose structures have already been determined. Alternatively, the structure of a given polymerase (e.g., a wild-type or modified polymerase), optionally complexed with a DNA or RNA (e.g., template and/or primer) and/or nucleotide analog, or the like, can be determined.

Techniques for crystal structure determination are well known. See, for example, McPherson (1999) *Crystallization of Biological Macromolecules* Cold Spring Harbor Laboratory; Bergfors (1999) *Protein Crystallization* International University Line; Mullin (1993) *Crystallization* Butterwoth-Heinemann; Stout and Jensen (1989) *X-ray structure determination: a practical guide,* 2nd Edition Wiley Publishers, New York; Ladd and Palmer (1993) *Structure determination by X-ray crystallography,* 3rd Edition Plenum Press, New York; Blundell and Johnson (1976) *Protein Crystallography* Academic Press, New York; Glusker and Trueblood (1985) *Crystal structure analysis: A primer,* 2nd Ed. Oxford University Press, NewYork; *International Tables for Crystallography, Vol. F. Crystallography of Biological Macromolecules*; McPherson (2002) *Introduction to Macromolecular Crystallography* Wiley-Liss; McRee and David (1999) *Practical Protein Crystallography,* Second Edition Academic Press; Drenth (1999) *Principles of Protein X-Ray Crystallography* (Springer Advanced Texts in Chemistry) Springer-Verlag; Fanchon and Hendrickson (1991) Chapter 15 of *Crystallographic Computing, Volume* 5 IUCr/Oxford University Press; Murthy (1996) Chapter 5 of *Crystallographic Methods and Protocols* Humana Press; Dauter et al. (2000) "Novel approach to phasing proteins: derivatization by short cryo-soaking with halides" Acta Cryst.D56:232-237; Dauter (2002) "New approaches to high-throughput phasing" Curr. Opin. Structural Biol. 12:674-678; Chen et al. (1991) "Crystal structure of a bovine neurophysin-II dipeptide complex at 2.8 Å determined from the single-wavelength anomalous scattering signal of an incorporated iodine atom" Proc. Natl Acad. Sci. USA, 88:4240-4244; and Gavira et al. (2002) "*Ab initio* crystallographic structure determination of insulin from protein to electron density without crystal handling" Acta Cryst.D58:1147-1154.

In addition, a variety of programs to facilitate data collection, phase determination, model building and refinement, and the like are publicly available. Examples include, but are not limited to, the HKL2000 package (Otwinowski and Minor (1997) "Processing of X-ray Diffraction Data Collected in Oscillation Mode" Methods in Enzymology 276:307-326), the CCP4 package (Collaborative Computational Project (1994) "The CCP4 suite: programs for protein crystallography" Acta Crystallogr D 50:760-763), SOLVE and RESOLVE (Terwilliger and Berendzen (1999) Acta Crystallogr D 55 (Pt 4):849-861), SHELXS and SHELXD (Schneider and Sheldrick (2002) "Substructure solution with SHELXD" Acta Crystallogr D Biol Crystallogr 58:1772-1779), Refmac5 (Murshudov et al. (1997) "Refinement of Macromolecular Structures by the Maximum-Likelihood Method" Acta Crystallogr D 53:240-255), PRODRG (van Aalten et al. (1996) "PRODRG, a program for generating molecular topologies and unique molecular descriptors from coordinates of small molecules" J Comput Aided Mol Des 10:255-262), and Coot (Elmsley et al. (2010) "Features and Development of Coot" Acta Cryst D 66:486-501.

Techniques for structure determination by NMR spectroscopy are similarly well described in the literature. See, e.g., Cavanagh et al. (1995) *Protein NMR Spectroscopy: Principles and Practice*, Academic Press; Levitt (2001) *Spin Dynamics: Basics of Nuclear Magnetic Resonance*, John Wiley & Sons; Evans (1995) *Biomolecular NMR Spectroscopy*, Oxford University Press; Wüthrich (1986) *NMR of Proteins and Nucleic Acids* (Baker Lecture Series), Kurt Wiley-Interscience; Neuhaus and Williamson (2000) *The Nuclear Overhauser Effect in Structural and Conformational Analysis*, 2nd Edition, Wiley-VCH; Macomber (1998) *A Complete Introduction to Modern NMR Spectroscopy*, Wiley-Interscience; Downing (2004) *Protein NMR Techniques* (Methods in Molecular Biology), 2nd edition, Humana Press; Clore and Gronenborn (1994) *NMR of Proteins* (Topics in Molecular and Structural Biology), CRC Press; Reid (1997) *Protein NMR Techniques*, Humana Press; Krishna and Berliner (2003) *Protein NMR for the Millenium* (Biological Magnetic Resonance), Kluwer Academic Publishers; Kiihne and De Groot (2001) *Perspectives on Solid State NMR in Biology* (Focus on Structural Biology, 1), Kluwer Academic Publishers; Jones et al. (1993) *Spectroscopic Methods and Analyses: NMR, Mass Spectrometry, and Related Techniques* (Methods in Molecular Biology, Vol. 17), Humana Press; Goto and Kay (2000) Curr. Opin. Struct. Biol. 10:585; Gardner (1998) Annu. Rev. Biophys. Biomol. Struct. 27:357; Wüthrich (2003) Angew. Chem. Int. Ed. 42:3340; Bax (1994) Curr. Opin. Struct. Biol. 4:738; Pervushin et al. (1997) Proc. Natl. Acad. Sci. U.S.A. 94:12366; Fiaux et al. (2002) Nature 418:207; Fernandez and Wider (2003) Curr. Opin. Struct. Biol. 13:570; Ellman et al. (1992) J. Am. Chem. Soc. 114:7959; Wider (2000) BioTechniques 29:1278-1294; Pellecchia et al. (2002) Nature Rev. Drug Discov. (2002) 1:211-219; Arora and Tamm (2001) Curr. Opin. Struct. Biol. 11:540-547; Flaux et al. (2002) Nature 418:207-211; Pellecchia et al. (2001) J. Am. Chem. Soc. 123:4633-4634; and Pervushin et al. (1997) Proc. Natl. Acad. Sci. USA 94:12366-12371.

The structure of a polymerase or of a polymerase bound to a DNA or RNA or with a given nucleotide analog incorporated into the active site can, as noted, be directly determined, e.g., by x-ray crystallography or NMR spectroscopy, or the structure can be modeled based on the structure of the polymerase and/or a structure of a polymerase with a natural nucleotide bound. The active site or other relevant domain of the polymerase can be identified, for example, by homology with other polymerases, examination of polymerase-template or polymerase-nucleotide co-complexes, biochemical analysis of mutant polymerases, and/or the like. The position of a nucleotide analog (as opposed to an available nucleotide structure) in the active site can be modeled, for example, by projecting the location of non-natural features of the analog (e.g., additional phosphate or phosphonate groups in the phosphorus containing chain linked to the nucleotide, e.g., tetra, penta or hexa phosphate groups, detectable labeling groups, e.g., fluorescent dyes, or the like) based on the previously determined location of another nucleotide or nucleotide analog in the active site.

Such modeling of the nucleotide analog or template (or both) in the active site can involve simple visual inspection of a model of the polymerase, for example, using molecular graphics software such as the PyMOL viewer (open source, freely available on the World Wide Web at www(dot)pymol (dot)org), Insight II, or Discovery Studio 2.1 (commercially available from Accelrys at (www (dot) accelrys (dot) com/products/discovery-studio). Alternatively, modeling of the active site complex of the polymerase or a putative mutant polymerase, for example, can involve computer-assisted docking, molecular dynamics, free energy minimization, and/or like calculations. Such modeling techniques have been well described in the literature; see, e.g., Babine and Abdel-Meguid (eds.) (2004) *Protein Crystallography in Drug Design*, Wiley-VCH, Weinheim; Lyne (2002) "Structure-based virtual screening: An overview" Drug Discov. Today 7:1047-1055; Molecular Modeling for Beginners, at (www (dot) usm (dot) maine (dot) edu/~rhodes/SPVTut/index (dot) html; and Methods for Protein Simulations and Drug Design at (www (dot) dddc (dot) ac (dot) cn/embo04; and references therein. Software to facilitate such modeling is widely available, for example, the CHARMm simulation package, available academically from Harvard University or commercially from Accelrys (at www (dot) accelrys (dot) com), the Discover simulation package (included in Insight II, supra), and Dynama (available at (www(dot) cs (dot) gsu (dot) edu/~cscrwh/progs/progs (dot) html). See also an extensive list of modeling software at (www (dot) netsci (dot) org/Resources/Software/Modeling/MMMD/top (dot) html.

Visual inspection and/or computational analysis of a polymerase model, including optional comparison of models of the polymerase in different states, can identify relevant features of the polymerase, including, for example, residues that can be mutated to alter interaction with and/or incorporation of nucleotide analogs, increase processivity, or increase readlength. Amino acid sequence data, e.g., for members of a family of polymerases, can be used in conjunction with structural data to identify particular residues as candidates for mutagenesis.

Engineering Φ29 DNA Polymerase to Increase RT Activity

In one aspect, the polymerase that is modified is a Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204. Similarly, the modified recombinant DNA polymerase can be homologous to another Φ29-type DNA polymerase, such as B103, GA-1, PZA, Φ15, BS32, M2Y (also known as M2), Nf, G1, Cp-1, PRD1, PZE, SF5, Cp-5, Cp-7, PR4, PR5, PR722, L17, AV-1, Φ21, or the like. For nomenclature, see also, Meijer et al. (2001) "Φ29 Family of Phages" Microbiology and Molecular Biology Reviews, 65(2):261-287. See, e.g., SEQ ID NO:1 for the amino acid sequence of wild-type Φ29 polymerase and SEQ ID NO:2 for the amino acid sequence of wild-type M2Y polymerase.

In addition to wild-type polymerases, chimeric polymerases made from a mosaic of different sources can be used. For example, Φ29-type polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, a M2 polymerase, a B103 polymerase, and a GA-1 polymerase, can be generated. Appropriate mutations to enhance performance with nucleotide analogs, increase readlength, improve thermostability, and/or alter another desirable property as described herein can be introduced into the chimeras.

Φ29-type DNA polymerases typically accept DNA templates. However, work at Pacific Biosciences has shown that a recombinant Φ29 polymerase can read through short stretches of RNA. Various mutations to enhance Φ29 polymerase's ability to accept an RNA template can be introduced into Φ29 polymerase, effectively converting the polymerase into a reverse transcriptase. Benefits of using a Φ29 polymerase having reverse transcriptase activity include the high processivity of Φ29 and its strand displacement activity, which permits it to read through regions of secondary structure. Numerous Φ29-type polymerases optimized for use with fluorescently labeled analogs useful in single molecule sequencing are also known (see, e.g., US patent application publications 2007-0196846, 2008-0108082, 2010-0075332, 2010-0093555, 2010-0112645, 2011-0189659, 2012-0034602, 2013-0217007, 2014-0094374, and 2014-0094375, each of which is incorporated herein by reference in its entirety for all purposes) and can be mutated to produce an effective reverse transcriptase. Although the following discussion centers on Φ29 polymerase, it will be evident that the noted mutations can be introduced into another Φ29-type polymerase (e.g., into an M2, B103, or other polymerase homologous to Φ29) to produce a recombinant polymerase having the desired reverse transcriptase activity. Rationales for mutating various positions are presented, but no limitation to any particular mechanism is intended.

Figure 5A:
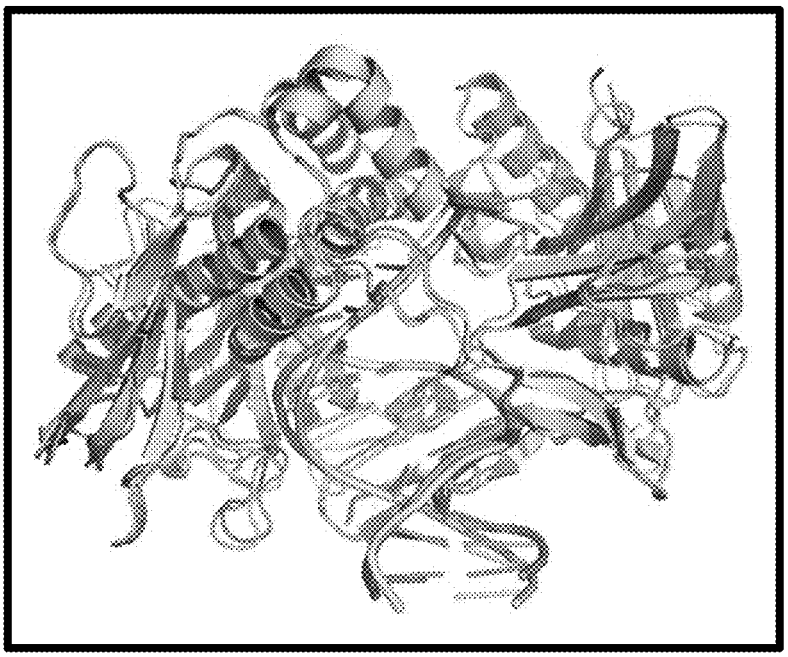
FIG. 5A shows a superposition of the structures of a complex containing a Φ29 polymerase, primer, and incoming nucleotide analog with either a DNA template (cyan) or an RNA template (yellow).
Figure 5B:
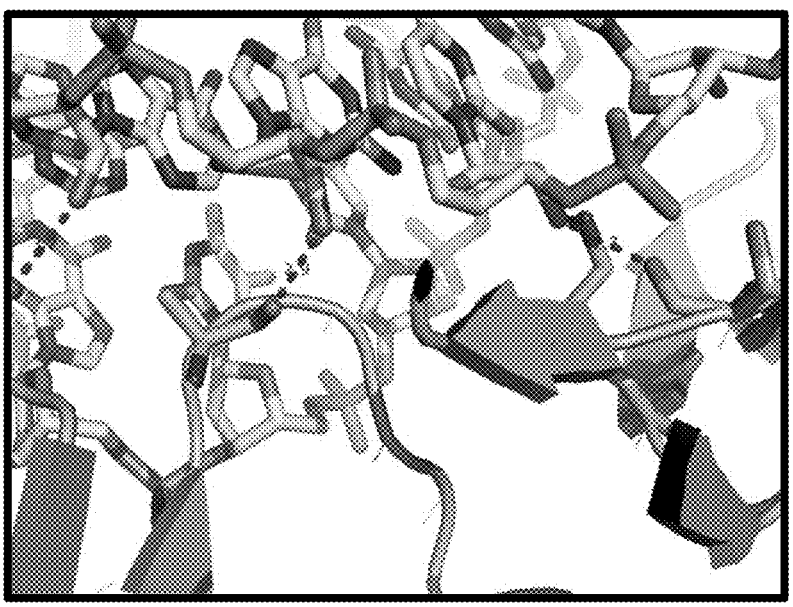
FIG. 5B shows multiple hydrogen bonds formed between the polymerase and template 2' hydroxyl groups in the crystal structure of a Φ29 polymerase/RNA template/DNA primer/incoming phosphate-labeled hexaphosphate dG nucleotide analog.

There are two challenges inherent in converting Φ29 DNA polymerase into a reverse transcriptase. First, the DNA duplex typically bound by the polymerase is predominantly B form, while an RNA:DNA heteroduplex generally assumes a conformation closer to a canonical A form double helix. Residues that interact with the heteroduplex are therefore targeted for mutation. Such residues can be identified, e.g., from a structure of a Φ29 polymerase/DNA template/primer complex and/or a structure of a Φ29 polymerase/RNA template/primer complex (see, e.g., FIGS. 5A and 5B). Positions that can be mutated include, e.g., M97, Y101, P129, S192, K305, R306, R308, L416, R496, Q497, T499, T534, K557, D570, T571, T573, and/or K575. Exemplary substitutions that can modulate DNA/RNA heteroduplex binding include, e.g., M97L, M97A, M97K, M97E, M97R, Y101F, P129R, S192A, K305R, R306Q, R306A, R306F, R306H, R306K, R306L, R306T, R308L, R308A, R308H, R308K, R308P, R308Q, L416A, L416E, L416H, L416I, L416S, L416T, L416Q, L416V, L416K, R496K, Q497R, Q497K, T499S, T499A, T499V, T499I, T499N, T534P, K557R, D570S, D570E, D570M, D570N, D570T, T571V, T571P, T573A, T573S, T573K, and/or K575R.

Figure 1C:
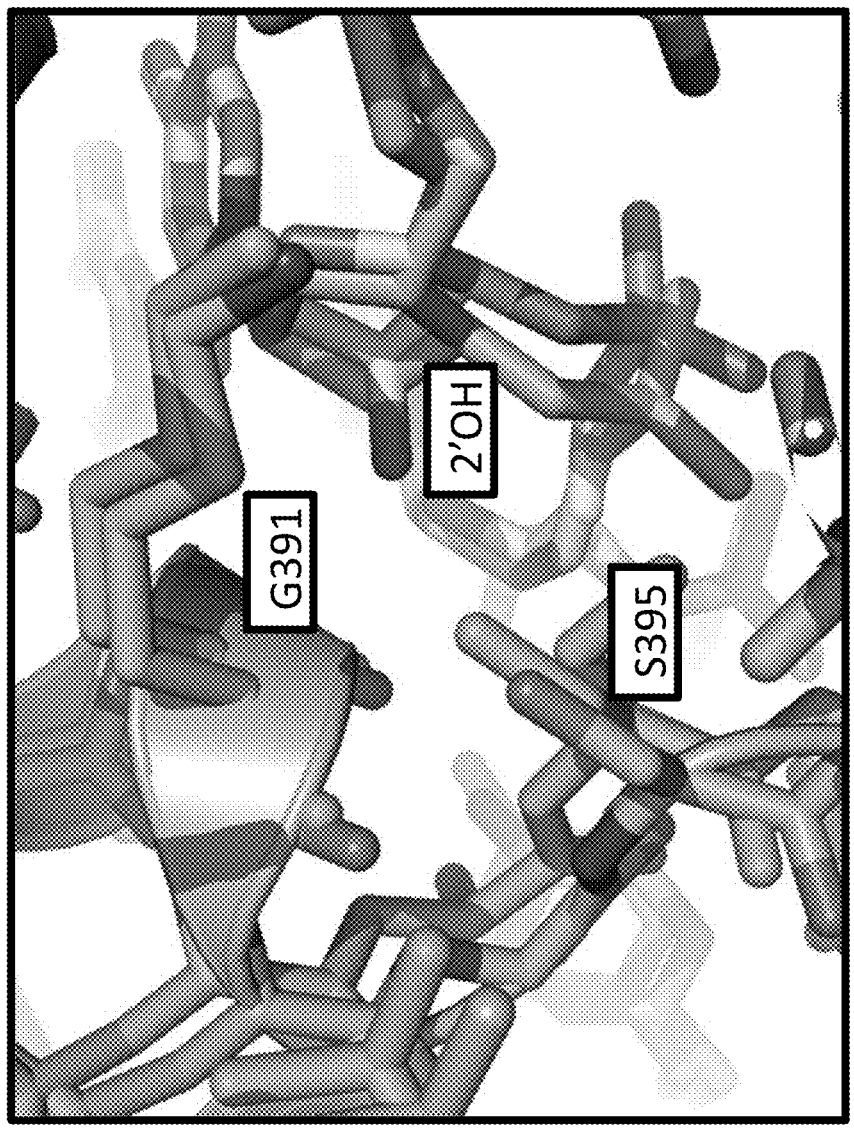
FIG. 1C shows a view in the vicinity of G391 of a superposition of the structures of a complex containing a Φ29 polymerase, primer, and incoming nucleotide analog with either a DNA template (cyan) or an RNA template (yellow/salmon).

Second, structural analysis suggests a clash between a template 2' OH moiety and the polymerase. Relief of this clash can increase Φ29 polymerase's activity on RNA templates. A model of a complex between a Φ29 polymerase and duplex DNA is shown in FIG. 1A. A view in the vicinity of G391 in this complex is shown in FIG. 1B; C2' of the residue in the templating position is highlighted to illustrate that the pocket can be redesigned to more favorably accommodate a 2' hydroxyl group. Mutations are therefore introduced into Φ29 polymerase to open a pocket around the C2' position of the templating base, close to G391, to create space for the 2' hydroxyl. FIG. 1C shows a view in the vicinity of G391 in a superposition of the structures of a complex containing a Φ29 polymerase, primer, and incoming nucleotide analog with either a DNA template (cyan) or an RNA template (yellow/salmon), illustrating accommodation of a templating RNA base in the active site by conformational changes in the polymerase. Such conformational changes can be facilitated by mutation of various residues. Residues that can be mutated to better accommodate an RNA template include, e.g., L389, Y390, G391, K392, F393, A394, S395, F363, and/or F198Y. Exemplary substitutions include, e.g., L389A, L389V, L389C, L389I, Y390F, Y390P, Y390H, Y390V, Y390L, K392A, K392R, K392H, F393L, F393A, F393V, A394, S395A, S395T, S395G, F363L, F363V, F363W, F363A, and/or F198Y.

Mutations that reduce or eliminate the endogenous exonuclease activity of Φ29 polymerase can increase reverse transcriptase activity. Residues that can be mutated include, e.g., D12, T17, N62, D66, and/or Y148. Exemplary substitutions include, e.g., D12A, T17W, N62D, D66A, and/or Y148I. See also the section entitled "Exonuclease-Deficient Recombinant Polymerases" hereinbelow. Mutations that increase cognate base affinity in the active site can be beneficial for reverse transcriptase activity. Residues that can be mutated include, e.g., L253 and/or A437. Exemplary substitutions include, e.g., L253A and/or A437G. In particular, combination of mutations that increase cognate base affinity (e.g., L253A and/or A437G) with mutations that inhibit primer strand binding to the exonuclease domain (e.g., T17W and/or Y148I) can increase reverse transcriptase activity.

Additional residues that can be mutated to increase reverse transcriptase activity of Φ29 polymerase include, e.g., T441 and T421. Exemplary substitutions include, e.g., T441L and T421Y (which can improve readlength).

Processivity of recombinant Φ29 polymerase, particularly on an RNA template, can be increased by locking the template in place in the enzyme with chemical cross-links. For example, a bifunctional cross-linker can be reacted with residues in the polymerase on each side of the bound template, topologically encircling the template. Cysteine residues can be introduced into the polymerase at suitable positions for cross-link formation. Thus, the polymerase can include, e.g., A83C and E420C substitutions, D84C and E418C substitutions, V19C and N409C substitutions, and/or N409C and V568C substitutions. Existing solvent accessible cysteine residues can be mutated to ensure that the cross-link is formed between the desired pair of residues; thus, the polymerase can also include one or more substitutions such as, e.g., C106S and/or C448V. Suitable bifunctional linkers are known in the art, for example, a bismaleimide linker, e.g., a bismaleimide-PEG linker, e.g., 1,11-bismaleimido-triethyleneglycol (BM(PEG)$_3$). Other coupling chemistries that can be employed include, e.g., thiol reactive reagents and disulfide containing reagents, e.g., haloacetyl cross-linkers (e.g., linkers including two iodoacetyl/iodoacet-amide or bromoacetyl groups) and linkers with two pyridyl disulfide groups. The body of the linker can include, e.g., PEG (polyethylene glycol), an oligopeptide (e.g., polyglycine), or the like. Optimal linker length can be chosen based on the distance between the two residues to be cross-linked, e.g., in a crystal structure or other model of the polymerase. The linker is typically reacted with the polymerase after binding of the template (or primer/template); suitable reaction conditions for various linker chemistries are known in the art. Noncovalent linkers can also be employed. Optionally, the linker has additional functionality. For example, a trifunctional linker can be employed, with two of the groups being used to cross-link two residues in the polymerase and the third group being used for addition of a polynucleotide binding moiety (e.g., to increase readlength) or of a biotin or other group to facilitate immobilization of the polymerase on a surface.

Figure 2:
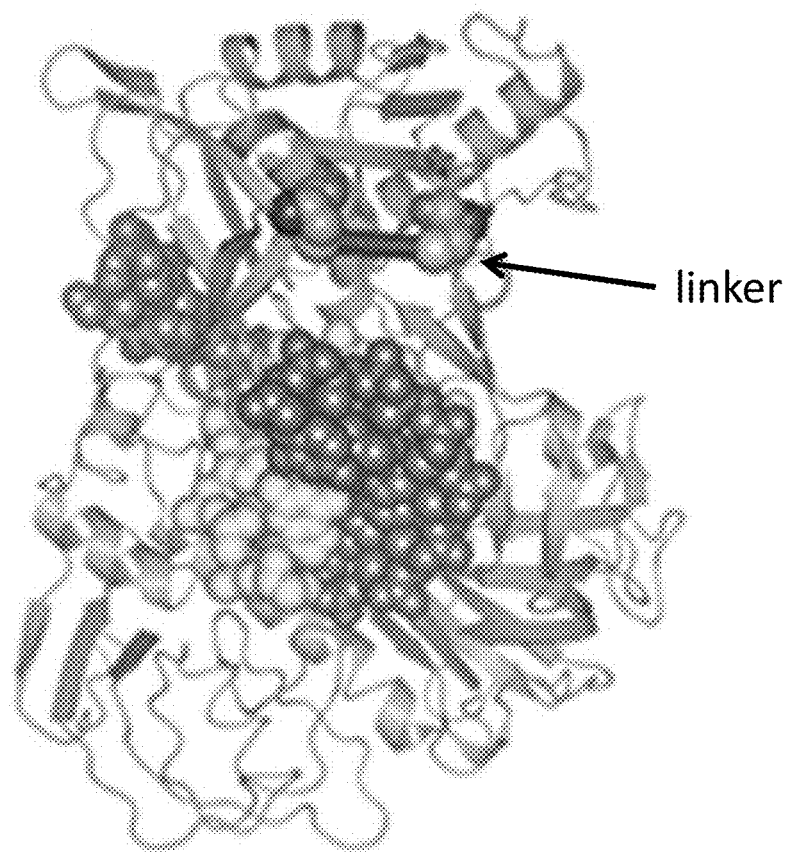
FIG. 2 shows a model of a recombinant Φ29 polymerase including V19C and N409C substitutions topologically locked around template by reaction of a bifunctional linker with the two cysteines.

A model of a recombinant Φ29 polymerase including V19C and N409C substitutions topologically locked around template by reaction of a bifunctional linker with the two cysteines is shown in FIG. 2. Topological encirclement of the template by polymerase is particularly effective for circular templates (including, e.g., simple circles and SMRT-bells™ as described in, e.g., U.S. Pat. No. 8,153,375 "Compositions and Methods for Nucleic Acid Sequencing" and Travers et al. (2010) Nucl. Acids Res. 38(15):e159, each of which is incorporated herein by reference in its entirety for all purposes). Although described in terms of RNA templates, where dissociation is a greater problem, it will be evident that topological encirclement of a DNA template (linear or circular) by recombinant Φ29 polymerase can also be employed.

Recombinant Φ29 polymerases modified to increase reverse transcriptase activity can exhibit undesirably large interpulse distances in single molecule sequencing reactions. Accordingly, the mutations described herein for increasing RNA-dependent polymerase activity can be favorably combined with mutations that decrease interpulse distance. Residues that can be mutated to decrease interpulse distance include, e.g., K135, T373, E375, D476, and/or K512. Exemplary substitutions include, e.g., K135R, T373F, E375W, D476H, and/or K512H.

Sequencing of an RNA template is optionally performed at higher temperature than is routinely used for sequencing of a DNA template, e.g., to assist in resolving RNA secondary structure. Mutations that enhance thermostability of the polymerase and/or polymerase complex can thus be desirable. Positions relative to a wild-type Φ29 polymerase that can be mutated to increase thermostability of the free polymerase include, e.g., Y224, V250, T368, E508, E515, and/or F526. Exemplary substitutions that can enhance polymerase stability include, e.g., Y224K, V250I, T368F, T368Y, E508R, E515Q, E515K, and F526L. Positions that can be mutated to enhance stability of a binary complex including the polymerase and the nucleic acid substrate include, e.g., A83, Q99, Y148, K131, E420, and D570. Exemplary substitutions that can enhance binary stability include, e.g., Q99I, Y148I, K131E, D570E, D570S, D570T, D570M, D570V, D570W, D570G, and D570C. Additional exemplary substitutions that can increase binary stability include substitutions that introduce a salt bridge, e.g., between positions A83 and E420, e.g., a combination of A83E and E420R, A83D and E420R, A83E and E420K, or A83D and E420K. Positions that can be mutated to increase thermostability of a ternary complex including the polymerase, a nucleic acid substrate, and a cognate nucleotide or nucleotide analog include, e.g., V250, L253, T368, A484, E515, and F526. Exemplary substitutions that can enhance ternary complex stability include, e.g., V250I and L253H, e.g., in combination with A437G, T368V, A484E, E515Q, E515K, and F526L.

The polymerase mutations noted herein can be combined with each other and with essentially any other available mutations and mutational strategies to confer additional improvements in, e.g., performance in single molecule sequencing reactions, ability to incorporate fluorescently labeled phospholinked nucleotide analogs, nucleotide analog specificity, enzyme processivity, yield, thermostability, improved retention time of labeled nucleotides in polymerase-DNA-nucleotide complexes, phototolerance, and/or the like. For example, the mutations and mutational strategies herein can be combined with those taught in, e.g., US patent application publication 2007-0196846 "Polymerases for Nucleotide Analogue Incorporation" by Hanzel et al., US patent application publication 2008-0108082 "Polymerase Enzymes and Reagents for Enhanced Nucleic Acid Sequencing" by Rank et al., US patent application publication 2010-0075332 "Engineering Polymerases and Reaction Conditions for Modified Incorporation Properties" by Pranav Patel et al., US patent application publication 2010-0093555 "Enzymes Resistant to Photodamage" by Keith Bjornson et al., US patent application publication 2010-0112645 "Generation of Modified Polymerases for Improved Accuracy in Single Molecule Sequencing" by Sonya Clark et al., US patent application publication 2011-0189659 "Generation of Modified Polymerases for Improved Accuracy in Single Molecule Sequencing" by Sonya Clark et al., US patent application publication 2012-0034602 "Recombinant Polymerases For Improved Single Molecule Sequencing" by Robin Emig et al., US patent application publication 2013-0217007 "Recombinant Polymerases with Increased Phototolerance" by Satwik Kamtekar et al., US patent application publication 2014-0094374 "Recombinant Polymerases with Increased Readlength and Stability for Single-Molecule Sequencing" by Satwik Kamtekar et al., and US patent application publication 2014-0094375 "Recombinant Polymerases for Incorporation of Protein Shield Nucleotide Analogs" by Satwik Kamtekar et al. Each of these applications is incorporated herein by reference in its entirety for all purposes. This combination of mutations/mutational strategies can be used to impart several simultaneous improvements to a polymerase (e.g., increased reverse transcriptase activity, enhanced utility with desired analogs, improved processivity, increased readlength, increased thermostability, increased phototolerance, decreased branching fraction formation, improved specificity, altered rates, improved retention time, improved stability of the closed complex, tolerance for a particular metal cofactor, etc.). In addition, polymerases can be further modified for application-specific reasons, such as to improve activity of the enzyme when bound to a surface, as taught, e.g., in US patent application publication 2010-0261247 "Active Surface Coupled Polymerases" by Hanzel et al. and US patent application publication 2010-0260465 "Protein Engineering Strategies to Optimize Activity of Surface Attached Proteins" by Hanzel et al. (each of which is incorporated herein by reference in its entirety for all purposes) and/or to include purification or handling tags as is taught in the cited references and as is common in the art. Similarly, the modified polymerases described herein can be employed in combination with other strategies to improve polymerase performance, for example, reaction conditions for controlling polymerase rate constants such as taught in US patent application publication US 2009-0286245 entitled "Two slow-step polymerase enzyme systems and methods," incorporated herein by reference in its entirety for all purposes.

A list of exemplary polymerase mutation combinations, and optional corresponding exogenous features at the C-terminal region of the polymerase, is provided in Table 1. Positions of amino acid substitutions are identified relative to a wild-type Φ29 DNA polymerase (SEQ ID NO:1). Polymerases of the invention (including those provided in Table 1) can include any exogenous or heterologous feature (or combination of such features), e.g., at the N- and/or C-terminal region. For example, some or all of the exogenous features listed in Table 1 can be omitted, or substituted or combined with any of the other exogenous features described herein, and still result in a polymerase of the invention. As will be appreciated, the numbering of amino acid residues is with respect to a particular reference polymerase, such as the wild-type sequence of the Φ29 polymerase (SEQ ID NO:1); actual position of a mutation within a molecule of the invention may vary based upon the nature of the various modifications that the enzyme includes relative to the wild type Φ29 enzyme, e.g., deletions and/or additions to the molecule, either at the termini or within the molecule itself.

TABLE 1

Exemplary mutations introduced into a Φ29 DNA polymerase engineered for RNA sequencing. Positions are identified relative to SEQ ID NO: 1. See, e.g., U.S. patent application publications 2012/0034,602 and 2014/009,4375 for the sequence of BtagV7. The GGGSLVPRGSGGGS linker is listed as SEQ ID NO: 5.

| Mutations | C-terminal region features |
|---|---|
| T17W A68S K135Q L142K Y224K E239G V250I L253A R261K L326V T368S E375Y T421Y W436Y A437G Y439W E466K A484E E508R D510R K512Y E515Q K539E P558A D570E | GGGSLVPRGSGGGS BtagV7 BtagV7 G His10 |
| T17W A68S K135Q L142K Y224K E239G V250I L253A R261K L326V T368S E375Y T421Y W436Y A437G Y439W E466K A484E E508R D510R K512Y E515Q K539E P558A | GGGSLVPRGSGGGS BtagV7 BtagV7 G His10 |
| A68S K135Q L142K Y224K E239G V250I L253A R261K L326V T368S E375Y T421Y W436Y A437G Y439W E466K A484E E508R D510R K512Y E515Q K539E P558A D570E | GGGSLVPRGSGGGS BtagV7 BtagV7 G His10 |
| T17W A68S K135Q L142K Y224K E239G V250I L253A R261K R306Q R308L L326V T368S E375Y T421Y W436Y A437G Y439W E466K A484E E508R D510R K512Y E515Q K539E P558A D570E | GGGSLVPRGSGGGS BtagV7 BtagV7 G His10 |
| T17W A68S K135Q L142K Y224K E239G V250I L253A R261K L326V T368S E375Y T421Y W436Y A437G Y439W E466K A484E E508R D510R K512Y E515Q K539E P558A D570S T571V | GGGSLVPRGSGGGS BtagV7 BtagV7 G His10 |
| T17W A68S K135Q L142K Y224K E239G V250I L253A R261K L326V T368S E375Y T421Y W436Y A437G Y439W E466K D476H A484E E508R D510R K512Y E515Q K539E P558A D570E | GGGSLVPRGSGGGS BtagV7 BtagV7 G His10 |
| T17W A68S K135Q L142K Y224K E239G V250I L253A R261K L326V T368S E375Y T421Y W436Y A437G Y439W E466K A484E E508R D510R K512Y E515Q K539E P558A D570N | GGGSLVPRGSGGGS BtagV7 BtagV7 G His10 |
| T17W A68S K135Q L142K Y224K E239G V250I L253A R261K L326V T368S E375Y T421Y W436Y A437G Y439W E466K A484E E508R D510R K512Y E515Q K539E P558A D570T | GGGSLVPRGSGGGS BtagV7 BtagV7 G His10 |

TABLE 1-continued

Exemplary mutations introduced into a Φ29 DNA polymerase engineered for RNA sequencing. Positions are identified relative to SEQ ID NO: 1. See, e.g., U.S. patent application publications 2012/0034,602 and 2014/009,4375 for the sequence of BtagV7. The GGGSLVPRGSGGGS linker is listed as SEQ ID NO: 5.

| Mutations | C-terminal region features |
|---|---|
| T17W A68S K135Q L142K Y224K E239G V250I L253A R261K L326V T368S E375Y S395A T421Y W436Y A437G Y439W E466K A484E E508R D510R K512Y E515Q K539E P558A D570E | GGGSLVPRGSGGGS BtagV7 BtagV7 G His10 |
| T17W A68S K135Q L142K S192A Y224K E239G V250I L253A R261K L326V T368S E375Y T421Y W436Y A437G Y439W E466K A484E E508R D510R K512Y E515Q K539E P558A D570E | GGGSLVPRGSGGGS BtagV7 BtagV7 G His10 |
| T17W A68S Y101F K135Q L142K Y224K E239G V250I L253A R261K L326V T368S E375Y T421Y W436Y A437G Y439W E466K A484E E508R D510R K512Y E515Q K539E P558A D570E | GGGSLVPRGSGGGS BtagV7 BtagV7 G His10 |
| T17W A68S K135Q L142K Y224K E239G V250I L253A R261K L326V T368S E375Y T421Y W436Y A437G Y439W E466K A484E Q497R E508R D510R K512Y E515Q K539E P558A D570E | GGGSLVPRGSGGGS BtagV7 BtagV7 G His10 |
| T17W A68S K135Q L142K Y224K E239G V250I L253A R261K L326V T368S E375Y T421Y W436Y A437G Y439W E466K A484E Q497K E508R D510R K512Y E515Q K539E P558A D570E | GGGSLVPRGSGGGS BtagV7 BtagV7 G His10 |
| T17W A68S K135Q L142K Y224K E239G V250I L253A R261K K305R L326V T368S E375Y T421Y W436Y A437G Y439W E466K A484E E508R D510R K512Y E515Q K539E P558A D570E | GGGSLVPRGSGGGS BtagV7 BtagV7 G His10 |
| T17W A68S K135Q L142K Y224K E239G V250I L253A R261K L326V T368S E375Y T421Y W436Y A437G Y439W E466K A484E E508R D510R K512Y E515Q K539E P558A D570E K575R | GGGSLVPRGSGGGS BtagV7 BtagV7 G His10 |
| T17W A68S K135Q L142K Y224K E239G V250I L253A R261K L326V T368S E375Y T421Y W436Y A437G Y439W E466K A484E R496K E508R D510R K512Y E515Q K539E P558A D570E | GGGSLVPRGSGGGS BtagV7 BtagV7 G His10 |
| T17W A68S K135Q L142K Y224K E239G V250I L253A R261K L326V T368S E375Y T421Y W436Y A437G Y439W E466K A484E E508R D510R K512Y E515Q K539E K557R P558A D570E | GGGSLVPRGSGGGS BtagV7 BtagV7 G His10 |
| T17W A68S K135Q L142K Y224K E239G V250I L253A R261K L326V T368S T373F E375Y T421Y W436Y A437G Y439W E466K A484E E508R D510R K512Y E515Q K539E P558A D570E | GGGSLVPRGSGGGS BtagV7 BtagV7 G His10 |
| T17W A68S K135R L142K Y224K E239G V250I L253A R261K L326V T368S T373F E375Y T421Y W436Y A437G Y439W E466K A484E E508R D510R K512Y E515Q K539E P558A D570E | GGGSLVPRGSGGGS BtagV7 BtagV7 G His10 |
| T17W A68S K135Q L142K Y224K E239G V250I L253A R261K L326V T368S E375W T421Y W436Y A437G Y439W E466K A484E E508R D510R K512H E515Q K539E P558A D570E | GGGSLVPRGSGGGS BtagV7 BtagV7 G His10 |
| T17W A68S K135R L142K Y224K E239G V250I L253A R261K L326V T368S T373F E375W T421Y W436Y A437G Y439W E466K A484E E508R D510R K512H E515Q K539E P558A D570E | GGGSLVPRGSGGGS BtagV7 BtagV7 G His10 |
| T17W A68S A83E K135Q L142K Y224K E239G V250I L253A R261K L326V T368S E375Y E420R T421Y W436Y A437G Y439W E466K A484E E508R D510R K512Y E515Q K539E P558A D570E | GGGSLVPRGSGGGS BtagV7 BtagV7 G His10 |

TABLE 1-continued

Exemplary mutations introduced into a Φ29 DNA polymerase engineered for RNA sequencing. Positions are identified relative to SEQ ID NO: 1. See, e.g., U.S. patent application publications 2012/0034,602 and 2014/009,4375 for the sequence of BtaqV7. The GGGSLVPRGSGGGS linker is listed as SEQ ID NO: 5.

| Mutations | C-terminal region features |
|---|---|
| T17W A68S A83E K135Q L142K Y224K E239G V250I L253A R261K L326V T368S E375Y E420R T421Y W436Y A437G Y439W E466K A484E E508R D510R K512Y E515Q K539E P558A D570T | GGGSLVPRGSGGGS BtagV7 BtagV7 G His10 |
| T17W A68S A83E K135R L142K Y224K E239G V250I L253A R261K L326V T368S T373F E375W E420R T421Y W436Y A437G Y439W E466K A484E E508R D510R K512H E515Q K539E P558A D570E | GGGSLVPRGSGGGS BtagV7 BtagV7 G His10 |

Although Φ29-type polymerases with reverse transcriptase activity have been described in terms of RNA sequencing, it will be evident that they can be employed for other applications. The polymerases of the invention can thus be employed, for example, in any reverse transcription reaction, e.g., for amplification, cDNA generation, RT-PCR, and the like, including applications at higher temperatures and/or for templates having a large amount of secondary structure.

As noted, the various mutations described and referenced herein can be combined in recombinant polymerases useful in the invention. Combination of mutations can be random, or more desirably, guided by the properties of the particular mutations and the characteristics desired for the resulting polymerase. Additional mutations can also be introduced into a polymerase to compensate for deleterious effects of otherwise desirable mutations.

It is worth noting that various of the mutations described herein for modification of a Φ29 polymerase (or other Φ29-type polymerase) to increase its reverse transcriptase activity are also useful in modifying Φ29 (or another Φ29-type polymerase) to create an RNA polymerase, e.g., an RNA dependent RNA polymerase. An RNA polymerase based on Φ29 is advantageous due to its processivity and its ability, unlike a typical RNA polymerase, to initiate synthesis from a primer (and optionally thus to incorporate 5' labels). Suitable mutations for use in such a polymerase include, for example, any mutation noted herein that increases Φ29 polymerase's ability to accept an RNA template (e.g., by accepting an A form helix and/or by reducing clashes with a 2' hydroxyl group on the template), reduces or eliminates the endogenous exonuclease activity (e.g., mutations that inhibit primer strand binding to the exonuclease domain), increases cognate base affinity in the active site, and/or provides other improvements in performance (e.g., increased processivity, increased readlength, increased thermostability, or the like as noted herein). Additional mutations that can be included to increase RNA polymerase ability of Φ29 include, e.g., a mutation at gatekeeper residue Y254, which can permit Φ29 to incorporate rNTPs or ribonucleotide analogs. Exemplary mutations include, e.g., Y254F, Y254V, Y254N, and Y254S.

As noted above, the mutations and mutational strategies herein can be combined with those taught in, e.g., US patent application publications 2007-0196846, 2008-0108082, 2010-0075332, 2010-0093555, 2010-0112645, 2011-0189659, 2012-0034602, 2013-0217007, 2014-0094374, 2014-0094374, and 2014-0094375, previously incorporated herein by reference. This combination of mutations/mutational strategies can be used to impart several simultaneous improvements to a polymerase. In addition, polymerases can be further modified for application-specific reasons, such as to improve activity of the enzyme when bound to a surface, as taught, e.g., in US patent application publications 2010-0261247 and 2010-0260465, previously incorporated by reference and/or to include purification or handling tags as is taught in the cited references and as is common in the art. Similarly, the modified polymerases described herein can be employed in combination with other strategies to improve polymerase performance, for example, reaction conditions for controlling polymerase rate constants such as taught in US patent application publication US 2009-0286245, incorporated previously by reference.

A list of exemplary polymerase mutation combinations for a modified recombinant Φ29 polymerase that functions as an RNA polymerase, and optional corresponding exogenous features at the C-terminal region of the polymerase, is provided in Table 2. Positions of amino acid substitutions are identified relative to a wild-type Φ29 DNA polymerase (SEQ ID NO:1). Polymerases of the invention (including those provided in Table 2) can include any exogenous or heterologous feature (or combination of such features), e.g., at the N- and/or C-terminal region. For example, some or all of the exogenous features listed in Table 2 can be omitted, or substituted or combined with any of the other exogenous features described herein, and still result in a polymerase of the invention. As will be appreciated, the numbering of amino acid residues is with respect to a particular reference polymerase, such as the wild-type sequence of the Φ29 polymerase (SEQ ID NO:1); actual position of a mutation within a molecule of the invention may vary based upon the nature of the various modifications that the enzyme includes relative to the wild type Φ29 enzyme, e.g., deletions and/or additions to the molecule, either at the termini or within the molecule itself.

TABLE 2

Exemplary mutations introduced into a Φ29 DNA polymerase engineered for RNA polymerase activity. Positions are identified relative to SEQ ID NO: 1. See, e.g., U.S. patent application publications 2012/003,4602 and 2014/009,4375 for the sequence of BtagV7. The GGGSGGGSGGGS linker is listed as SEQ ID NO: 6.

| Mutations | C-terminal region features |
|---|---|
| A68S K135Q L142K Y224K E239G V250I L253A Y254F R306Q R308L T368S E375Y T421Y A437G E466K D476H A484E E508R D510R K512Y E515Q K539E P558A D570S T571V | G His10co GGGSGGGSGGGS BtagV7 GGGSGGGSGGGS BtagV7 |
| A68S K135Q L142K Y224K E239G V250I L253A Y254V R306Q R308L T368S E375Y T421Y A437G E466K D476H A484E E508R D510R K512Y E515Q K539E P558A D570S T571V | G His10co GGGSGGGSGGGS BtagV7 GGGSGGGSGGGS BtagV7 |
| A68S K135Q L142K Y224K E239G V250I L253A Y254N R306Q R308L T368S E375Y T421Y A437G E466K D476H A484E E508R D510R K512Y E515Q K539E P558A D570S T571V | G His10co GGGSGGGSGGGS BtagV7 GGGSGGGSGGGS BtagV7 |
| A68S K135Q L142K Y224K E239G V250I L253A Y254S R306Q R308L T368S E375Y T421Y A437G E466K D476H A484E E508R D510R K512Y E515Q K539E P558A D570S T571V | G His10co GGGSGGGSGGGS BtagV7 GGGSGGGSGGGS BtagV7 |

Engineering HIV RT for Processivity and Compatibility with Fluorescently Labeled Analogs In another aspect, the polymerase that is modified is a reverse transcriptase. For example, the modified recombinant polymerase can be homologous to an HIV reverse transcriptase. HIV reverse transcriptase includes two subunits, p66 and p51. In the virus, both subunits are encoded by the same gene, and the smaller subunit results from proteolytic processing in cellulo. Recombinant reverse transcriptase is more conveniently produced by expression of p66 and p51 from different plasmids in different host cells followed by reconstruction of the heterodimer; see, e.g., Kensch et al. (2000) "Temperature-dependent equilibrium between the open and closed conformation of the p66 subunit of HIV-1 reverse transcriptase revealed by site-directed spin labelling" J Mol Biol. 301:1029-39. A given mutation can thus be introduced into either p66 or p51 or both, as desired. In the following discussion, mutations are introduced into p66 (and optionally but not necessarily also p51) unless otherwise noted.

HIV reverse transcriptase has been employed for determination of RNA sequence, base modifications, and structure. See, e.g., Vilfan et al. supra. However, the performance of the enzyme, particularly in single molecule sequencing applications, can be improved, for example, by increasing its processivity and by improving its ability to employ fluorescently labeled nucleotide analogs useful in single molecule sequencing.

Processivity of HIV reverse transcriptase on an RNA template can be increased by locking the template in place in the enzyme with chemical cross-links. For example, a bifunctional cross-linker can be reacted with residues in the polymerase on each side of the bound template, topologically encircling the template. Cysteine residues can be introduced into the polymerase at suitable positions for cross-link formation. Thus, the polymerase can include, e.g., a first substitution in p66 such as, e.g., W25C, K14C, or K23C, and a second substitution in p66 such as, e.g., K288C or A289C. The two cysteine residues introduced by one of these combinations of mutations are then connected (e.g., covalently connected) by a linker. Although such cross-links are conveniently formed between residues within p66, cross-links can also be formed across subunits of the heterodimer, for example, between W25C in p51 and K288C in p66. Existing solvent accessible cysteine residues can be mutated to ensure that the cross-link is formed between the desired pair of residues; thus, the polymerase can also include one or more substitutions such as, e.g., C39S and/or C281S (e.g., C281S in p51 and p66 and C39S in p66). Suitable bifunctional linkers are known in the art, for example, a bismaleimide linker, e.g., a bismaleimide-PEG linker, e.g., BM(PEG)$_{10}$. Other coupling chemistries that can be employed include, e.g., thiol reactive reagents and disulfide containing reagents, e.g., haloacetyl crosslinkers (e.g., linkers including two iodoacetyl/iodoacetamide or bromoacetyl groups) and linkers with two pyridyl disulfide groups. The body of the linker can include, e.g., PEG (polyethylene glycol), an oligopeptide (e.g., polyglycine, e.g., Gly10), or the like. Optimal linker length can be chosen based on the distance between the two residues to be cross-linked, e.g., in a crystal structure or other model of the polymerase. The linker is typically reacted with the polymerase after binding of the template (or primer/template); suitable reaction conditions for various linker chemistries are known in the art. Noncovalent linkers can also be employed. Optionally, the linker has additional functionality. For example, a trifunctional linker can be employed, with two of the groups being used to cross-link two residues in the polymerase and the third group being used for addition of a polynucleotide binding moiety (e.g., to increase readlength) or of a biotin or other group to facilitate immobilization of the polymerase on a surface.

Figure 3:
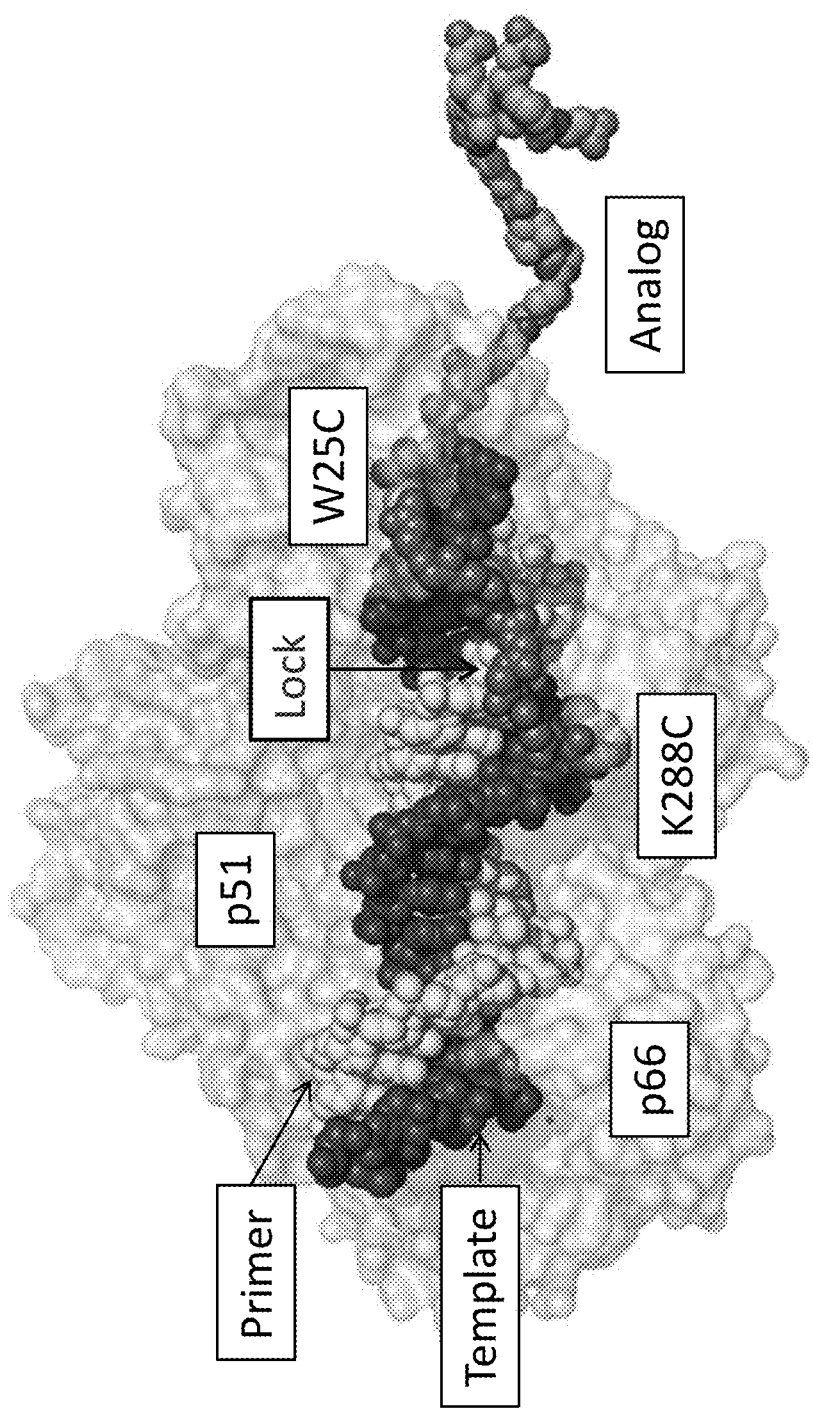
FIG. 3 shows a model of a recombinant HIV reverse transcriptase including W25C and K288C substitutions in p66 topologically locked around template by reaction of a bifunctional linker with the two cysteines.

A model of a recombinant HIV reverse transcriptase including W25C and K288C substitutions in p66 topologically locked around template by reaction of a bifunctional linker with the two cysteines is shown in FIG. 3. Topological encirclement of the template by polymerase is particularly effective for circular templates (including, e.g., simple circles and SMRTbells™ as described in, e.g., U.S. Pat. No. 8,153,375 and Travers et al. supra, comprising at least one region of ribonucleotides).

Although topological encirclement of template by reverse transcriptase has been described in terms of RNA sequencing, it will be evident that it can be employed for other applications, particularly applications in which the low processivity of reverse transcriptase and/or template switching are problematic. Encirclement can also be desirable when performing reverse transcription at higher temperatures. The reverse transcriptases of the invention can thus be employed, for example, in any reverse transcription reaction, e.g., for amplification, cDNA generation, RT-PCR, and the like.

Employment of fluorescently labeled nucleotide analogs, particularly phosphate-labeled analogs (e.g., analogs having a fluorescent dye attached to the terminal phosphate of an analog having three, four, five, six, or more phosphate groups) can be enhanced by altering residues positioned to interact with the polyphosphate, the label, and/or a linker between the polyphosphate and label. For example, D68 can be altered to avoid having a negative charge oriented toward the polyphosphate, e.g., to D68N, D68S, or D68Q. Residue K220 can be altered to reduce interaction with D68 to avoid clashes with the polyphosphate or linker, e.g., to K220Q. Favorable interactions with the linker can be introduced, e.g., by changing K220 and/or H222 to a hydrophobic residue, e.g., to K220W, K220Y, K220F, K220M, H222Y, H222W, or H222F. Interaction with additional phosphate groups (e.g., a fourth, fifth, and or six phosphate group) can be introduced, e.g., by mutation of V246, e.g., to V246K or V246R.

Mutations can also be introduced to affect the polymerase kinetic cycle. For example, mutation of K221 can affect the open/closed transition, with substitutions such as, e.g., K221E and K221D. Mutation of E90 can favor the closed conformation and reduce branching. Exemplary substitutions include, e.g., E90K and E90R.

Other exemplary positions of interest include, but are not limited to, A115, K66, and K67. Exemplary substitutions include, e.g., A115G, A115S, K66R, K67H, and K67R.

The polymerase mutations noted herein can be combined with each other and with essentially any other available mutations and mutational strategies to confer additional improvements in, e.g., performance in single molecule sequencing reactions, ability to incorporate fluorescently labeled phospholinked nucleotide analogs, nucleotide analog specificity, enzyme processivity, and/or the like. Combination of mutations can be random, or more desirably, guided by the properties of the particular mutations and the characteristics desired for the resulting polymerase. Additional mutations can also be introduced into a polymerase to compensate for deleterious effects of otherwise desirable mutations.

Mutating Polymerases

Various types of mutagenesis are optionally used in the present invention, e.g., to modify polymerases to produce variants, e.g., in accordance with polymerase models and model predictions as discussed above, or using random or semi-random mutational approaches. In general, any available mutagenesis procedure can be used for making polymerase mutants. Such mutagenesis procedures optionally include selection of mutant nucleic acids and polypeptides for one or more activity of interest (e.g., enhanced performance with labeled nucleotide analogs, improved processivity, increased thermostability, increased readlength, increased sensitivity to base modifications, increased phototolerance, reduced reaction rates, decreased exonuclease activity, increased complex stability, decreased branching fraction, altered metal cofactor selectivity, increased yield, increased accuracy, and/or improved $k_{off}$, $K_m$, $V_{max}$, $k_{cat}$ etc., e.g., for a given nucleotide analog). Procedures that can be used include, but are not limited to: site-directed point mutagenesis, random point mutagenesis, in vitro or in vivo homologous recombination (DNA shuffling and combinatorial overlap PCR), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to persons of skill. The starting polymerase for mutation can be any of those noted herein, including available polymerase mutants such as those identified, e.g., US patent application publication 2007-0196846 "Polymerases for Nucleotide Analogue Incorporation" by Hanzel et al., US patent application publication 2008-0108082 "Polymerase Enzymes and Reagents for Enhanced Nucleic Acid Sequencing" by Rank et al., US patent application publication 2010-0075332 "Engineering Polymerases and Reaction Conditions for Modified Incorporation Properties" by Pranav Patel et al., US patent application publication 2010-0093555 "Enzymes Resistant to Photodamage" by Keith Bjornson et al., US patent application publication 2010-0112645 "Generation of Modified Polymerases for Improved Accuracy in Single Molecule Sequencing" by Sonya Clark et al., US patent application publication 2011-0189659 "Generation of Modified Polymerases for Improved Accuracy in Single Molecule Sequencing" by Sonya Clark et al., US patent application publication 2012-0034602 "Recombinant Polymerases For Improved Single Molecule Sequencing" by Robin Emig et al., US patent application publication 2013-0217007 "Recombinant Polymerases with Increased Phototolerance" by Satwik Kamtekar et al., US patent application publication 2014-0094374 "Recombinant Polymerases with Increased Readlength and Stability for Single-Molecule Sequencing" by Satwik Kamtekar et al., US patent application publication 2014-0094375 "Recombinant Polymerases for Incorporation of Protein Shield Nucleotide Analogs" by Satwik Kamtekar et al., US patent application publication 2010-0261247 "Active Surface Coupled Polymerases" by Hanzel et al., and US patent application publication 2010-0260465 "Protein Engineering Strategies to Optimize Activity of Surface Attached Proteins" by Hanzel et al.

Optionally, mutagenesis can be guided by known information from a naturally occurring polymerase molecule, or of a known altered or mutated polymerase (e.g., using an existing mutant polymerase as noted in the preceding references), e.g., sequence, sequence comparisons, physical properties, crystal structure and/or the like as discussed above. However, in another class of embodiments, modification can be essentially random (e.g., as in classical or "family" DNA shuffling, see, e.g., Crameri et al. (1998) "DNA shuffling of a family of genes from diverse species accelerates directed evolution" Nature 391:288-291).

Additional information on mutation formats is found in: Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2015) ("Ausubel")); and *PCR Protocols A Guide to Methods and Applications* (Innis et al. eds) Academic Press Inc. San Diego, Calif. (1990) ("Innis").

Determining Kinetic Parameters

The polymerases of the invention can be screened or otherwise tested to determine whether the polymerase displays a modified activity for or with a nucleotide analog or template as compared to a parental DNA polymerase (e.g., a corresponding wild-type or available mutant polymerase from which the recombinant polymerase of the invention was derived). For example, branching fraction, a reaction rate constant, $k_{off}$, $k_{cat}$, $K_m$, $V_{max}$, $k_{cat}/K_m$, $V_{max}/K_m$, $k_{pol}$, and/or $K_d$ of the recombinant DNA polymerase for the nucleotide (or analog) or template nucleic acid can be determined. The specificity constant $k_{cat}/K_m$ is also a useful measure, e.g., for assessing branch rate. $k_{cat}/K_m$ is a measure of substrate binding that leads to product formation (and, thus, includes terms defining binding $K_d$ and inversely predicts branching fraction formation).

As is well-known in the art, for enzymes obeying simple Michaelis-Menten kinetics, kinetic parameters are readily derived from rates of catalysis measured at different substrate concentrations. The Michaelis-Menten equation, $V=V_{max}[S]([S]+K_m)^{-1}$, relates the concentration of free substrate ([S], approximated by the total substrate concentration), the maximal rate ($V_{max}$, attained when the enzyme is saturated with substrate), and the Michaelis constant ($K_m$, equal to the substrate concentration at which the reaction rate is half of its maximal value), to the reaction rate (V).

For many enzymes, $K_m$ is equal to the dissociation constant of the enzyme-substrate complex and is thus a measure of the strength of the enzyme-substrate complex. For such an enzyme, in a comparison of $K_m$s, a lower $K_m$ represents a complex with stronger binding, while a higher Km represents a complex with weaker binding. The ratio $k_{cat}/K_m$, sometimes called the specificity constant, can be thought of as the second order rate constant times the probability of that substrate being converted to product once bound. The larger the specificity constant, the more efficient the enzyme is in binding the substrate and converting it to product. The specificity constant is inversely proportional to the branching rate, as branching rate is the rate at which the enzyme binds substrate (e.g., nucleotide) but does not convert it to product (e.g., a DNA polymer).

$k_{cat}$ (also called the turnover number of the enzyme) can be determined if the total enzyme concentration ($[E_T]$, i.e., the concentration of active sites) is known, since $V_{max}=k_{cat}[ET]$. For situations in which the total enzyme concentration is difficult to measure, the ratio $V_{max}/K_m$ is often used instead as a measure of efficiency. $K_m$ and $V_{max}$ can be determined, for example, from a Lineweaver-Burk plot of 1/V against 1/[S], where the y intercept represents $1/V_{max}$, the x intercept $-1/K_m$, and the slope $K_m/V_{max}$, or from an Eadie-Hofstee plot of V against V/[S], where the y intercept represents $V_{max}$, the x intercept $V_{max}/K_m$, and the slope $-K_m$. Software packages such as KinetAsyst™ or Enzfit (Biosoft, Cambridge, UK) can facilitate the determination of kinetic parameters from catalytic rate data.

For enzymes such as polymerases that have multiple substrates, varying the concentration of only one substrate while holding the others in suitable excess (e.g., effectively constant) concentration typically yields normal Michaelis-Menten kinetics.

Details regarding $k_{off}$ determination are described, e.g., in US patent application publication 2012-0034602. In general, the dissociation rate can be measured in any manner that detects the polymerase/DNA complex over time. This includes stopped-flow spectroscopy, or even simply taking aliquots over time and testing for polymerase activity on the template of interest. Free polymerase is captured with a polymerase trap after dissociation, e.g., by incubation in the presence of heparin or an excess of competitor DNA (e.g., non-specific salmon sperm DNA, or the like).

In one embodiment, using pre-steady-state kinetics, the nucleotide concentration dependence of the rate constant $k_{obs}$ (the observed first-order rate constant for dNTP incorporation) provides an estimate of the $K_m$ for a ground state binding and the maximum rate of polymerization ($k_{pol}$). The $k_{obs}$ is measured using a burst assay. The results of the assay are fitted with the burst equation; Product=A[1−exp(−$k_{obs}$*t)]+$k_{ss}$*t where A represents amplitude an estimate of the concentration of the enzyme active sites, $k_{ss}$ is the observed steady-state rate constant and t is the reaction incubation time. The $K_m$ for dNTP binding to the polymerase-DNA complex and the $k_{pol}$ are calculated by fitting the dNTP concentration dependent change in the $k_{obs}$ using the equation $k_{obs}=(k_{pol}*[S])*(K_m+[S])^{-1}$ where [S] is the substrate concentration. Results are optionally obtained from a rapid-quench experiment (also called a quench-flow measurement), for example, based on the methods described in Johnson (1986) "Rapid kinetic analysis of mechano-chemical adenosinetriphosphatases" Methods Enzymol. 134:677-705, Patel et al. (1991) "Pre-steady-state kinetic analysis of processive DNA replication including complete characterization of an exonuclease-deficient mutant" Biochemistry 30(2):511-25, and Tsai and Johnson (2006) "A new paradigm for DNA polymerase specificity" Biochemistry 45(32):9675-87.

Parameters such as rate of binding of a nucleotide analog or template by the recombinant polymerase, rate of product release by the recombinant polymerase, or branching rate of the recombinant polymerase can also be determined, and optionally compared to that of a parental polymerase (e.g., a corresponding wild-type polymerase).

For a more thorough discussion of enzyme kinetics, see, e.g., Berg, Tymoczko, and Stryer (2002) *Biochemistry, Fifth Edition*, W. H. Freeman; Creighton (1984) *Proteins: Structures and Molecular Principles*, W. H. Freeman; and Fersht (1985) *Enzyme Structure and Mechanism, Second Edition*, W. H. Freeman.

In one aspect, the improved activity of the enzymes of the invention is compared with a given parental polymerase. For example, in the case of enzymes derived from a Φ29 parental enzyme, where the improvement being sought is an increase in stability of the closed complex, an improved enzyme of the invention would have a lower $k_{off}$ than the parental enzyme, e.g., wild type Φ29. Such comparisons are made under equivalent reaction conditions, e.g., equal concentrations of the parental and modified polymerase, equal substrate concentrations, equivalent solution conditions (pH, salt concentration, presence of divalent cations, etc.), temperature, and the like. In one aspect, the improved activity of the enzymes of the invention is measured with reference to a model analog or analog set and compared with a given parental enzyme. Optionally, the improved activity of the enzymes of the invention is measured under specified reaction conditions. While the foregoing may be used as a characterization tool, it in no way is intended as a specifically limiting reaction of the invention.

Optionally, the polymerase exhibits a $K_m$ for a phosphate-labeled nucleotide analog that is less than a $K_m$ observed for a wild-type polymerase for the analog to facilitate applications in which the polymerase incorporates the analog, e.g., during single molecule sequencing. For example, the modified recombinant polymerase can exhibit a $K_m$ for the phosphate-labeled nucleotide analog that is less than less than 75%, 50%, 25% or less than that of wild-type or parental polymerase such as a wild type Φ29. In one specific class of examples, the polymerases of the invention have a $K_m$ of about 10 μM or less for a non-natural nucleotide analog such as a phosphate labeled analog.

Screening Polymerases

Screening or other protocols can be used to determine whether a polymerase displays a modified activity, e.g., for a nucleotide analog, as compared to a parental DNA polymerase. For example, branching fraction, rate constant, $k_{off}$, $k_{cat}$, $K_m$, $V_{max}$, or $k_{cat}/K_m$ of the recombinant DNA polymerase for the template or nucleotide or analog can be determined as discussed above. As another example, activity can be assayed indirectly. Assays for properties such as protein yield, thermostability (of free polymerase, binary complex, or ternary complex), and the like are described, e.g., in US patent application publications 2012-0034602 and 2014-0094374. Performance of a recombinant polymerase in a sequencing reaction, e.g., a single molecule sequencing reaction, can be examined to assay properties such as speed, pulse width, interpulse distance, accuracy, readlength, ability to incorporate large nucleotide analogs, sensitivity to base modifications, etc. as described herein. Phototolerance can be assessed by monitoring polymerase performance (e.g., in a single molecule sequencing reaction) during or after exposure of the polymerase to light, e.g., excitation light of a specified wavelength at a given intensity for a given time, e.g., as compared to a wild-type or other parental polymerase. Resistance to cosolvents can be assessed by monitoring polymerase performance in the presence of varying amounts of the solvent (e.g., in a primarily aqueous solution containing various amounts of an organic solvent, e.g., DMSO, e.g., 1-10%, 2-10%, 2-5%, or 5-8% by volume of the solvent). Processivity can be assessed as described in the art; see, e.g., US patent application publication 2007-0196846. Ability to employ an RNA template can initially be assessed using a primer extension assay, e.g., using a symmetrical oligo cassette that includes a primer/template strand with a self-complementary region at its 3' end. Ribonucleotides are included in the template portion of the template/primer strand to assess the polymerase's ability to synthesize past ribo bases. The primer/template strand can consist of ribonucleotides, or it can include at least one region of ribonucleotides preceded, followed, or flanked by deoxyribonucleotides (e.g., a stretch of 10 or more ribonucleotides flanked by stretches of deoxyribonucleotides). Extension products can be resolved by gel electrophoresis. For higher throughput an optical strand displacement assay can be employed, e.g., using a symmetrical oligo cassette that includes a primer/template strand with a self-complementary region at its 3' end and a displaced strand that hybridizes to the 5' end of the primer/template strand, with a Fam label on the 5' end of the primer/template strand and a quencher on the 3' end of the displaced strand. Ribonucleotides are included in the primer/template strand as noted for the gel-based assay. A polymerase's ability to employ an RNA template can also be assessed in single molecule sequencing reactions, using templates containing a stretch of ribonucleotides or entirely comprising RNA. A region of ribonucleotides in a template typically includes 10 or more or 20 or more contiguous ribonucleotides (e.g., for a strand displacement assay) or 50 or more, 100 or more, 500 or more, 1000 or more, or even 2000 or more contiguous ribonucleotides (e.g., for characterization by single molecule sequencing). A polymerase can be said to have RNA-directed polymerase activity when the polymerase produces full-length product in such a primer extension assay (indicating that the polymerase read through and incorporated cognate nucleotides into a product strand in response to the ribonucleotide template segment) and/or when the polymerase sequences through a stretch of ribonucleotides in a template in a single molecule sequencing reaction. Accuracy, readlength, and the like of the polymerase for RNA templates can also be evaluated in a single molecule sequencing reaction.

In one desirable aspect, a library of recombinant DNA polymerases can be made and screened for these properties. For example, a plurality of members of the library can be made to include one or more mutation that increases stability, increases readlength, improves detection of modified bases, enhances incorporation of large analogs, increases phototolerance, alters (e.g., decreases) reaction rate constants, improves closed complex stability, decreases branching fraction, alters cofactor selectivity, or increases cosolvent resistance, yield, accuracy, or speed, and/or randomly generated mutations (e.g., where different members include different mutations or different combinations of mutations), and the library can then be screened for the properties of interest (e.g., increased stability, readlength, utility of large analogs, or phototolerance, decreased rate constant, decreased branching fraction, increased closed complex stability, etc.). In general, the library can be screened to identify at least one member comprising a modified activity of interest.

Libraries of polymerases can be either physical or logical in nature. Moreover, any of a wide variety of library formats can be used. For example, polymerases can be fixed to solid surfaces in arrays of proteins. Similarly, liquid phase arrays of polymerases (e.g., in microwell plates) can be constructed for convenient high-throughput fluid manipulations of solutions comprising polymerases. Liquid, emulsion, or gel-phase libraries of cells that express recombinant polymerases can also be constructed, e.g., in microwell plates, or on agar plates. Phage display libraries of polymerases or polymerase domains (e.g., including the active site region or interdomain stability regions) can be produced. Likewise, yeast display libraries can be used. Instructions in making and using libraries can be found, e.g., in Sambrook, Ausubel and Berger, referenced herein.

For the generation of libraries involving fluid transfer to or from microtiter plates, a fluid handling station is optionally used. Several "off the shelf" fluid handling stations for performing such transfers are commercially available, including e.g., the Zymate systems from Caliper Life Sciences (Hopkinton, Mass.) and other stations which utilize automatic pipettors, e.g., in conjunction with the robotics for plate movement (e.g., the ORCA® robot, which is used in a variety of laboratory systems available, e.g., from Beckman Coulter, Inc. (Fullerton, Calif.).

In an alternate embodiment, fluid handling is performed in microchips, e.g., involving transfer of materials from microwell plates or other wells through microchannels on the chips to destination sites (microchannel regions, wells, chambers or the like). Commercially available microfluidic systems include those from Hewlett-Packard/Agilent Technologies (e.g., the HP2100 bioanalyzer) and the Caliper High Throughput Screening System. The Caliper High Throughput Screening System provides one example interface between standard microwell library formats and Labchip technologies. RainDance Technologies' nanodroplet platform provides another method for handling large numbers of spatially separated reactions. Furthermore, the patent and technical literature includes many examples of microfluidic systems which can interface directly with microwell plates for fluid handling.

Tags and Other Optional Polymerase Features

The recombinant polymerase optionally includes additional features exogenous or heterologous to the polymerase. For example, the recombinant polymerase optionally includes one or more tags, e.g., purification, substrate binding, or other tags, such as a polyhistidine tag, a His10 tag, a His6 tag, an alanine tag, an Ala10 tag, an Ala16 tag, a biotin tag, a biotin ligase recognition sequence or other biotin attachment site (e.g., a BiTag or a Btag or variant thereof, e.g., BtagV1-11), a GST tag, an S Tag, a SNAP-tag, an HA tag, a DSB (Sso7D) tag, a lysine tag, a NanoTag, a Cmyc tag, a tag or linker comprising the amino acids glycine and serine, a tag or linker comprising the amino acids glycine, serine, alanine and histidine, a tag or linker comprising the amino acids glycine, arginine, lysine, glutamine and proline, a plurality of polyhistidine tags, a plurality of His10 tags, a plurality of His6 tags, a plurality of alanine tags, a plurality of Ala10 tags, a plurality of Ala16 tags, a plurality of biotin tags, a plurality of GST tags, a plurality of BiTags, a plurality of S Tags, a plurality of SNAP-tags, a plurality of HA tags, a plurality of DSB (Sso7D) tags, a plurality of lysine tags, a plurality of NanoTags, a plurality of Cmyc tags, a plurality of tags or linkers comprising the amino acids glycine and serine, a plurality of tags or linkers comprising the amino acids glycine, serine, alanine and histidine, a plurality of tags or linkers comprising the amino acids glycine, arginine, lysine, glutamine and proline, biotin, avidin, an antibody or antibody domain, antibody fragment, antigen, receptor, receptor domain, receptor fragment, maltose binding protein, ligand, one or more protease site (e.g., Factor Xa, enterokinase, or thrombin site), a dye, an acceptor, a quencher, a DNA binding domain (e.g., a helix-hairpin-helix domain from topoisomerase V), a domain that binds modified bases (e.g., an MeCpG binding protein 2 domain, an O6-alkylguanine DNA alkyl transferase domain, a thymine dioxygenase JBP1 catalytic domain, or an SRA domain, e.g., from UHRF1), a sliding clamp domain or the like to increase affinity for DNA (e.g., an HSV UL42 domain), or combination thereof. See, e.g., US patent application publication 2012-0034602 for sequences of a number of suitable tags and linkers, including BtagV1-11. The one or more exogenous or heterologous features can find use not only for purification purposes, immobilization of the polymerase to a substrate, and the like, but can also be useful for altering one or more properties of the polymerase (e.g., addition of an exogenous feature at the C-terminus of a Φ29 polymerase (e.g., a His10 or other polyhistidine tag) can decrease exonuclease activity and/or increase binary and/or ternary complex stability).

The polymerase optionally includes one or more additional domains or motifs, e.g., that alter one or more properties of the polymerase. For example, the polymerase can include a Topo V helix-hairpin-helix domain fusion as described in de Vega et al. (2010) "Improvement of φ29 DNA polymerase amplification performance by fusion of DNA binding motifs" Proc Natl Acad Sci USA 107:16506-16511. As other examples, the polymerase can include a polynucleotide binding moiety, including, but not limited to, RNAse H or another endonuclease lacking activity (e.g., having mutations in one or more active site residues), a helix-hairpin-helix domain, single-stranded binding protein, double-stranded binding protein, sliding clamp, processivity factor, DNA binding loop, replication initiation protein, telomere binding protein, repressor, zinc finger, and/or proliferating cell nuclear antigen; exemplary suitable moieties are described in WO 2014/013260 and WO 2014/013262.

The one or more exogenous or heterologous features can be included internal to the polymerase, at the N-terminal region of the polymerase, at the C-terminal region of the polymerase, or at a combination thereof (e.g., at both the N-terminal and C-terminal regions of the polymerase). Where the polymerase includes an exogenous or heterologous feature at both the N-terminal and C-terminal regions, the exogenous or heterologous features can be the same (e.g., a polyhistidine tag, e.g., a His10 tag, at both the N- and C-terminal regions) or different (e.g., a biotin ligase recognition sequence at the N-terminal region and a polyhistidine tag, e.g., His10 tag, at the C-terminal region). Optionally, a terminal region (e.g., the N- or C-terminal region) of a polymerase of the invention can comprise two or more exogenous or heterologous features which can be the same or different (e.g., a biotin ligase recognition sequence and a polyhistidine tag at the N-terminal region, a biotin ligase recognition sequence, a polyhistidine tag, and a Factor Xa recognition site at the N-terminal region, and the like). As a few examples, the polymerase can include a polyhistidine tag at the C-terminal region, a biotin ligase recognition sequence at the N-terminal region and a polyhistidine tag at the C-terminal region, a biotin ligase recognition sequence and a polyhistidine tag at the N-terminal region, a biotin ligase recognition sequence and a polyhistidine tag at the N-terminal region and a polyhistidine tag at the C-terminal region, two biotin ligase recognition sequences at the C-terminal region (e.g., two tandem sequences, e.g., tandem Btags), or a polyhistidine tag and a biotin ligase recognition sequence at the C-terminal region.

For convenience, an exogenous or heterologous feature will often be expressed as a fusion domain of the overall polymerase protein, e.g., as a conventional in-frame fusion of a polypeptide sequence with the active polymerase enzyme (e.g., a polyhistidine tag fused in frame to an active polymerase enzyme sequence). However, features such as tags can be added chemically to the polymerase, e.g., by using an available amino acid residue of the enzyme or by incorporating an amino acid into the protein that provides a suitable attachment site for the coupling domain. Suitable residues of the enzyme can include, e.g., histidine, cysteine, or serine residues (providing for N, S, or O linked coupling reactions). Optionally, one or more cysteines present in the parental polymerase (e.g., up to all of the cysteines present on the polymerase's surface) can be replaced with a different amino acid; either a single reactive surface cysteine can be left unsubstituted or a single reactive surface cysteine can be introduced in place of another residue, for convenient addition of a feature, e.g., for surface immobilization through thiol labeling (e.g., addition of maleimide biotin, or maleimide and an alkyne for click labeling). Unnatural amino acids that comprise unique reactive sites can also be added to the enzyme, e.g., by expressing the enzyme in a system that comprises an orthogonal tRNA and an orthogonal synthetase that loads the unnatural amino acid in response to a selector codon.

The exogenous or heterologous features can find use, e.g., in the context of binding a polymerase in an active form to a surface, e.g., to orient and/or protect the polymerase active site when the polymerase is bound to a surface. In general, surface binding elements and purification tags that can be added to the polymerase (e.g., recombinantly or chemically) include, e.g., biotin attachment sites (e.g., biotin ligase recognition sequences such as Btags or BiTag), polyhistidine tags, His6 tags, His10 tags, biotin, avidin, GST sequences, modified GST sequences, e.g., that are less likely to form dimers, S tags, SNAP-tags, antibodies or antibody domains, antibody fragments, antigens, receptors, receptor domains, receptor fragments, ligands, and combinations thereof.

One aspect of the invention includes polymerases that can be coupled to a surface without substantial loss of activity (e.g., in an active form). Polymerases can be coupled to the surface through a single surface coupling domain or through multiple surface coupling domains which act in concert to increase binding affinity of the polymerase for the surface and to orient the polymerase relative to the surface. For example, the active site can be oriented distal to the surface, thereby making it accessible to a polymerase substrate (template, nucleotides, etc.). This orientation also tends to reduce surface denaturation effects in the region of the active site. In a related aspect, activity of the enzyme can be protected by making the coupling domains large, thereby serving to further insulate the active site from surface binding effects. Further details regarding the immobilization of a polymerase to a surface (e.g., the surface of a zero mode waveguide) in an active form are found in WO 2007/075987 "Active Surface Coupled Polymerases" by Hanzel et al. and WO 2007/075873 "Protein Engineering Strategies to Optimize Activity of Surface Attached Proteins" by Hanzel et al. Further details on attaching tags is available in the art. See, e.g., U.S. Pat. Nos. 5,723,584 and 5,874,239 for additional information on attaching biotinylation peptides to recombinant proteins.

The polymerase immobilized on a surface in an active form can be coupled to the surface through one or a plurality of artificial or recombinant surface coupling domains as discussed above, and typically displays a $k_{cat}/K_m$ (or $V_{max}/K_m$) that is at least about 1%, at least about 10%, at least about 25%, at least about 50%, or at least about 75% as high as a corresponding active polymerase in solution.

Exonuclease-Deficient Recombinant Polymerases

Many native DNA polymerases have a proof-reading exonuclease function which can yield substantial data analysis problems in processes that utilize real time observation of incorporation events as a method of identifying sequence information, e.g., single molecule sequencing applications. Even where exonuclease activity does not introduce such problems in single molecule sequencing, reduction of exonuclease activity can be desirable since it can increase accuracy (in some cases at the expense of readlength).

Accordingly, recombinant polymerases of the invention optionally include one or more mutations (e.g., substitutions, insertions, and/or deletions) relative to the parental polymerase that reduce or eliminate endogenous exonuclease activity. For example, relative to the wild-type Φ29 DNA polymerase of SEQ ID NO:1, one or more of positions N62, D12, E14, T15, T17, H61, D66, D169, K143, Y148, and H149 is optionally mutated to reduce exonuclease activity. Exemplary mutations that can reduce exonuclease activity include, e.g., N62D, N62H, D12A, T15I, E14I, E14A, T17W, D66A, K143D, D145A and D169A substitutions, as well as addition of an exogenous feature at the C-terminus (e.g., a polyhistidine tag). Additional exemplary substitutions in the exonuclease domain include N62S, D12N, D12R, D12M, E14Q, H61K, H61D, H61A, D66R, D66N, D66Q, D66K, D66M, D169N, K143R, Y148K, Y148A, Y148C, Y148D, Y148E, Y148F, Y148G, Y148H, Y148I, Y148L, Y148M, Y148N, Y148P, Y148Q, Y148R, Y148S, Y148T, Y148V, Y148W, and H149M. The polymerases of the invention optionally comprise one or more of these mutations. For example, in one aspect, the polymerase is a Φ29-type polymerase that includes one or more mutations in the N-terminal exonuclease domain (residues 5-189 as numbered with respect to wild-type Φ29).

Making and Isolating Recombinant Polymerases

Generally, nucleic acids encoding a polymerase of the invention can be made by cloning, recombination, in vitro synthesis, in vitro amplification and/or other available methods. A variety of recombinant methods can be used for expressing an expression vector that encodes a polymerase of the invention. Methods for making recombinant nucleic acids, expression and isolation of expressed products are well known and described in the art. A number of exemplary mutations and combinations of mutations, as well as strategies for design of desirable mutations, are described herein. Methods for making and selecting mutations in the active site of polymerases, including for modifying steric features in or near the active site to permit improved access by nucleotide analogs are found hereinabove and, e.g., in WO 2007/076057 "Polymerases for Nucleotide Analogue Incorporation" by Hanzel et al. and WO 2008/051530 "Polymerase Enzymes and Reagents for Enhanced Nucleic Acid Sequencing" by Rank et al.

Additional useful references for mutation, recombinant and in vitro nucleic acid manipulation methods (including cloning, expression, PCR, and the like) include Berger and Kimmel, *Guide to Molecular Cloning Techniques, Methods in Enzymology volume* 152 Academic Press, Inc., San Diego, Calif. (Berger); Kaufman et al. (2003) Handbook of Molecular and Cellular Methods in Biology and Medicine Second Edition Ceske (ed) CRC Press (Kaufman); and *The Nucleic Acid Protocols Handbook* Ralph Rapley (ed) (2000) Cold Spring Harbor, Humana Press Inc (Rapley); Chen et al. (ed) *PCR Cloning Protocols*, Second Edition (Methods in Molecular Biology, volume 192) Humana Press; and in Viljoen et al. (2005) *Molecular Diagnostic PCR Handbook* Springer, ISBN 1402034032.

In addition, a plethora of kits are commercially available for the purification of plasmids or other relevant nucleic acids from cells, (see, e.g., EasyPrep™, FlexiPrep™ both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both.

Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue*

Culture in Liquid Systems John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Nucleic acids encoding the recombinant polymerases of the invention are also a feature of the invention. A particular amino acid can be encoded by multiple codons, and certain translation systems (e.g., prokaryotic or eukaryotic cells) often exhibit codon bias, e.g., different organisms often prefer one of the several synonymous codons that encode the same amino acid. As such, nucleic acids of the invention are optionally "codon optimized," meaning that the nucleic acids are synthesized to include codons that are preferred by the particular translation system being employed to express the polymerase. For example, when it is desirable to express the polymerase in a bacterial cell (or even a particular strain of bacteria), the nucleic acid can be synthesized to include codons most frequently found in the genome of that bacterial cell, for efficient expression of the polymerase. A similar strategy can be employed when it is desirable to express the polymerase in a eukaryotic cell, e.g., the nucleic acid can include codons preferred by that eukaryotic cell.

A variety of protein isolation and detection methods are known and can be used to isolate polymerases, e.g., from recombinant cultures of cells expressing the recombinant polymerases of the invention. A variety of protein isolation and detection methods are well known in the art, including, e.g., those set forth in R. Scopes, Protein Purification, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods, 2nd Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice 3rd Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein. Additional details regarding protein purification and detection methods can be found in Satinder Ahuj a ed., *Handbook of Bioseparations*, Academic Press (2000).

Kits

The present invention also features kits that incorporate the polymerases of the invention, optionally with additional useful reagents such as one or more nucleotides and/or nucleotide analogs, e.g., for sequencing, nucleic acid amplification, or the like. Such kits can include the polymerase of the invention packaged in a fashion to enable use of the polymerase (e.g., the polymerase immobilized in a ZMW array), optionally with a set of different nucleotide analogs of the invention, e.g., those that are analogous to A, T, G, and C, e.g., where one or more of the analogs comprise a detectable moiety, to permit identification in the presence of the analogs. Depending upon the desired application, the kits of the invention optionally include additional reagents, such as natural nucleotides, a control template, and other reagents, such as buffer solutions and/or salt solutions, including, e.g., divalent metal ions such as $Ca^{++}$, $Mg^{++}$, $Mn^{++}$ and/or $Fe^{++}$, and standard solutions, e.g., dye standards for detector calibration. Such kits also typically include instructions for use of the compounds and other reagents in accordance with the desired application methods, e.g., nucleic acid sequencing, amplification and the like.

Nucleic Acid and Polypeptide Sequences and Variants

As described herein, the invention also features polynucleotide sequences encoding, e.g., a polymerase as described herein. However, one of skill in the art will immediately appreciate that the invention is not limited to the specifically exemplified sequences. For example, one of skill will appreciate that the invention also provides, e.g., many related sequences with the functions described herein, e.g., polynucleotides and polypeptides encoding conservative variants of a polymerase described herein. Combinations of any of the mutations noted herein or combinations of any of the mutations herein in combination with those noted in other available references relating to improved polymerases, such as US patent application publication 2007-0196846 "Polymerases for Nucleotide Analogue Incorporation" by Hanzel et al., US patent application publication 2008-0108082 "Polymerase Enzymes and Reagents for Enhanced Nucleic Acid Sequencing" by Rank et al., US patent application publication 2010-0075332 "Engineering Polymerases and Reaction Conditions for Modified Incorporation Properties" by Pranav Patel et al., US patent application publication 2010-0093555 "Enzymes Resistant to Photodamage" by Keith Bjornson et al., US patent application publication 2010-0112645 "Generation of Modified Polymerases for Improved Accuracy in Single Molecule Sequencing" by Sonya Clark et al., US patent application publication 2011-0189659 "Generation of Modified Polymerases for Improved Accuracy in Single Molecule Sequencing" by Sonya Clark et al., US patent application publication 2012-0034602 "Recombinant Polymerases For Improved Single Molecule Sequencing" by Robin Emig et al., US patent application publication 2013-0217007 "Recombinant Polymerases with Increased Phototolerance" by Satwik Kamtekar et al., US patent application publication 2014-0094374 "Recombinant Polymerases with Increased Readlength and Stability for Single-Molecule Sequencing" by Satwik Kamtekar et al., and US patent application publication 2014-0094375 "Recombinant Polymerases for Incorporation of Protein Shield Nucleotide Analogs" by Satwik Kamtekar et al. are also features of the invention.

Accordingly, the invention provides a variety of polypeptides (polymerases) and polynucleotides (nucleic acids that encode polymerases). Exemplary polynucleotides of the invention include, e.g., any polynucleotide that encodes a polymerase described herein. Because of the degeneracy of the genetic code, many polynucleotides equivalently encode a given polymerase sequence. Similarly, an artificial or recombinant nucleic acid that hybridizes to a polynucleotide indicated above under highly stringent conditions over substantially the entire length of the nucleic acid (and is other than a naturally occurring polynucleotide) is a polynucleotide of the invention. In one embodiment, a composition includes a polypeptide of the invention and an excipient (e.g., buffer, water, pharmaceutically acceptable excipient, etc.). The invention also provides an antibody or antisera specifically immunoreactive with a polypeptide of the invention (e.g., that specifically recognizes a feature of the polymerase that confers increased processivity).

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally similar sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid sequence. Similarly, "conservative amino acid substitutions," where one or a limited number of amino acids in an amino acid sequence (other than residues noted herein as being relevant to a feature or property of interest) are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid, while retaining the relevant mutational feature (for example, the conservative substitution can be of a residue distal to the active site region, or distal to an interdomain stability region). Thus, "conservative variations" of a listed polypeptide sequence of the present invention include substitutions of a small percentage, typically less than 5%, more typically less than 2% or 1%, of the amino acids of the polypeptide sequence, with an amino acid of the same conservative substitution group. Finally, the addition of sequences which do not alter the encoded activity of a nucleic acid molecule, such as the addition of a non-functional or tagging sequence (introns in the nucleic acid, poly His or similar sequences in the encoded polypeptide, etc.), is a conservative variation of the basic nucleic acid or polypeptide.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where substitutions within a group is a "conservative substitution".

TABLE 3

Conservative amino acid substitutions

| Nonpolar and/ or Aliphatic Side Chains | Polar, Uncharged Side Chains | Aromatic Side Chains | Positively Charged Side Chains | Negatively Charged Side Chains |
|---|---|---|---|---|
| Glycine Alanine Valine Leucine Isoleucine Proline | Serine Threonine Cysteine Methionine Asparagine Glutamine | Phenyl- alanine Tyrosine Tryptophan | Lysine Arginine Histidine | Aspartate Glutamate |

Nucleic Acid Hybridization

Comparative hybridization can be used to identify nucleic acids of the invention, including conservative variations of nucleic acids of the invention. In addition, target nucleic acids which hybridize to a nucleic acid of the invention under high, ultra-high and ultra-ultra high stringency conditions, where the nucleic acids encode mutant polymerases described herein, are a feature of the invention. Examples of such nucleic acids include those with one or a few silent or conservative nucleic acid substitutions as compared to a given nucleic acid sequence encoding an exemplified polymerase), where any conservative substitutions are for residues other than those noted as being relevant to a feature of interest (increased processivity or readlength, improved performance with analogs, etc.).

A test nucleic acid is said to specifically hybridize to a probe nucleic acid when it hybridizes at least 50% as well to the probe as to the perfectly matched complementary target, i.e., with a signal to noise ratio at least half as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in *Current Protocols in Molecular Biology*, Ausubel et al., eds., *Current Protocols*, a joint venture between Greene Publishing Associates, Inc. and John Wiley & Sons, Inc., (supplemented through 2012); Hames and Higgins (1995) *Gene Probes* 1 IRL Press at Oxford University Press, Oxford, England, (Hames and Higgins 1) and Hames and Higgins (1995) Gene Probes 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In some aspects, the invention provides a nucleic acid that comprises a unique subsequence in a nucleic acid that encodes a polymerase of described herein. The unique subsequence may be unique as compared to a nucleic acid corresponding to, e.g., a wild type Φ29-type polymerase or wild-type HIV reverse transcriptase. Alignment can be performed using, e.g., BLAST set to default parameters. Any unique subsequence is useful, e.g., as a probe to identify the nucleic acids of the invention.

Similarly, the invention includes a polypeptide which comprises a unique subsequence in a polymerase o detailed herein. Here, the unique subsequence is unique as compared to, e.g., a wild type Φ29-type polymerase, a wild-type HIV reverse transcriptase, or previously characterized mutation thereof.

The invention also provides for target nucleic acids which hybridize under stringent conditions to a unique coding oligonucleotide which encodes a unique subsequence in a polypeptide selected from the modified polymerase sequences of the invention, wherein the unique subsequence is unique as compared to a polypeptide corresponding to a wild type Φ29-type polymerase or wild-type HIV reverse transcriptase. Unique sequences are determined as noted above.

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a polymerase, or the amino acid sequence of a polymerase) refers to two or more sequences or subsequences that have at least about 60%, about 80%, about 90%, about 95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., 30%, 40%, 50%, 60%, 70%, 75%, 80%, 90%, 95%, 97%, 98%, or 99% or more identity, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., *Current Protocols*, a joint venture between Greene Publishing Associates, Inc. and John Wiley & Sons, Inc., supplemented through 2012).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul (1993) Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

For reference, the amino acid sequences of a wild-type Φ29 polymerase, a wild-type M2Y polymerase, and a wild-type HIV reverse transcriptase (p66 and p51 subunits) are presented in Table 4.

TABLE 4

| Amino acid sequence of exemplary wild-type polymerases. | |
|---|---|
| Φ29 SEQ ID NO: 1 | MKHMPRKMYSCDFETTTKVEDCRVWAYGYMNIEDHSEYKIGNS LDEFMAWVLKVQADLYFHNLKFDGAFIINWLERNGFKWSADGL PNTYNTIISRMGQWYMIDICLGYKGKRKIHTVIYDSLKKLPFP VKKIAKDFKLTVLKGDIDYHKERPVGYKITPEEYAYIKNDIQI IAEALLIQFKQGLDRMTAGSDSLKGFKDIITTKKFKKVFPTLS LGLDKEVRYAYRGGFTWLNDRFKEKEIGEGMVFDVNSLYPAQM YSRLLPYGEPIVFEGKYVWDEDYPLHIQHIRCEFELKEGYIPT IQIKRSRFYKGNEYLKSSGGEIADLWLSNVDLELMKEHYDLYN VEYISGLKFKATTGLFKDFIDKWTYIKTTSEGAIKQLAKLMLN SLYGKFASNPDVTGKVPYLKENGALGFRLGEEETKDPVYTPMG VFITAWARYTTITAAQACYDRIIYCDTDSIHLTGTEIPDVIKD IVDPKKLGYWAHESTFKRAKYLRQKTYIQDIYMKEVDGKLVEG SPDDYTDIKFSVKCAGMTDKIKKKEVTFENFKVGFSRKMKPKPV QVPGGVVLVDDTFTIK |
| M2Y SEQ ID NO: 2 | MSRKMFSCDFETTTKLDDCRVWAYGYMEIGNLDNYKIGNSLDE FMQWVMEIQADLYFHNLKFDGAFIVNWLEQHGFKWSNEGLPNT YNTIISKMGQWYMIDICFGYKGKRKLHTVIYDSLKKLPFPVKK IAKDFQLPLLKGDIDYHTERPVGHEITPEEYEYIKNDIEIIAR ALDIQFKQGLDRMTAGSDSLKGFKDILSTKKFNKVFPKLSLPM DKEIRKAYRGGFTWLNDKYKEKEIGEGMVFDVNSLYPSQMYSR PLPYGAPIVFQGKYEKDEQYPLYIQRIRFEFELKEGYIPTIQI KKNPFFKGNEYLKNSGVEPVELYLTNVDLELIQEHYELYNVEY IDGFKFREKTGLFKDFIDKWTYVKTHEEGAKKQLAKLMLNSLY GKFASNPDVTGKVPYLKDDGSLGFRVGDEEYKDPVYTPMGVFI TAWARFTTITAAQACYDRIIYCDTDSIHLTGTEVPEIIKDIVD PKKLGYWAHESTFKRAKYLRQKTYIQDIYVKEVDGKLKECSPD EATTTKFSVKCAGMTDTIKKKVTFDNFAVGFSSMGKPKPVQVN GGVVLVDSVFTIK |
| HIV RT p66 SEQ ID NO: 3 | MPISPIETVPVKLKPGMDGPKVKQWPLTEEKIKALVEICTEME KEGKISKIGPENPYNTPVFAIKKKDSTKWRKLVDFRELNKRTQ DFWEVQLGIPHPAGLKKKKSVTVLDVGDAYFSVPLDEDFRKYT AFTIPSINNETPGIRYQYNVLPQGWKGSPAIFQSSMTKILEPF RKQNPDIVIYQYMDDLYVGSDLEIGQHRTKIEELRQHLLRWGL TTPDKKHQKEPPFLWMGYELHPDKWTVQPIVLPEKDSWTVNDI QKLVGKLNWASQIYPGIKVRQLCKLLRGTKALTEVIPLTEEAE LELAENREILKEPVHGVYYDPSKDLIAEIQKQGQGQWTYQIYQ EPFKNLKTGKYARMRGAHTNDVKQLTEAVQKITTESIVIWGKT PKFKLPIQKETWETWWTEYWQATWIPEWEFVNTPPLVKLWYQL EKEPIVGAETFYVDGAANRETKLGKAGYVTNRGRQKVVTLTDT TNQKTELQAIYLALQDSGLEVNIVTDSQYALGIIQAQPDQSES ELVNQIIEQLIKKEKVYLAWVPAHKGIGGNEQVDKLVSAGIRK VLF |
| HIV RT p51 SEQ ID NO: 4 | MPISPIETVPVKLKPGMDGPKVKQWPLTEEKIKALVEICTEME KEGKISKIGPENPYNTPVFAIKKKDSTKWRKLVDFRELNKRTQ DFWEVQLGIPHPAGLKKKKSVTVLDVGDAYFSVPLDEDFRKYT AFTIPSINNETPGIRYQYNVLPQGWKGSPAIFQSSMTKILEPF RKQNPDIVIYQYMDDLYVGSDLEIGQHRTKIEELRQHLLRWGL TTPDKKHQKEPPFLWMGYELHPDKWTVQPIVLPEKDSWTVNDI QKLVGKLNWASQIYPGIKVRQLCKLLRGTKALTEVIPLTEEAE LELAENREILKEPVHGVYYDPSKDLIAEIQKQGQGQWTYQIYQ EPFKNLKTGKYARMRGAHTNDVKQLTEAVQKITTESIVIWGKT PKFKLPIQKETWETWWTEYWQATWIPEWEFVNTPPLVKLW |

Nucleotide Analogs

As discussed, various polymerases of the invention can incorporate one or more nucleotide analogs into a growing oligonucleotide chain. Upon incorporation, the analog can leave a residue that is the same as or different than a natural nucleotide in the growing oligonucleotide (the polymerase can incorporate any non-standard moiety of the analog, or can cleave it off during incorporation into the oligonucleotide). A "nucleotide analog" herein is a compound, that, in a particular application, functions in a manner similar or analogous to a naturally occurring nucleoside triphosphate (a "nucleotide"), and does not otherwise denote any particular structure. A nucleotide analog is an analog other than a standard naturally occurring nucleotide, i.e., other than A, G, C, T, or U, though upon incorporation into the oligonucleotide, the resulting residue in the oligonucleotide can be the same as (or different from) an A, G, C, T, or U residue.

In one useful aspect of the invention, nucleotide analogs can also be modified to achieve any of the improved properties desired. For example, various linkers or other substituents can be incorporated into analogs that have the effect of reducing branching fraction, improving processivity, or altering rates. Modifications to the analogs can include extending the phosphate chains, e.g., to include a tetra-, penta-, hexa- or heptaphosphate group, and/or adding chemical linkers to extend the distance between the nucleotide base and the dye molecule, e.g., a fluorescent dye molecule. Substitution of one or more non-bridging oxygen in the polyphosphate, for example with S or $BH_3$, can change the polymerase reaction kinetics, e.g., to achieve a system having two slow steps as described hereinbelow. Optionally, one or more, two or more, three or more, or four or more non-bridging oxygen atoms in the polyphosphate group of the analog has an S substituted for an O. While not being bound by theory, it is believed that the properties of the nucleotide, such as the metal chelation properties, electronegativity, or steric properties, can be altered by substitution of the non-bridging oxygen(s).

Many nucleotide analogs are available and can be incorporated by the polymerases of the invention. These include analog structures with core similarity to naturally occurring nucleotides, such as those that comprise one or more substituent on a phosphate, sugar, or base moiety of the nucleoside or nucleotide relative to a naturally occurring nucleoside or nucleotide. In one embodiment, the nucleotide analog includes three phosphate containing groups; for example, the analog can be a labeled nucleoside triphosphate analog and/or an α-thiophosphate nucleotide analog having three phosphate groups. In one embodiment, a nucleotide analog can include one or more extra phosphate containing groups, relative to a nucleoside triphosphate. For example, a variety of nucleotide analogs that comprise, e.g., from 4-6 or more phosphates are described in detail in US patent application publication 2007-0072196, incorporated herein by reference in its entirety for all purposes. Other exemplary useful analogs, including tetraphosphate and pentaphosphate analogs, are described in U.S. Pat. No. 7,041,812, incorporated herein by reference in its entirety for all purposes.

For example, the analog can include a labeled compound of the formula:

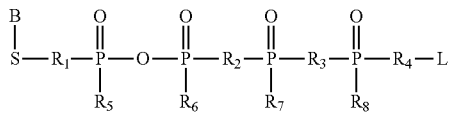

wherein B is a nucleobase (and optionally includes a label); S is selected from a sugar moiety, an acyclic moiety or a carbocyclic moiety (and optionally includes a label); L is an optional detectable label; $R_1$ is selected from O and S; $R_2$, $R_3$ and $R_4$ are independently selected from O, NH, S, methylene, substituted methylene, C(O), $C(CH_2)$, $CNH_2$, $CH_2CH_2$, and $C(OH)CH_2R$ where R is 4-pyridine or 1-imidazole, provided that $R_4$ may additionally be selected from

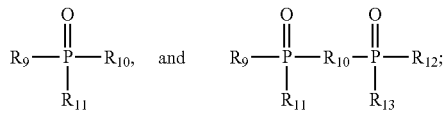

$R_5$, $R_6$, $R_7$, $R_8$, $R_{11}$ and $R_{13}$ are, when present, each independently selected from O, $BH_3$, and S; and $R_9$, $R_{10}$ and $R_{12}$ are independently selected from O, NH, S, methylene, substituted methylene, $CNH_2$, $CH_2CH_2$, and $C(OH)CH_2R$ where R is 4-pyridine or 1-imidazole. In some cases, phosphonate analogs may be employed as the analogs, e.g., where one of $R_2$, $R_3$, $R_4$, $R_9$, $R_{10}$ or $R_{12}$ are not O, e.g., they are methyl etc. See, e.g., US patent application publication 2007-0072196, previously incorporated herein by reference in its entirety for all purposes.

The base moiety incorporated into the analog is generally selected from any of the natural or non-natural nucleobases or nucleobase analogs, including, e.g., purine or pyrimidine bases that are routinely found in nucleic acids and available nucleic acid analogs, including adenine, thymine, guanine, cytidine, uracil, and in some cases, inosine. As noted, the base optionally includes a label moiety. For convenience, nucleotides and nucleotide analogs are generally referred to based upon their relative analogy to naturally occurring nucleotides. As such, an analog that operates, functionally, like adenosine triphosphate, may be generally referred to herein by the shorthand letter A. Likewise, the standard abbreviations of T, G, C, U and I, may be used in referring to analogs of naturally occurring nucleosides and nucleotides typically abbreviated in the same fashion. In some cases, a base may function in a more universal fashion, e.g., functioning like any of the purine bases in being able to hybridize with any pyrimidine base, or vice versa. The base moieties used in the present invention may include the conventional bases described herein or they may include such bases substituted at one or more side groups, or other fluorescent bases or base analogs, such as 1,N6 ethenoadenosine or pyrrolo C, in which an additional ring structure renders the B group neither a purine nor a pyrimidine. For example, in certain cases, it may be desirable to substitute one or more side groups of the base moiety with a labeling group or a component of a labeling group, such as one of a donor or acceptor fluorophore, or other labeling group. Examples of labeled nucleobases and processes for labeling such groups are described in, e.g., U.S. Pat. Nos. 5,328,824 and 5,476,928, each of which is incorporated herein by reference in its entirety for all purposes.

In the analogs, the S group is optionally a sugar moiety that provides a suitable backbone for a synthesizing nucleic acid strand. For example, the sugar moiety is optionally selected from a D-ribosyl, 2' or 3' D-deoxyribosyl, 2',3'-D-dideoxyribosyl, 2', 3'-D-didehydrodideoxyribosyl, 2' or 3' alkoxyribosyl, 2' or 3' aminoribosyl, 2' or 3' mercaptoribosyl, 2' or 3' alkothioribosyl, acyclic, carbocyclic or other modified sugar moieties. A variety of carbocyclic or acyclic moieties can be incorporated as the "S" group in place of a sugar moiety, including, e.g., those described in U.S. Patent Application Publication No. 2003/0124576, which is incorporated herein by reference in its entirety for all purposes.

For most cases, the phosphorus containing chain in the analogs, e.g., a triphosphate in conventional NTPs, is preferably coupled to the 5' hydroxyl group, as in natural nucleoside triphosphates. However, in some cases, the phosphorus containing chain is linked to the S group by the 3' hydroxyl group.

L generally refers to a detectable labeling group that is coupled to the terminal phosphorus atom via the $R_4$ (or $R_{10}$ or $R_{12}$ etc.) group. The labeling groups employed in the analogs of the invention may comprise any of a variety of detectable labels. Detectable labels generally denote a chemical moiety that provides a basis for detection of the analog compound separate and apart from the same compound lacking such a labeling group. Examples of labels include, e.g., optical labels, e.g., labels that impart a detectable optical property to the analog, electrochemical labels, e.g., labels that impart a detectable electrical or electrochemical property to the analog, and physical labels, e.g., labels that impart a different physical or spatial property to the analog, e.g., a mass tag or molecular volume tag. In some cases individual labels or combinations may be used that impart more than one of the aforementioned properties to the analogs of the invention.

Optionally, the labeling groups incorporated into the analogs comprise optically detectable moieties, such as luminescent, chemiluminescent, fluorescent, fluorogenic, chromophoric and/or chromogenic moieties, with fluorescent and/or fluorogenic labels being preferred. A variety of different label moieties are readily employed in nucleotide analogs. Such groups include, e.g., fluorescein labels, rhodamine labels, cyanine labels (i.e., Cy3, Cy5, and the like, generally available from the Amersham Biosciences division of GE Healthcare), and the Alexa family of fluorescent dyes and other fluorescent and fluorogenic dyes available from Molecular Probes/Invitrogen, Inc. and described in 'The Handbook—A Guide to Fluorescent Probes and Labeling Technologies, Eleventh Edition' (2010) (available from Invitrogen, Inc./Molecular Probes). A variety of other fluorescent and fluorogenic labels for use with nucleoside polyphosphates, and which would be applicable to the nucleotide analogs incorporated by the polymerases of the present invention, are described in, e.g., U.S. Patent Application Publication No. 2003/0124576, previously incorporated herein by reference in its entirety for all purposes.

Thus, in one illustrative example, the analog can be a phosphate analog (e.g., an analog that has more than the typical number of phosphates found in nucleoside triphosphates) that includes, e.g., an Alexa dye label. For example, an Alexa488 dye can be labeled on a delta phosphate of a tetraphosphate analog (denoted, e.g., A488dC4P or A488dA4P, for the Alexa488 labeled tetraphosphate analogs of C and A, respectively), or an Alexa568 or Alexa633 dye can be used (e.g., A568dC4P and A633dC4P, respectively, for labeled tetraphosphate analogs of C or A568dT6P for a labeled hexaphosphate analog of T), or an Alexa546 dye can be used (e.g., A546dG4P), or an Alexa594 dye can be used (e.g., A594dT4P). As additional examples, an Alexa555 dye (e.g., A555dC6P or A555dA6P), an Alexa 647 dye (e.g., A647dG6P), an Alexa 568 dye (e.g., A568dT6P), and/or an Alexa660 dye (e.g., A660dA6P or A660dC6P) can be used in, e.g., single molecule sequencing. Similarly, to facilitate color separation, a pair of fluorophores exhibiting FRET (fluorescence resonance energy transfer) can be labeled on a delta phosphate of a tetraphosphate analog (denoted, e.g., FAM-amb-A532dG4P or FAM-amb-A594dT4P).

As noted above, an analog can include a linker that extends the distance between the nucleotide base and the label moiety, e.g., a fluorescent dye moiety. Exemplary linkers and analogs are described in U.S. Pat. No. 7,968,702. Similarly, a protein or other moiety can be employed to provide spacing and/or shielding between the base and the label, e.g., as described in US patent application publication 2013-0316912 "Polymerase Enzyme Substrates with Protein Shield" and US patent application publication 2015-0050659 "Protected Fluorescent Reagent Compounds." Suitable polymerase substrates optionally include two or more nucleoside polyphosphates and/or two or more label moieties, e.g., as described in US patent application publication 2013-0316912 "Polymerase Enzyme Substrates with Protein Shield," US patent application publication 2015-0050659 "Protected Fluorescent Reagent Compounds," and US patent application publication 2009-0208957 "Alternate Labeling Strategies for Single Molecule Sequencing."

Additional details regarding labels, analogs, and methods of making such analogs can be found in US patent application publication 2007-0072196 "Fluorescent Nucleotide Analogs and Uses Therefor," WO 2007/041342 "Labeled Nucleotide Analogs and Uses Therefor," WO 2009/114182 "Labeled Reactants and Their Uses," US patent application publication 2009-0208957 "Alternate Labelling Strategies for Single Molecule Sequencing," U.S. patent application Ser. No. 13/218,412 "Functionalized Cyanine Dyes," U.S. patent application Ser. No. 13/218,395 "Functionalized Cyanine Dyes," U.S. patent application Ser. No. 13/218,428 "Cyanine Dyes," US patent application publication 2012-0077189 "Scaffold-Based Polymerase Enzyme Substrates," US patent application publication 2010-0167299 "Phospholink Nucleotides for Sequencing Applications," US patent application publication 2010-0152424 "Modular Nucleotide Compositions and Uses Therefor," US patent application publication 2013-0316912 "Polymerase Enzyme Substrates with Protein Shield," US patent application publication 2015-0050659 "Protected Fluorescent Reagent Compounds," U.S. patent application 62/258,414 "Modified Nucleotide Reagents," U.S. patent application 62/258,415 "Protected Dye-Labeled Reagents," U.S. patent application 62/258,416 "Labeled Nucleotide Analogs, Reaction Mixtures, and Methods and Systems for Sequencing," and U.S. Pat. No. 8,652,779 "Nanopore Sequencing Using Charge Blockade Labels," each of which is incorporated herein by reference in its entirety for all purposes.

Applications for Enhanced Nucleic Acid Amplification and Sequencing

Polymerases of the invention, e.g., modified recombinant polymerases, are optionally used in combination with nucleotides and/or nucleotide analogs and nucleic acid templates (e.g., DNA, RNA, or hybrids, analogs, derivatives, or mimetics thereof) to copy the template nucleic acid. That is, a mixture of the polymerase, nucleotides/analogs, and optionally other appropriate reagents, the template, and a replication initiating moiety (e.g., primer) is reacted such that the polymerase synthesizes nucleic acid (e.g., extends the primer) in a template-dependent manner. The replication initiating moiety can be a standard oligonucleotide primer, or, alternatively, a component of the template, e.g., the template can be a self-priming single stranded RNA, a nicked double stranded RNA, or the like. Similarly, a terminal protein can serve as an initiating moiety. At least one nucleotide analog can be incorporated into the DNA product. The template can be a linear or circular nucleic acid, and in certain applications, is desirably a circular template (e.g., for rolling circle replication or for sequencing of circular templates), e.g., a simple circle or a SMRTbell™ as described in, e.g., U.S. Pat. No. 8,153,375 "Compositions and Methods for Nucleic Acid Sequencing" and Travers et al. (2010) Nucl. Acids Res. 38(15):e159, previously incorporated by reference. Other suitable templates include hairpins; see, e.g., U.S. Patent Application Publication No. 2015/0152492. The template can be essentially any desired RNA, including, but not limited to, an mRNA, rRNA, tRNA, miRNA, piRNA, saRNA, siRNA, ribozyme, CRISPR RNA, catalytic RNA, antisense RNA, long ncRNA, or a fragment or derivative thereof. Optionally, the template is an RNA/DNA hybrid, e.g., a nucleic acid strand including at least one stretch of ribonucleotides and at least one stretch of deoxyribonucleotides. The region of ribonucleotides in the template typically includes 10 or more contiguous ribonucleotides, preferably 20 or more, 50 or more, 100 or more, 500 or more, 1000 or more, or even 2000 or more contiguous ribonucleotides. In one exemplary class of embodiments, the template is a circular nucleic acid having a double-stranded central region and two single-stranded hairpin end regions; one strand of the central region can comprise or consist of ribonucleotides (e.g., a stretch of ribonucleotides flanked by deoxyribonucleotides) while the other strand of the central region contains deoxyribonucleotides. For example, one strand of the central region can comprise an mRNA (or other RNA) or fragment thereof while the other strand comprises its cDNA complement. Sequencing of both strands with a polymerase capable of employing both RNA and DNA templates can, e.g., provide high accuracy sequence information using information obtained from the DNA strand and provide information on base modifications, confirm the identity of splice variants, and the like using information obtained from the RNA strand. Such circular templates are readily produced using techniques known in the art. For example, a primer (e.g., oligo dT or a sequence specific primer) is hybridized to an RNA and cDNA is produced by reverse transcription; hairpin adapters are then ligated to each end of the resulting DNA/RNA hybrid to form the desired circular template. DNA linkers are optionally ligated to the 3' and/or 5' end of the RNA prior to priming and reverse transcription, e.g., to facilitate sequencing of the full-length RNA and to improve efficiency of ligation of the hairpin adapters. Where a 3' DNA linker is employed, the primer can be complementary to the linker.

Optionally, the composition can be present in an automated nucleic acid replication and/or sequencing system. For additional information on exemplary sequencing systems, see, e.g., U.S. Pat. No. 9,062,091, incorporated herein by reference in its entirety for all purposes, and U.S. Pat. No. 8,501,405, previously incorporated by reference. In some cases, the compositions, methods, and systems of the invention can be used as part of an integrated sequencing system, for example, as described in US 20120014837 "Illumination of Integrated Analytical Systems," US 20120021525 "Optics Collection and Detection System and Method," US 20120019828 "Integrated Analytical System and Method," U.S. Pat. No. 9,372,308 "Arrays of Integrated Analytical Devices and Methods for Production," and US 20120085894 "Substrates and Optical Systems and Methods of Use Thereof," which are incorporated herein by reference in their entirety for all purposes.

Incorporation of labeled nucleotide analogs by the polymerases of the invention is particularly useful in a variety of different nucleic acid analyses, including real-time monitoring of DNA polymerization. The label can itself be incorporated, or more preferably, can be released during incorporation of the analog. For example, analog incorporation can be monitored in real time by monitoring label release during incorporation of the analog by the polymerase. The portion of the analog that is incorporated can be the same as a natural nucleotide, or can include features of the analog that differ from a natural nucleotide.

In general, label incorporation or release can be used to indicate the presence and composition of a growing nucleic acid strand, e.g., providing evidence of template replication/amplification and/or sequence of the template. Signaling from the incorporation can be the result of detecting labeling groups that are liberated from the incorporated analog, e.g., in a solid phase assay, or can arise upon the incorporation reaction. For example, in the case of FRET labels where a bound label is quenched and a free label is not, release of a label group from the incorporated analog can give rise to a fluorescent signal. Alternatively, the enzyme may be labeled with one member of a FRET pair proximal to the active site, and incorporation of an analog bearing the other member will allow energy transfer upon incorporation. The use of enzyme bound FRET components in nucleic acid sequencing applications is described, e.g., in U.S. Patent Application Publication No. 2003/0044781, incorporated herein by reference.

In one example reaction of interest, a polymerase reaction can be isolated within an extremely small observation volume that effectively results in observation of individual polymerase molecules. As a result, the incorporation event provides observation of an incorporating nucleotide analog that is readily distinguishable from non-incorporated nucleotide analogs. In a preferred aspect, such small observation volumes are provided by immobilizing the polymerase enzyme within an optical confinement, such as a Zero Mode Waveguide (ZMW). For a description of ZMWs and their application in single molecule analyses, and particularly nucleic acid sequencing, see, e.g., U.S. Patent Application Publication No. 2003/0044781 and U.S. Pat. No. 6,917,726, each of which is incorporated herein by reference in its entirety for all purposes. See also Levene et al. (2003) "Zero-mode waveguides for single-molecule analysis at high concentrations" Science 299:682-686, Eid et al. (2009) "Real-time DNA sequencing from single polymerase molecules" Science 323:133-138, and U.S. Pat. Nos. 7,056,676, 7,056,661, 7,052,847, 7,033,764, and 7,907,800, the full disclosures of which are incorporated herein by reference in their entirety for all purposes.

In general, a polymerase enzyme is complexed with the template strand in the presence of one or more nucleotides and/or one or more nucleotide analogs. For example, in certain embodiments, labeled analogs are present representing analogous compounds to each of the four natural nucleotides, A, T, G and C, e.g., in separate polymerase reactions, as in classical Sanger sequencing, or multiplexed together, e.g., in a single reaction, as in multiplexed sequencing approaches. When a particular base in the template strand is encountered by the polymerase during the polymerization reaction, it complexes with an available analog that is complementary to such nucleotide, and incorporates that analog into the nascent and growing nucleic acid strand. In one aspect, incorporation can result in a label being released, e.g., in polyphosphate analogs, cleaving between the α and β phosphorus atoms in the analog, and consequently releasing the labeling group (or a portion thereof). The incorporation event is detected, either by virtue of a longer presence of the analog and, thus, the label, in the complex, or by virtue of release of the label group into the surrounding medium. Where different labeling groups are used for each of the types of analogs, e.g., A, T, G or C, identification of a label of an incorporated analog allows identification of that analog and consequently, determination of the complementary nucleotide in the template strand being processed at that time. Sequential reaction and monitoring permits real-time monitoring of the polymerization reaction and determination of the sequence of the template nucleic acid. As noted above, in particularly preferred aspects, the polymerase enzyme/template complex is provided immobilized within an optical confinement that permits observation of an individual complex, e.g., a zero mode waveguide. For additional information on single molecule sequencing monitoring incorporation of phosphate-labeled analogs in real time, see, e.g., Eid et al. (2009) "Real-time DNA sequencing from single polymerase molecules" Science 323:133-138.

Figure 4A:
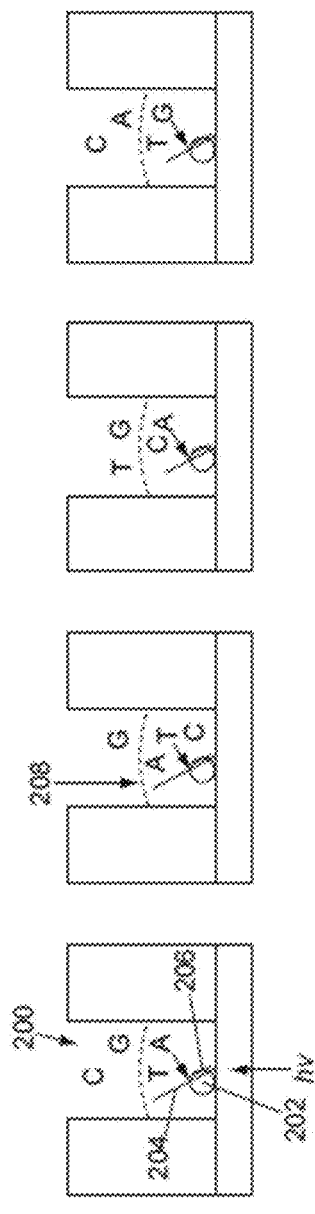
FIGS. 4A-4B schematically illustrate an exemplary single molecule sequencing by incorporation process in which the compositions of the invention provide particular advantages.

In a first exemplary technique, as schematically illustrated in FIG. 4A, a nucleic acid synthesis complex, including a polymerase enzyme 202, a template sequence 204, and a complementary primer sequence 206, is provided immobilized within an observation region 200 that permits illumination (as shown by hv) and observation of a small volume that includes the complex without excessive illumination of the surrounding volume (as illustrated by dashed line 208). By illuminating and observing only the volume immediately surrounding the complex, one can readily identify fluorescently labeled nucleotides that become incorporated during that synthesis, as such nucleotides are retained within that observation volume by the polymerase for longer periods than those nucleotides that are simply randomly diffusing into and out of that volume.

Figure 4B:
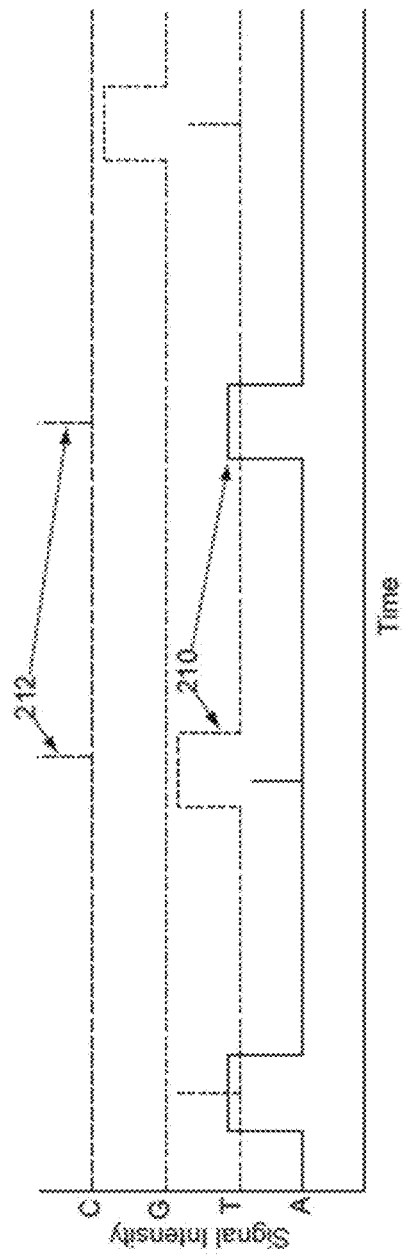

In particular, as shown in FIG. 4B, when a nucleotide, e.g., A, is incorporated into DNA by the polymerase, it is retained within the observation volume for a prolonged period of time, and upon continued illumination yields a prolonged fluorescent signal (shown by peak 210). By comparison, randomly diffusing and not incorporated nucleotides remain within the observation volume for much shorter periods of time, and thus produce only transient signals (such as peak 212), many of which go undetected due to their extremely short duration.

In particularly preferred exemplary systems, the confined illumination volume is provided through the use of arrays of optically confined apertures termed zero mode waveguides (ZMWs), e.g., as shown by confined reaction region 200 (see, e.g., U.S. Pat. No. 6,917,726, which is incorporated herein by reference in its entirety for all purposes). For sequencing applications, the polymerase is typically provided immobilized upon the bottom of the ZMW, although another component of the complex (e.g., a primer or template) is optionally immobilized on the bottom of the ZMW to localize the complex. See, e.g., Korlach et al. (2008) PNAS U.S.A. 105(4):1176-1181, U.S. Pat. Nos. 8,802,600, and 8,501,406, each of which is incorporated herein by reference in its entirety for all purposes.

In operation, the fluorescently labeled nucleotides (shown as A, C, G and T) bear one or more fluorescent dye groups on a terminal phosphate moiety that is cleaved from the nucleotide upon incorporation. As a result, synthesized nucleic acids do not bear the build-up of fluorescent labels, as the labeled polyphosphate groups diffuse away from the complex following incorporation of the associated nucleotide, nor do such labels interfere with the incorporation event. See, e.g., Korlach et al. (2008) Nucleosides, Nucleotides and Nucleic Acids 27:1072-1083. For an illustration of pulses (peaks) representing incorporation of different nucleotide analogs, pulse width, and interpulse distance, see, e.g., US patent application publication US-2014-0094375.

In a second exemplary technique, the immobilized complex and the nucleotides to be incorporated are each provided with interactive labeling components. Upon incorporation, the nucleotide borne labeling component is brought into sufficient proximity to the complex borne (or complex proximal) labeling component, such that these components produce a characteristic signal event. For example, the polymerase may be provided with a fluorophore that provides fluorescent resonant energy transfer (FRET) to appropriate acceptor fluorophores. These acceptor fluorophores are provided upon the nucleotide to be incorporated, where each type of nucleotide bears a different acceptor fluorophore, e.g., that provides a different fluorescent signal. Upon incorporation, the donor and acceptor are brought close enough together to generate energy transfer signal. By providing different acceptor labels on the different types of nucleotides, one obtains a characteristic FRET-based fluorescent signal for the incorporation of each type of nucleotide, as the incorporation is occurring.

In a related aspect, a nucleotide analog may include two interacting fluorophores that operate as a donor/quencher pair, where one member is present on the nucleobase or other retained portion of the nucleotide, while the other member is present on a phosphate group or other portion of the nucleotide that is released upon incorporation, e.g., a terminal phosphate group. Prior to incorporation, the donor and quencher are sufficiently proximal on the same analog as to provide characteristic signal quenching. Upon incorporation and cleavage of the terminal phosphate groups, e.g., bearing a donor fluorophore, the quenching is removed and the resulting characteristic fluorescent signal of the donor is observable.

In exploiting the foregoing processes, where the incorporation reaction occurs too rapidly, it may result in the incorporation event not being detected, i.e., the event speed exceeds the detection speed of the monitoring system. The missed detection of incorporated nucleotides can lead to an increased rate of errors in sequence determination, as omissions in the real sequence. In order to mitigate the potential for missed pulses due to short reaction or product release times, in one aspect, the current invention can result in increased reaction and/or product release times during incorporation cycles. Similarly, very short interpulse distances can occasionally cause pulse merging. An advantage of employing polymerases with reduced reaction rates, e.g., polymerases exhibiting decreased rates and/or two slow-step kinetics as described in US patent application publications 2009-0286245 and 2010-0112645, is an increased frequency of longer, detectable, binding events. This advantage may also be seen as an increased ratio of longer, detectable pulses to shorter, non-detectable pulses, where the pulses represent binding events.

In another exemplary technique, the nucleotide analogs are blocked at their 3' hydroxyl group with a labeled leaving group, preventing extension from the incorporated nucleotide until the labeled leaving group is removed. Signal from an incorporated nucleotide can thus be prolonged. The leaving group is removed by a selective cleaving activity (e.g., a 3' exonuclease activity), permitting incorporation of the next nucleotide. For additional details, see U.S. Pat. No. 8,603,741.

Direct incorporation of labeled phospholinked nucleotides, as in the above techniques, represents an extremely efficient operational mode of this RNA sequencing method. Alternatively, RNA sequence information can also be obtained by detecting just the binding events of labeled nucleotides (e.g., phospholinked or base-labeled) in the active site, without subsequent catalysis by the enzyme, e.g., in the case of labeled nucleotides that are not incorporatable by the polymerase, e.g., due to a non-cleavable bond between the alpha and beta phosphate groups of the nucleotides or other modifications rendering the nucleotides chemically unincorporatable, the presence of a blocking group at the 3' end of the primer, the absence of reaction components (e.g., divalent cations) that are required for incorporation, the presence of non-catalytic metal ions (e.g., $Ca^{2+}$, $Sr^{2+}$, $Ba^{2+}$, $Zn^{2+}$, etc.), and the like. This repetitive "sampling" of the active site by the cognate labeled nucleotide (also referred to as "cognate sampling") is detected via fluorescence pulses. Methods of sequence analysis using cognate sampling are further described in U.S. Pat. No. 8,530,164, incorporated herein by reference in its entirety for all purposes.

Cognate sampling can, in some embodiments, be followed by the eventual incorporation of a nucleotide. For example, reaction conditions that allow sampling but not incorporation can be changed to allow incorporation of nucleotides that were previously unincorporatable, e.g., due to a missing reaction component, such as a divalent cation. In some embodiments, the incorporation event post-sampling is limited to one nucleotide, e.g., by virtue of a blocking group incorporated into the nucleotide finally incorporated. For example, after allowing cognate sampling under conditions that do not permit incorporation ("sampling conditions"), the reaction conditions are modified to allow incorporation, but because the nucleotide analogs comprise blocking groups that prevent further primer extension, only one nucleotide analog is incorporated. Following detection of incorporation, the sampling conditions are restored, e.g., by buffer exchange, and the blocking group is subsequently removed, thereby allowing sampling of nucleotide analogs complementary to the next position of the template. The process can be repeated to generate a nascent strand of a desired length.

In embodiments in which a sampled nucleotide comprises a modification that does not permit incorporation by the polymerase, a labeled or unlabeled nucleotide that does not comprise the modification can be incorporated. For example, such an unmodified nucleotide can be added to the reaction mixture during the reaction, or can be present in the solution with the modified nucleotide, e.g., at a lower concentration. The concentration of the incorporatable nucleotide analog can be adjusted to promote a desired average number of sampling events prior to incorporation. See, e.g., U.S. Pat. No. 8,252,911, incorporated by reference herein in its entirety. After incorporation, the polymerase translocates to the next position and the cycle begins again.

The sequence of repetitive associations of complementary unincorporatable nucleotides with the polymerase complex is complementary to the sequence of the RNA template, and the data so generated is subjected to statistical analysis to produce sequence "reads" for both the nascent polynucleotide and, by complementarity, for the RNA template. The ratio of labeled to unlabeled nucleotides can be tuned to adjust the number of labeled analog active-site sampling events before incorporation and translocation to the next base occurs. Further, statistical analysis of various metrics can distinguish between the incorporation of a single nucleotide and multiple incorporations of identical nucleotides (homonucleotide repeats). For example, the average number of sampling events (or "pulses") per incorporation event follows an exponential distribution such that incorporation of one nucleotide can be distinguished from incorporation of multiple identical nucleotides, so the distribution and/or average number of pulses at a given location on a template is indicative of the number of identical nucleotides incorporated into the complementary strand. Alternatively or additionally, the total time for a polymerase to pass through a homonucleotide repeat is also indicative of the number of identical nucleotides in the repeat such that the distribution and/or average time it takes for a polymerase to complete incorporation of one type of nucleotide is indicative of the number of identical nucleotides incorporated into the complementary strand. The reaction conditions and/or choice of polymerase can be adjusted to accentuate these behaviors and, thereby, facilitate determination of the sequence of nucleotides incorporated into a newly synthesized nucleic acid, for example, conditions that favor cognate sampling over incorporation and conditions that slow the rate of incorporation. Various methods for modifying reaction conditions and/or enzymes to affect enzyme kinetics are provided, e.g., in U.S. Patent Publication No. 2010/0047802; U.S. patent application Ser. No. 12/584,481, filed Sep. 4, 2009; and U.S. patent application Ser. No. 12/384,112, filed Mar. 30, 2009, the disclosures of which are incorporated herein by reference in their entireties for all purposes.

For additional discussion of RNA sequencing, including detection of secondary structure in base modifications, see, e.g., U.S. Pat. Nos. 8,501,405, 9,175,341, 9,175,338, and Vilfan et al. (2013) "Analysis of RNA base modification and structural rearrangement by single-molecule real-time detection of reverse transcription" Journal of Nanobiotechnology 11:8, each previously incorporated by reference.

The polymerases described herein can also be employed in other sequencing modalities, e.g., nanopore or nanoFET sequencing. For a discussion of nanopore sequencing, see, e.g., WO2011067559, EP1951898, U.S. Pat. Nos. 6,673,615, 6,362,002, 5,795,782, 8,652,779, 9,017,937, 9,116,118, Mirsaidov et al. (2009) "Nanoelectromechanics of methylated DNA in a synthetic nanopore" Biophys. J. 96:L32-L34, Wanunu et al. (2010) "Discrimination of methylcytosine from hydroxymethylcytosine in DNA molecules" J. Am. Chem. Soc. 133:486-492, and Manrao et al. (2012) "Reading DNA at single-nucleotide resolution with a mutant MspA nanopore and phi29 DNA polymerase" Nature Biotechnology 30:349-353, which are incorporated herein by reference in their entirety for all purposes. For a discussion of nanoFET sequencing, see, e.g., US patent application publication 2015-0065353 and U.S. patent application Ser. No. 15/227,661, filed Aug. 3, 2016.

In addition to their use in sequencing, the polymerases of the invention are also useful in a variety of other genotyping analyses, e.g., SNP genotyping using single base extension methods, real time monitoring of amplification, e.g., RT-PCR methods, and the like. The polymerases of the invention are also useful in amplifying nucleic acids, e.g., DNAs or RNAs, including, for example, in applications such as whole genome or transcriptome amplification.

It is understood that the examples and embodiments described herein are for illustrative purposes only and that various modifications or changes in light thereof will be suggested to persons skilled in the art and are to be included within the spirit and purview of this application and scope of the appended claims. While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference

What is claimed is:

1. A reaction mixture comprising a polymerase enzyme complex comprising a polymerase enzyme and a template nucleic acid that comprises RNA,
   wherein the polymerase is a recombinant reverse transcriptase, which recombinant reverse transcriptase comprises an amino acid sequence that is at least 80% identical to SEQ ID NO:3, and which recombinant reverse transcriptase comprises a first cysteine residue at a position selected from W25, K14, and K23 and a second cysteine residue at a position selected from K288 and A289, wherein identification of positions is relative to SEQ ID NO:3,
   wherein the side chains of the first and second cysteine residues are covalently connected by a linker, thereby topologically encircling the template nucleic acid.

2. The reaction mixture of claim 1, wherein the template nucleic acid is circular.

3. The reaction mixture of claim 1, wherein the template nucleic acid is an mRNA.

4. The reaction mixture of claim 1, comprising a primer hybridized to the template nucleic acid.

5. The reaction mixture of claim 1, wherein the polymerase enzyme complex is immobilized on a surface.

6. The reaction mixture of claim 5, comprising sequencing reagents in contact with the surface, which sequencing reagents comprise reagents for carrying out nucleic acid synthesis including one or more labeled nucleotide analogs.

7. The reaction mixture of claim 1, comprising a phosphate-labeled nucleotide analog, wherein the polymerase incorporates the nucleotide analog into a copy nucleic acid in response to the template nucleic acid.

8. A method for sequencing a nucleic acid template comprising:
   providing a polymerase enzyme complex comprising a polymerase enzyme, a template nucleic acid that comprises RNA, and optionally a primer hybridized to the template nucleic acid, wherein the polymerase is a recombinant reverse transcriptase, which recombinant reverse transcriptase comprises an amino acid sequence that is at least 80% identical to SEQ ID NO:3, and which recombinant reverse transcriptase comprises a first cysteine residue at a position selected from W25, K14, and K23 and a second cysteine residue at a position selected from K288 and A289, wherein identification of positions is relative to SEQ ID NO:3, wherein the side chains of the first and second cysteine residues are covalently connected by a linker, thereby topologically encircling the template nucleic acid, wherein the polymerase enzyme complex is immobilized on a surface;
   adding sequencing reagents in contact with the surface comprising reagents for carrying out nucleic acid synthesis including one or more labeled nucleotide analogs; and
   determining the sequential addition of nucleotide residues to a nucleic acid strand complementary to a strand of the template nucleic acid by observing the interaction of the labeled nucleotide analogs with the polymerase enzyme complex.

9. A system for sequencing nucleic acids comprising:
   a chip comprising a plurality of polymerase enzyme complexes bound thereto, each polymerase enzyme complex individually optically resolvable, each polymerase enzyme complex comprising a polymerase enzyme, a template nucleic acid comprising RNA, and optionally a primer hybridized to the template nucleic acid, wherein the polymerase is a recombinant reverse transcriptase, which recombinant reverse transcriptase comprises an amino acid sequence that is at least 80% identical to SEQ ID NO:3, and which recombinant reverse transcriptase comprises a first cysteine residue at a position selected from W25, K14, and K23 and a second cysteine residue at a position selected from K288 and A289, wherein identification of positions is relative to SEQ ID NO:3, wherein the side chains of the first and second cysteine residues are covalently connected by a linker, thereby topologically encircling the template nucleic acid;
   sequencing reagents in contact with the surface comprising reagents for carrying out nucleic acid synthesis including one or more labeled nucleotide analogs;
   an illumination system for illuminating the polymerase enzyme complexes;
   an optical detection system for detecting fluorescence from the labeled nucleotide analogs while they are interacting with the polymerase enzyme complexes; and
   a computer for analyzing the signals detected by the detection system to determine the sequential addition of nucleotide residues to a nucleic acid strand complementary to a strand of the template nucleic acid.

10. The reaction mixture of claim 1, wherein the recombinant reverse transcriptase comprises a first cysteine residue at position W25 and a second cysteine residue at position K288, wherein identification of positions is relative to SEQ ID NO:3, wherein the side chains of the cysteine residues at positions W25 and K288 are covalently connected by a linker.

11. The reaction mixture of claim 1, wherein the recombinant reverse transcriptase comprises an amino acid sequence that is at least 95% identical to SEQ ID NO:3.

12. The reaction mixture of claim 1, wherein the recombinant reverse transcriptase comprises an amino acid sequence that is at least 90% identical to SEQ ID NO:3.

* * * * *